United States Patent [19]

Niho et al.

[11] Patent Number: 5,583,227
[45] Date of Patent: Dec. 10, 1996

[54] ANTIULCER COMPOUNDS HAVING A SUBSTITUTED ALKYNYL OR QUINOXALINE NUCLEUS AND METHODS OF MAKING THEREOF

[75] Inventors: Takeshi Niho; Ichiro Yamamoto; Hidenori Mochizuki, all of Tokyo; Ikuo Kimura, Ibaraki; Akihiro Imai, Ibaraki; Tetsuyuki Nakase, Ibaraki, all of Japan

[73] Assignees: Mochida Pharmaceutical Co. Ltd., Tokyo; Hodogaya Chemical Co. Ltd., Kanagawa, both of Japan

[21] Appl. No.: 458,871

[22] Filed: Jun. 2, 1995

[30] Foreign Application Priority Data

Jun. 3, 1994 [JP] Japan ..................... 6-122898

[51] Int. Cl.$^6$ .................. C07D 241/42; A61K 31/33
[52] U.S. Cl. .................. 544/353; 544/354; 544/355; 544/356
[58] Field of Search .................. 544/353, 354, 544/355, 356; 514/249

[56] References Cited

PUBLICATIONS

Ames et al., J.C.S. Perkin Trans. I. (7) pp. 1384–1389 (1980).
Ames et al., J. Chem. Research (S), 144–145 (1985).
Akita et al., Chem. Pharm. Bull. 34(4) 1447–1458 (1986).
Iijima et al., Yakagaku Zasshi, 108, No. 6, 586–590 (1988).
Ames et al., Synthesis, No. 5, 364–365 (1981).
Toshihide et al., Patent Abst. of Japan, 5, 45 (C–048) (1981).
Toshihide et al., Patent Abst. of Japan, 5, 41 (C–047) (1981).

*Primary Examiner*—Mukund J. Shah
*Assistant Examiner*—Richard S. Myers, Jr.
*Attorney, Agent, or Firm*—Birch, Stewart, Kolasch & Birch, LLP

[57] ABSTRACT

This invention relates to a novel compound which is useful as a drug in preventing and/or treating peptic ulcer-related diseases, to a production process thereof and to a pharmaceutical composition containing the same.

Particularly, it provides a compound which has a specified substituted alkynylpyrazine nucleus or a specified substituted alkynylquinoxaline nucleus, represented by the following formula (I)

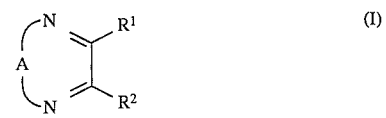

wherein A is represented by the following formula (II) or (III)

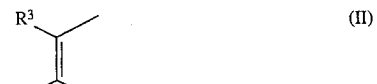

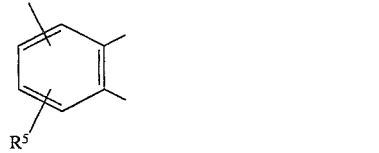

and $R^1$ is represented by the following formula (IV),

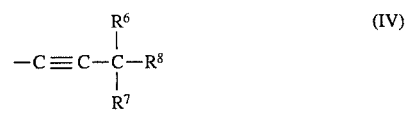

and the salts thereof, a production process thereof and a pharmaceutical composition containing the same.

The inventive compound is useful as a drug in preventing and/or treating peptic ulcer-related diseases.

8 Claims, 20 Drawing Sheets

1

2

3

4

5

6

7

8

9

10

11

12

13

14

15

16

17

18

19

20

21

22

23

24

25

26

27

28

29

30

31

32

33

34

35

36

37

38

39

40

41

42

43

44

45

46

47

48

49

50

51

52

53

54

55

56

57

58

59

60

61

62

63

64

65

66

67

68

69

70

71

72

73

74

75

76

77

78

79

80

81

82

83

84

85

86

87

88

89

90

91

92

93

94

95

96

97

98

99

100

101

102

103

104

105

106

107

108

109

110

111

112

113

114

115

116

117

118

119

120

121

122

123

124

125

126

127

128

129

130

131

132

133

134

135

136

137

138

139

140

141

142

143

144

145

146

147

148

149

150

151

152

153

154

155

156

157

158

159

ANTIULCER COMPOUNDS HAVING A SUBSTITUTED ALKYNYL OR QUINOXALINE NUCLEUS AND METHODS OF MAKING THEREOF

FIELD OF THE INVENTION

This invention relates to novel alkyne derivatives having a pyrazine or quinoxaline nucleus, to a process for the production thereof and to a pharmaceutical composition which contains at least one of the derivatives as an active ingredient and is useful as a drug for the prevention and/or treatment of peptic ulcer-related diseases.

BACKGROUND OF THE INVENTION

Excess secretion of acid in the stomach is one of the important factors which cause peptic ulcers. Because of this, administration of drugs which neutralize the acid or inhibit secretion of the acid is used for the treatment of peptic ulcers.

For example, sodium bicarbonate, magnesium oxide and the like are clinically used as antacids which neutralize the acid. Such antacids, however, are a burden to patients because of the necessity of frequent administration, and they also have side effects such as alkalosis and the like. On the other hand, anticholinergics such as atropine, pirenzepine and the like are used clinically as acid secretion inhibitors. However, such anticholinergics are not necessarily high in the selectivity for gastric acid secretion and cause side effects such as thirst, visual acuity disorder, urinary retention, tachycardia and the like. Also used clinically as acid secretion inhibitors are histamine $H_2$-receptor antagonists such as cimetidine, ranitidine, famotidine and the like. However, these histamine $H_2$-receptor antagonists are not effective in healing certain types of intractable ulcer and it is also pointed out that these antagonists cause side effects such as milk secretion due to increased blood prolactin level, gynecomastia induced by anti-androgen reaction and inhibition of the metabolism of other drugs in the liver.

Recently, proton pump inhibitors, such as omeprazole, which inhibit proton pump functioning in the final stage of the gastric acid secretion are clinically used and resulting in an efficacy similar to or higher than that of histamine $H_2$-receptor antagonists. In addition, since the proton pump functions in the final stage of the acid secretion, these proton pump inhibitors are also effective on histamine-independent gastric acid secretion and therefore partially effective in healing intractable ulcers which cannot be healed by histamine $H_2$-receptor antagonists.

However, since peptic ulcers are apt to relapse, they can be healed but their relapse can hardly be avoided even by the use of these histamine $H_2$-receptor antagonists or proton pump inhibitors. The following is considered to be one of the reason for this problem. That is, in the normal stomach, gastric acid and gastric mucosa defense mechanism keep balance with each other so that the stomach is not damaged by the acid secreted by itself. However, such a balance is lost and a peptic ulcer is generated when excess secretion of the acid occurs or function of the gastric mucosa defense mechanism is reduced. When a histamine $H_2$-receptor antagonist or a proton pump inhibitor is administered as a therapeutic drug of the peptic ulcer, secretion of the acid decreases so that it becomes unnecessary to control the gastric mucosa defense mechanism at similar level to that before the drug administration. Because of this, the function of the gastric mucosa defense mechanism is reduced when the peptic ulcer is healed and the drug administration becomes unnecessary. In consequence, when administration of the histamine $H_2$-receptor antagonist or proton pump inhibitor is terminated under such conditions, the acid secretion quantity quickly returns to the level prior to the drug administration, but the gastric mucosa defense mechanism is not restored quickly to its normal state, thus putting the gastric acid and the gastric mucosa defense mechanism out of balance and relapsing of the peptic ulcer.

Under such circumstances described above, great concern has been directed toward the development of a therapeutic agent having a broad range of efficacy, namely a drug for use in the prevention and/or treatment of peptic ulcer-related diseases, which is effective on intractable ulcers that cannot be healed by the prior art drugs and which can prevent relapse of ulcers.

SUMMARY OF THE INVENTION

In view of the above, it therefore becomes an object of the present invention to provide a novel compound or a salt thereof whose structure is different from those of the prior art drugs and which is possessed of excellent properties such as proton pump inhibition activity, gastric acid secretion inhibition activity, cell protection function and the like, and which has high safety with less side effects. The present invention also provides a process for the production of the novel compound and salts thereof and a pharmaceutical composition and an acid secretion inhibitor which contain the compound. The inventive compound shows high efficiency in various morbid states including intractable ulcers which are resistant to $H_2$-receptor antagonists and has at least a peptic ulcer-healing effect or a relapse preventing effect.

Based on an assumption that healing of intractable ulcers and prevention of their relapse could be effected by the use of a compound having both proton pump inhibition activity and cell protection function, the inventors of the present invention have conducted intensive studies and found as the result that a series of alkyne derivatives having a pyrazine or quinoxaline nucleus are possessed of at least more than one of proton pump inhibition activity, gastric acid secretion inhibition activity, antiulcer activity and cell protection function. The present invention has been accomplished on the basis of this finding.

According to a first aspect of the present invention, there is provided a compound represented by the following general formula (I) or a salt thereof

wherein A is a group represented by the following formula (II)

or the following formula (III);

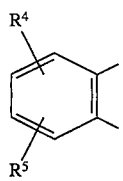

$R^1$ is a group represented by the following formula (IV);

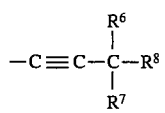

$R^6$ represents a hydrogen atom, a straight- or branched-chain or cyclic alkyl group having 1 to 6 carbon atoms or an alkoxy group having 1 or 2 carbon atoms; $R^7$ represents a hydrogen atom or an alkyl group having 1 or 2 carbon atoms, $R^6$ and $R^7$ together with their adjoining carbon atom may form a cycloalkylidene group having 3 to 6 carbon atoms or $R^6$, $R^7$ and $R^8$ together with their adjoining carbon atom may form a cycloalkyl group having 3 to 6 carbon atoms; $R^8$ represents a hydrogen atom, a straight- or branched-chain alkyl group having 1 to 3 carbon atoms which may be substituted with a group selected from an alkoxy group having 1 or 2 carbon atoms and an alkylthio group having 1 or 2 carbon atoms, an alkenyloxy group having 2 to 4 carbon atoms, a straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms, a carbamoyloxy group, an acetoxy group or a methylthio group; $R^2$ represents a hydrogen atom, a methoxy group, a halogen atom, an amino group which may be substituted with 1 or 2 alkyl groups having 1 or 2 carbon atoms, a trifluoromethyl group, a straight- or branched-chain alkyl group having 1 to 6 carbon atoms, an alkoxycarbonyl group having 1 or 2 carbon atoms, a methylthio group, a methylsulfinyl group, a methylsulfonyl group or a group selected from the aforementioned groups represented by $R^1$; $R^1$ and $R^2$ may be the same or different from each other; $R^3$ represents an alkoxycarbonyl group having 1 or 2 carbon atoms, a cyano group, a carboxyl group or a carbamoyl group; $R^4$ represents a hydrogen atom or a methoxy group; and $R^5$ represents a hydrogen atom, a methoxy group, a halogen atom, a methoxycarbonyl group, a methyl group, a hydroxymethyl group, a methoxymethyl group, a carbamoyl group, a bis(ethoxycarbonyl)acetyl group, an acetyl group, a 1-hydroxyiminoethyl group, a 1-methoxyiminoethyl group, a formyl group or a cyano group.

Preferred combinations of the substituent groups in the compound represented by the aforementioned formula (I) are as follows, though the present invention is not restricted thereby.

In the case of a combination of $R^1$, $R^2$ and $R^8$ when $R^1$ is represented by the formula (IV), it is preferable that $R^1$ and $R^2$ are the same group and $R^8$ is a straight- or branched-chain alkyl group having 1 to 3 carbon atoms which is substituted with an alkoxy group having 1 or 2 carbon atoms or a straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms.

In addition to this combination, when A of the formula (I) is a group represented by the formula (II), it is preferable that $R^3$ is an alkoxycarbonyl group having 1 or 2 carbon atoms.

Also, when A of the formula (I) is a group represented by the formula (III), it is preferable that $R^4$ is a hydrogen atom, $R^5$ is a hydrogen atom or a methoxy, hydroxymethyl or acetyl group at the 6-position and at least one of $R^6$ and $R^7$ is an alkyl group having 1 or 2 carbon atoms.

According to a second aspect of the present invention, there is provided a process for the production of the compound of formula (I) or a salt thereof (reaction scheme A and B).

<Reaction A>

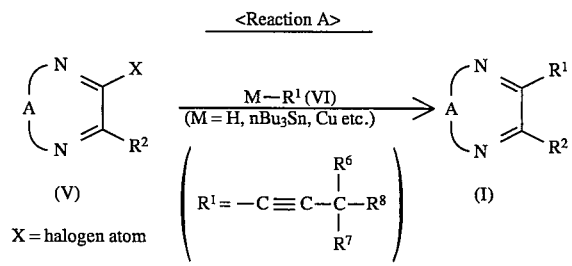

<Reaction B>

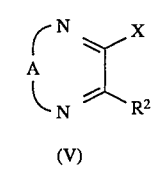

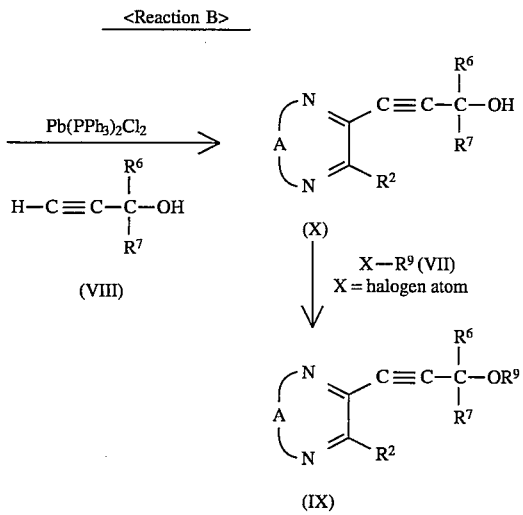

That is, a process for the production of a compound represented by the aforementioned formula (I) or a salt thereof which comprises allowing a compound, a monohalogenated aryl or a dihalogenated aryl compound, represented by the following formula (V)

wherein A is a group represented by the following formula (II)

or the following formula (III);

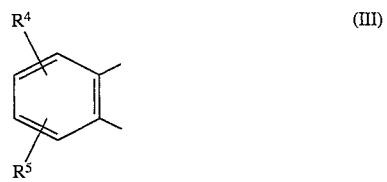

X represents a halogen atom; $R^2$ represents a hydrogen atom, a methoxy group, a halogen atom, an amino group which may be substituted with 1 or 2 alkyl groups having 1 or 2 carbon atoms, a trifluoromethyl group, a straight- or branched-chain alkyl group having 1 to 6 carbon atoms, an alkoxycarbonyl group having 1 or 2 carbon atoms, a methylthio group, a methylsulfinyl group, a methylsulfonyl group or a group represented by the following formula (IV);

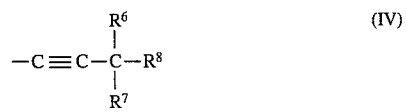

$R^6$ represents a hydrogen atom, a straight- or branched-chain or cyclic alkyl group having 1 to 6 carbon atoms or an alkoxy group having 1 or 2 carbon atoms; $R^7$ represents a hydrogen atom or an alkyl group having 1 or 2 carbon atoms, $R^6$ and $R^7$ together with their adjoining carbon atom may form a cycloalkylidene group having 3 to 6 carbon atoms or $R^6$, $R^7$ and $R^8$ together with their adjoining carbon atom may form a cycloalkyl group having 3 to 6 carbon atoms; $R^8$ represents a hydrogen atom, a straight- or branched-chain alkyl group having 1 to 3 carbon atoms which may be substituted with a group selected from an alkoxy group having 1 or 2 carbon atoms and an alkylthio group having 1 or 2 carbon atoms, an alkenyloxy group having 2 to 4 carbon atoms, a straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms, a carbamoyloxy group, an acetoxy group or a methylthio group; $R^3$ represents an alkoxycarbonyl group having 1 or 2 carbon atoms, a cyano group, a carboxyl group or a carbamoyl group; $R^4$ represents a hydrogen atom or a methoxy group; and $R^5$ represents a hydrogen atom, a methoxy group, a halogen atom, a methoxycarbonyl group, a methyl group, a hydroxymethyl group, a methoxymethyl group, a carbamoyl group, a bis(ethoxycarbonyl)acetyl group, an acetyl group, a 1-hydroxyiminoethyl group, a 1-methoxyiminoethyl group, a formyl group or a cyano group, to react with a compound represented by the following formula (VI)

$$M-R^1 \quad (VI)$$

wherein M represents a hydrogen atom, a lithium atom, a magnesium atom, a mercury atom, a zinc atom, a copper atom or a boron, aluminum, silicon or tin atom which may be substituted with one or more alkyl groups having 1 to 4 carbon atoms and $R^1$ is a group represented by the aforementioned formula (IV), namely a 1-alkyne derivative or a metal acetylide thereof, in the presence or absence of a metal catalyst such as a zero valent palladium complex, a palladium(II) complex or the like palladium catalyst, a copper catalyst or a nickel catalyst.

According to a third aspect of the present invention, there is provided a pharmaceutical composition which contains a compound represented by the aforementioned formula (I) or a salt thereof as an active ingredient.

In the case of a combination of $R^1$ $R^2$ and $R^8$ when $R^1$ is represented by the formula (IV), it is preferable that $R^1$ and $R^2$ are the same group and $R^8$ is a straight- or branched-chain alkyl group having 1 to 3 carbon atoms which is substituted with an alkoxy group having 1 or 2 carbon atoms or a straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms.

In addition to this combination, when A of the formula (I) is a group represented by the formula (II), it is preferable that $R^3$ is an alkoxycarbonyl group having 1 or 2 carbon atoms.

Also, when A of the formula (I) is a group represented by the formula (III), it is preferable that $R^4$ is a hydrogen atom, $R^5$ is a hydrogen atom or a methoxy, hydroxymethyl or acetyl group at the 6-position and $R^7$ is an alkyl group having 1 or 2 carbon atoms.

According to a fourth aspect of the present invention, there is provided a drug for use in the prevention and/or treatment of peptic ulcers which contains a compound represented by the aforementioned formula (I) or a salt thereof as an active ingredient.

According to a fifth aspect of the present invention, there is provided a gastric acid secretion inhibitor which contains a compound represented by the aforementioned formula (I) or a salt thereof as an active ingredient.

Other objects and advantages of the present invention will be made apparent as the description progresses.

DETAILED DESCRIPTION OF THE INVENTION

Figure 1:
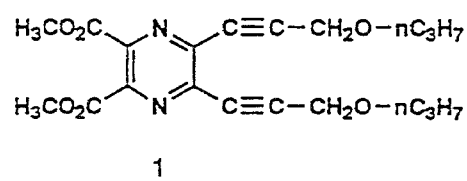
FIG. 1 is a drawing showing structural formulas of compounds 1 to 8 of the present invention.
Figure 1:
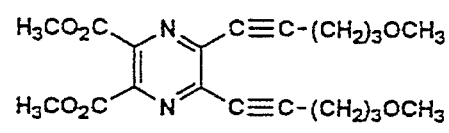
Figure 1:
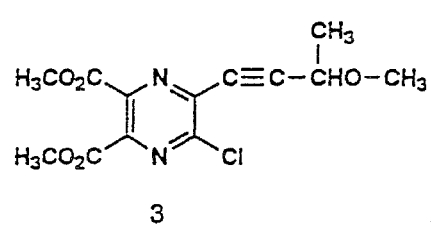
Figure 1:
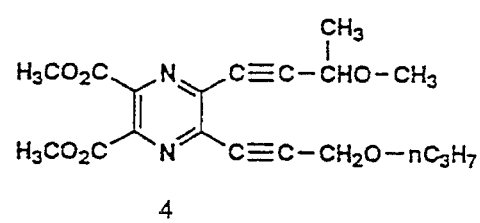
Figure 1:
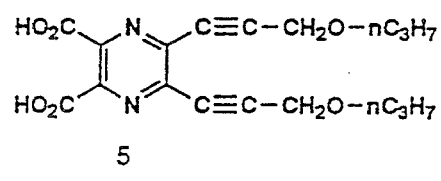
Figure 1:
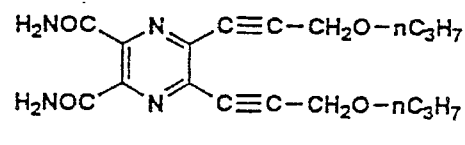
Figure 1:
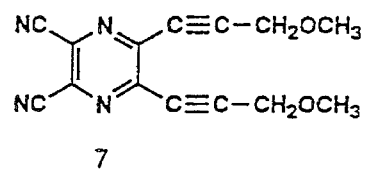
Figure 1:
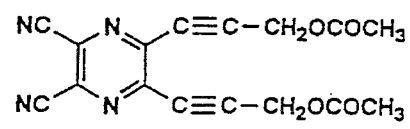

In the compound of the following formula (I), $R^1$ is a group represented by the following formula(IV) wherein $R^6$ represents a hydrogen atom, a straight- or branched-chain or cyclic alkyl group having 1 to 6 carbon atoms or an alkoxy group having 1 or 2 carbon atoms; $R^7$ represents a hydrogen atom or an alkyl group having 1 or 2 carbon atoms, $R^6$ and $R^7$ together with their adjoining carbon atom may form a cycloalkylidene group having 3 to 6 carbon atoms or $R^6$, $R^7$ and $R^8$ together with their adjoining carbon atom may form a cycloalkyl group having 3 to 6 carbon atoms; $R^8$ represents a hydrogen atom, a straight- or branched-chain alkyl group having 1 to 3 carbon atoms which may be substituted with a group selected from an alkoxy group having 1 or 2 carbon atoms and an alkylthio group having 1 or 2 carbon atoms, an alkenyloxy group having 2 to 4 carbon atoms, a straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms, a carbamoyloxy group, an acetoxy group or a methylthio group.

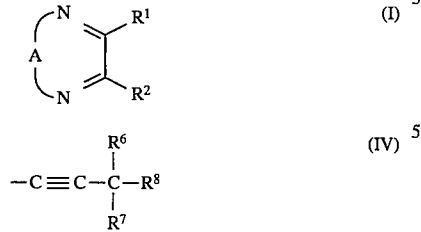

Preferred examples of $R^6$ include a hydrogen atom, a straight- or branched-chain or cyclic alkyl group having 1 to 6 carbon atoms or an alkoxy group having 1 or 2 carbon atoms. Illustrative examples of the straight- or branched-chain or cyclic alkyl group having 1 to 6 carbon atoms include methyl, ethyl, n-propyl, i-propyl, n-hexyl, cyclopropyl, cyclobutyl, cyclopentyl and cyclohexyl; and those of the alkoxy group having 1 or 2 carbon atoms include methoxy.

Most preferably, $R^6$ may be a hydrogen atom, methyl or ethyl.

Preferred examples of $R^7$ include a hydrogen atom and an alkyl group having 1 or 2 carbon atoms and more preferably methyl or ethyl.

When $R^6$ and $R^7$ together with their adjoining carbon atom form a cycloalkylidene group having 3 to 6 carbon atoms, $R^6$ and $R^7$ represent such group as cyclopropylidene, cyclobutylidene, cyclopentylidene or cyclohexylidene, preferably cyclopropylidene, cyclobutylidene or cyclopentylidene.

When $R^6$, $R^7$ and $R^8$ together with their adjoining carbon atom form a cycloalkyl group having 3 to 6 carbon atoms, $R^6$ and $R^7$ represent such group as cyclopropyl, cyclobutyl, cyclopentyl or cyclohexyl, preferably cyclopropyl, cyclobutyl or cyclopentyl.

Preferred examples of $R^8$ include a hydrogen atom; a carbamoyloxy group; a acetoxy group; a methylthio group; a straight- or branched-chain alkyl group having 1 to 3 carbon atoms which may be substituted with a group selected from an alkoxy group having 1 or 2 carbon atoms and an alkylthio group having 1 or 2 carbon atoms; an alkenyloxy group having 2 to 4 carbon atoms; and a straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms.

Preferred examples of the straight- or branched-chain alkyl group having 1 to 3 carbon atoms which may be substituted with a group selected from an alkoxy group having 1 or 2 carbon atoms and an alkylthio group having 1 or 2 carbon atoms include methyl, methoxymethyl, ethoxymethyl, 2-methoxyethyl, 3-methoxy-1-propyl and methylthiomethyl. Preferred examples of the alkenyloxy group having 2 to 4 carbon atoms include 2-propenyloxy. Preferred examples of the straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms include methoxy, ethoxy, n-propoxy, i-propoxy, n-butoxy, 2-methoxyethoxy, 2-ethoxyethoxy, 2-n-propoxyethoxy, 2-i-propoxyethoxy, 2-methoxycarbonylethoxy and 2-ethoxycarbonylethoxy.

In consequence, preferred examples of the group represented by $R^1$ include 1-propynyl, 1-butynyl, 1-pentynyl, 3-methyl-1-butynyl, 1-hexynyl, 2-cyclopropyl-1-ethynyl, 3,3-dimethyl-1-butynyl, 3,3-dimethoxy-1-propynyl, 3-methoxy-1-propynyl, 3-methoxy-1-butynyl, 3-methoxy-1-pentynyl, 3-methoxy-3-methyl-1-butynyl, 3-ethoxy-1-propynyl, 3-ethoxy-1-butynyl, 3-ethoxy-1-pentynyl, 3-ethoxy-3-methyl-1-butynyl, 3-(2-methoxyethoxy)-1-propynyl, 3-(2-methoxyethoxy)-1-butynyl, 3-(2-methoxyethoxy)-1-pentynyl, 3-(2-methoxyethoxy)-3-methyl-1-butynyl, 3-(2-ethoxyethoxy)-1-propynyl, 3-(2-ethoxyethoxy)-1-butynyl, 3-(2-ethoxyethoxy)-1-pentynyl, 3-(2-ethoxyethoxy)-3-methyl-1-butynyl, 3-(2-n-propoxyethoxy)-1-butynyl, 3-(2-n-propoxyethoxy)-3-methyl-1-butynyl, 3-(2-n-propoxyethoxy)-1-pentynyl, 3-(2-i-propoxyethoxy)-1-butynyl, 3-(2-i-propoxyethoxy)-3-methyl-1-butynyl, 3-(2-i-propoxyethoxy)-1-pentynyl, 3-(2-methoxycarbonylethoxy)-1-pentynyl, 3-(2ethoxyethoxy)-3-methyl-1-pentynyl, 3-(2-ethoxyethoxy)-3-ethyl-1-pentynyl, 3-n-propoxy-1-propynyl, 3-n-propoxy-1-butynyl, 3-i-propoxy-1-propynyl, 3-n-butoxy-1-propynyl, 3-(2propenoxy)-1-propynyl, 3-(2-ethoxyethoxy)-1-hexynyl, 4-methoxy-1- butynyl, 4-ethoxy-1-butynyl, 5-methoxy-1-pentynyl, 6-methoxy-1-hexynyl, 3-thiomethyl-1-propynyl, 4-thiomethyl-1-butynyl, 3-acetoxy-1-propynyl, 3-carbamoyloxy-1-propynyl, 2-(1-methoxycyclopentyl)ethynyl, 2-(1-(2-methoxyethoxy)cyclobutyl)ethynyl, 2-(1-(2-ethoxyethoxy)cyclobutyl)ethynyl and the like groups.

When A in the formula (I) is represented by the formula (II), as concerning to $R^6$, $R^7$ and $R^8$ it is preferable that $R^6$ is a hydrogen atom, methyl or ethyl, more preferably a hydrogen atom, $R^7$ is a hydrogen atom, methyl or ethyl and $R^8$ is methoxymethyl, 2-methoxyethyl, methoxy, ethoxy, n-propoxy, i-propoxy, n-butoxy or 2-methoxyethoxy, more preferably 2-methoxyethyl or n-propoxy. Illustrative preferred examples of the group represented by $R^1$ include 3-methoxy-1-propynyl, 3-methoxy-1-butynyl, 3-methoxy-1-pentynyl, 3-methoxy-3-methyl-1-butynyl, 3-ethoxy-1-propynyl, 3-ethoxy-1-butynyl, 3-(2-methoxyethoxy)-1-propynyl, 3-(2-methoxyethoxy)-1-butynyl, 3-n-propoxy-1-propynyl, 3-n-propoxy-1-butynyl, 3-i-propoxy-1-propynyl, 3-n-butoxy-1-propynyl, 4-methoxy-1-butynyl, 5-methoxy-1-pentynyl and the like groups, of which 3-n-propoxy-1-propynyl or 5-methoxy-1-pentynyl is particularly preferred.

When A in the formula (I) is represented by the formula (III) as concerning to $R^6$, $R^7$ and $R^8$ it is preferable that $R^6$ is a hydrogen atom, methyl, ethyl or n-propyl, $R^7$ is a hydrogen atom, methyl or ethyl, more preferably methyl, ethyl, and $R^8$ is methoxymethyl, 2-methoxyethyl, methoxy, ethoxy, n-propoxy, i-propoxy, n-butoxy, 2-methoxyethoxy, 2-ethoxyethoxy, 2-n-propoxyethoxy or 2-i-propoxyethoxy, more preferably 2-methoxyethoxy or 2-ethoxyethoxy.

Illustrative preferred examples of the group represented by $R^1$ include 3-methoxy-1-propynyl, 3-methoxy-1-butynyl, 3-methoxy-1-pentynyl, 3-methoxy-3-methyl-1-butynyl, 3-ethoxy-1-propynyl, 3-ethoxy-1-butynyl, 3-ethoxy-1-pentynyl, 3-ethoxy-3-methyl-1-butynyl, 3-(2-methoxyethoxy)-1-propynyl, 3-(2-methoxyethoxy)-1-butynyl, 3-(2-methoxyethoxy)-1-pentynyl, 3-(2-methoxyethoxy)-3-methyl-1-butynyl, 3-(2-ethoxyethoxy)-1-butynyl, 3-(2-ethoxyethoxy)-1-pentynyl, 3-(2-ethoxyethoxy)-3-methyl-1-butynyl, 3-n-propoxy-1-propynyl, 3-n-propoxy-1-butynyl, 3-i-propoxy-1-propynyl, 3-n-butoxy-1-propynyl, 4-methoxy-1-butynyl, 5-methoxy-1-pentynyl, 3-(2-n-propoxyethoxy)-1-pentynyl, 3-(2-i-propoxyethoxy)-1-pentynyl, 3-(2-ethoxyethoxy)-3-methyl-1-pentynyl, 3-(2-ethoxyethoxy)-3-ethyl-1-pentynyl, 3-(2-ethoxyethoxy)-1-hexynyl, 3-(2-n-propoxyethoxy)-3-methyl-1-butynyl, 3-(2-i-propoxyethoxy)-3-methyl-1-butynyl and the like groups, of which 3-(2-methoxyethoxy)-1-pentynyl, 3-(2-methoxyethoxy)-3-methyl-1-butynyl, 3-(2-ethoxyethoxy)-1-pentynyl, 3-(2-ethoxyethoxy)-3-methyl-1-butynyl, 3-(2-ethoxyethoxy)-3-methyl-1-pentynyl, 3-(2-ethoxyethoxy)-3-ethyl-1-pentynyl and the like are particularly preferred.

In the compound of formula (I), $R^2$ is a hydrogen atom, a methoxy group, a halogen atom, an amino group which may be substituted with 1 or 2 alkyl groups having 1 or 2 carbon atoms, a trifluoromethyl group, a straight- or branched-chain alkyl group having 1 to 6 carbon atoms, an alkoxycarbonyl group having 1 or 2 carbon atoms, a methylthio group, a methylsulfinyl group, a methylsulfonyl group or a group shown in the foregoing as $R^1$, wherein $R^1$ and $R^2$ may be the same or different from each other. When $R^2$ is a hydrogen atom, the compound of formula (I) does not have a substituent group at the same position. Preferred examples of $R^2$ include a hydrogen atom, methoxy group, methyl group, ethyl group, n-hexyl group, methoxycarbonyl group, ethoxycarbonyl group, fluorine atom, chlorine atom, bromine atom, amino group, N,N-dimethylamino group, N,N-ethylmethylamino group, N,N-diethylamino group, trifluoromethyl group, methylthio group, methylsulfinyl group, methylsulfonyl group and the same group of $R^1$, and more preferably the same group of $R^1$. When A in the compound represented by formula (I) is the formula (II) or (III), it is more preferable that $R^2$ is the same group of $R^1$ in each case.

When A in the compound represented by formula (I) is the formula (II), $R^3$ represents an alkoxycarbonyl group having 1 or 2 carbon atoms, a cyano group, a carboxyl group or a carbamoyl group, preferably methoxycarbonyl, ethoxycarbonyl, cyano, carboxyl, carbamoyl or the like group, more preferably methoxycarbonyl group.

When A in the compound represented by formula (I) is the formula (III), $R^4$ represents a hydrogen atom or a methoxy group and $R^5$ represents a hydrogen atom, a methoxy group, a halogen atom, a methoxycarbonyl group, a methyl group, a hydroxymethyl group, a methoxymethyl group, a carbamoyl group, a bis(ethoxycarbonyl)acetyl group, an acetyl group, a 1-hydroxyiminoethyl group, a 1-methoxyiminoethyl group, a formyl group or a cyano group. Illustrative example of a halogen atom of $R^5$ include fluorine atom, chlorine atom, bromine atom and iodine atom. Preferably, $R^4$ is a hydrogen atom and $R^5$ is a hydrogen atom, methoxy group, hydroxymethyl group, formyl group, acetyl group or chlorine atom. In this connection, when $R^4$ and $R^5$ are hydrogen atoms each other, the aromatic ring of formula (III) does not have substituent groups at the respective positions. When A in the compound represented by formula (I) is the formula (III), the formula (I) represents quinoxaline derivatives, and so the substituted position of $R^4$ or $R^5$ are represented at 5-position, 6-position, 7-position or 8-position.

Next, stereoisomers of the compound of the present invention are described.

When $R^1$ or $R^2$ in the formula (I) representing the compound of the present invention is represented by the formula (IV) and $R^6$, $R^7$ and $R^8$ are different from one another, the carbon atom substituted by these groups is an asymmetric carbon atom. Also, when $R^2$ is a methylsulfinyl group, its sulfur atom is an asymmetric atom. In such cases, a compound represented by the formula (I) has one or more asymmetric centers and gives various optically active forms, namely enantiomers or diastereomers. In addition, some compounds represented by the general formula (I) form optically inactive stereoisomers due to the presence of symmetry plane in the molecule.

Also, when $R^1$ and $R^2$ in the aforementioned formula (I) are represented by the formula (IV) and different from each other, isomers are present in the compound of formula (I) due to the difference in substituent groups between $R^4$ and $R^5$ or their substitution positions. In addition, cis-trans isomers exist when $R^8$ is alkenyloxy group, and syn-anti isomers are present when $R^5$ is 1-hydroxyiminoethyl or 1-methoxyiminoethyl group. All of these optically active or inactive stereoisomer forms and optional mixtures thereof are included in the present invention.

The compound of the present invention can form a salt with an inorganic or organic acid. Examples of such salts include inorganic acid salts such as hydrochloride, sulfate, nitrate and the like and organic acid salts such as acetate, oxalate, p-toluenesulfonate and the like. Depending on the type of substituent groups, the compound of the present invention can also form a salt with an inorganic or organic base. Examples of such salts include alkali metal salts such as sodium, potassium and the like salts, alkaline earth metal salts such as magnesium, calcium and the like salts, inorganic base salts such as ammonium salt and the like and organic base salts such as benzylamine salt, diethylamine salt and the like. The inventive compound can also form a solvate with water, ethanol, glycerol, acetic acid or the like solvent.

The alkyne derivative of the present invention or a salt thereof can be prepared based on the following reaction scheme.

<Reaction A>

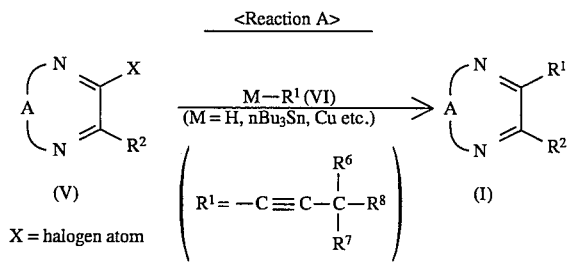

X = halogen atom

The reaction steps are described as follows.

The compound of formula (I) can be obtained by allowing a compound represented by the formula (V) to react with a compound represented by the formula (VI), namely a 1-alkyne derivative (M=H) or a metal acetylide (M=nBu$_3$Sn, Cu or the like), in the presence or absence of a metal catalyst in an atmosphere of nitrogen, argon or the like inert gas.

When $R^2$ in the formula (V) is a halogen atom, a monoalkyne derivative can be prepared as a compound represented by the formula (I) by using 1 equivalent amount of the compound of formula (VI). An asymmetric dialkyne derivative ($R^1$ and $R^2$ in the formula (I) are different from each other) can be prepared by allowing the thus obtained monoalkyne derivative to react with a reagent as a compound of the formula (VI) whose $R^1$ is different from that of the firstly used compound. Also, a dialkyne derivative can be prepared by using 2 equivalent amount of the compound of formula (VI).

The compound represented by the formula (I) can be made into a salt form by adding an acid or a base. It can also be made into a solvate by dissolving it in an appropriate solvent and treating the solution in the usual way.

When the aforementioned formula (VI) is a 1-alkyne derivative (M=H), heteroaryl halides can be allowed to react with a 1-alkyne derivative using the commonly coupling condition. That is, a heteroarylalkyne derivative can be obtained by using a coupling reaction in the presence of a palladium catalyst in accordance, for example, with the method of Ohta et al. (*Chemical Pharmaceutical Bulletin*, vol.34, pp.1447–1458, 1986) in which a chloropyrazine derivative is allowed to react with a 1-alkyne derivative or with the method of Ames et al. (*Journal of Chemical Society Perkin Transactions* 1 (to be referred to as "*J. Chem. Soc. Perkin Trans.* 1" hereinafter), pp.1384–1389, 1980).

With regard to the catalyst to be used, utility of palladium(O) as a catalyst in the reaction of organic halides with acetylene derivatives has been reported in 1975 by Cassar et al. (*Journal of Organometallic Chemistry* (to be referred to as "*J. Organometal. Chem.*" hereinafter), vol.93, pp.253–257, 1975), by Heck et al. (*J. Organometal. Chem.*, vol.93, pp.259–263, 1975) and by Sonogashira et al. (*Tetrahedron Letters* (to be referred to as "*Tetrahedron Lett.*" hereinafter), pp.4467–4470, 1975). Also useful as the catalyst is a nickel catalyst used in the reaction of alkyl aluminum with acetylene bromide reported by Giacomelli et al. (*Tetrahedron Lett.*, 2831–2834, 1978).

In general, palladium complexes having a tertiary phosphine as a ligand are used as the catalyst of such reactions. As these palladium complexes, commercially available products or zero valency palladium complexes generated in site may be used (Jikken Kagaku Koza (4th ed.), 25, Organic Synthesis VII, Synthesis by Organometallic Reagents). Also useful are palladium(II) complexes such as PdCl$_2$(PPh$_3$)$_2$, Pd(OAc)$_2$(PPh$_3$)$_2$ and the like. With regard to a tertiary phosphine ligand, triphenylphosphine is used most commonly, in addition to tri (o-tolyl)phosphine and bidentate bisphosphines such as 1,2-bis(diphenylphosphino)ethane (dppe) and 1,1'-(diphenylphosphino)ferrocene (dppf).

As the palladium catalyst for use in the coupling reaction of the present invention, the aforementioned known catalysts, preferably tetrakis(triphenylphosphine)palladium (Pd(PPh$_3$)$_4$) or bis(triphenylphosphine)palladium(II) chloride (PdCl$_2$(PPh$_3$)$_2$), may be used. Preferably, the reaction may be carried out in the coexistence of potassium acetate when Pd(PPh$_3$)$_4$ is used, or copper(I) iodide and alkyl amine when PdCl$_2$(PPh$_3$)$_2$ is used. In the coupling reaction of the present invention, copper powder or the like as the catalyst can be also be used.

In the aforementioned reaction scheme A, the amount of catalyst employed may be 0.1 to 20 mol %, preferably 0.1 to 8 mol %, per one halogen atom of the compound of formula (V).

The reaction can be carried out in an appropriate organic solvent, preferably N,N-dimethylformamide, dimethyl sulfoxide, acetonitrile, 1,3-dimethyl-2-imidazolidinone or the like. The reaction may be carried out at 0° C. to the boiling point of used solvent, preferably at room temperature to 100° C. when N,N-dimethylformamide or dimethyl sulfoxide is used, or at room temperature to the boiling point of the solvent when acetonitrile or 1,3-dimethyl-2-imidazolidinone is used.

When the formula (VI) is a metal acetylide, the reaction can be carried out in accordance with the general method which is employed in coupling reaction of metal acetylides with aryl iodides (a review by Sonogashira et al. (Yuki Gosei Kagaku Kyokaishi, vol.38, pp.648–660, 1980); Negishi et al., *J. Org. Chem.*, vol.43, pp.358–360, 1978)).

It is well known that the metal acetylide coupling reaction can be applied not only to aryl halides but also to triflate compounds (Stille et al., *Journal of American Chemical Society* (to be referred to as "*J. Am. Chem. Soc.*" hereinafter), vol.108, pp.3033–3040, 1986, and vol.111, pp.5417–5424, 1989).

As an example of catalyst-free reaction, coupling reaction of cuprous acetylide with aryl iodide has been reported by Castro et al. (*J. Org. Chem.*, vol.28, p.2163, 1963, and vol.28, pp.3313–3315, 1963).

Example of metals to be used in the metal acetylide include lithium, magnesium, mercury, zinc, copper, boron, aluminum, silicon, tin and the like.

In the practice of the Preparation of the compound (I) of the present invention, each of the aforementioned metal acetylides cited in literatures, preferably tin acetylide or cuprous acetylide, may be used. When tin acetylide is used, the reaction may be carried out preferably in the presence of a catalyst selected from those used in the aforementioned coupling reaction of 1-alkyne derivatives, but either in the presence or absence of catalyst in the case of cuprous acetylide. When a catalyst is used in the coupling reaction of a metal acetylide, Pd(PPh$_3$)$_4$ may be most desirable. The amount of catalyst employed may be 0.1 to 20 mol %, preferably 0.1 to 8 mol %, per one halogen atom.

Examples of the solvent to be used in the coupling reaction include aromatic hydrocarbon solvents such as benzene, toluene and the like, ether solvents such as tetrahydrofuran, dioxane, ethylene glycol dimethyl ether and the like and polar organic solvents such as N,N-dimethylformamide, dimethyl sulfoxide, 1,3-dimethyl-2-imidazolidinone, pyridine and the like, of which an ether solvent such as tetrahydrofuran, dioxane or the like or N,N-dimethylformamide is particularly preferred. The coupling reaction may be carried out in an atmosphere of nitrogen, argon or the like inert gas, at 0° C. to the boiling point of the solvent used, preferably at the boiling point in the case of ether solvents or at room temperature when N,N-dimethylformamide is used. When cuprous acetylide is used and catalyst is not required, the reaction may be carried out preferably in pyridine, N,N-dimethylformamide or the like solvent at room temperature to the boiling point of the solvent.

As illustrative examples of 1-alkyne derivatives of the compound of formula (VI) to be used in the present invention, commercially available propyne, 1-butyne, methyl propargyl ether and the like may be used. Alternatively, a desirable 1-alkyne derivative may be obtained by allowing an corresponding commercially available alkynyl alcohol to react with an alkyl halide represented by the following formula (VII)

X—R$^9$                 (VII)

wherein X is a halogen atom and R$^9$ is an alkyl group having 1 to 4 carbon atoms which may be substituted with a group selected from a straight- or branched-chain alkoxy group having 1 to 3 carbon atoms and an alkoxycarbonyl group having 1 or 2 carbon atoms, in the presence of an inorganic base such as sodium hydride, potassium hydroxide or the like or an organic base such as triethylamine, 1,8-diazabicyclo[5,4,0]undeca-7-ene, in accordance with a known method such as of Jackson et al. (Australian Journal of Chemistry (to be referred to as "Aust. J. Chem." hereinafter), vol.41, pp.251–261, 1988) or of Vartanyan et al. (Armyanskii Khimicheskii Zhurnal, vol.27, pp.295–303, 1974).

The tin acetylide to be used in the present invention can be obtained by allowing a desired 1-alkyne derivative to react with n-butyllithium in anhydrous ether such as diethyl ether, tetrahydrofuran or the like and then with tri-n-butyltin chloride. The cuprous acetylide can be obtained as yellow crystals by adding ethanol and a desired 1-alkyne derivative to the aqueous ammonia solution (28%) of copper(I) iodide. The cuprous acetylide can also be obtained by allowing a desired 1-alkyne derivative to react with n-butyllithium in anhydrous ether such as diethyl ether, tetrahydrofuran or the like and then with copper(I) iodide.

The compound of formula (V) to be used as a starting material can be obtained commercially or synthesized easily in accordance with the methods reported in the following literatures.

Examples of such synthesized products include 5,6-dichloropyrazine-2,3-dicarboxylic acid methyl ester (Elina et al., Khimiya Geterotsiklicheskikh Soedinenii (to be referred to as "Khim. Geterotsikl. Soedin." hereinafter), pp.1548–1551, 1973); 2,3-dichloro-5,6-dicyanopyrazine (Suzuki et al., *Journal of Heterocyclic Chemistry* (to be referred to as "J. Heterocyclic Chem." hereinafter), vol.23, pp.1419–1421, 1986); 2,3-dicyano-5-chloro-6-methylpyrazine (JP-A 55-164607 (the term "JP-A" as used herein means an "unexamined published Japanese patent application")); 2-amino-3-chloro-5,6-dicyanopyrazine (Suzuki et al. , J. Heterocyclic Chem. , vol.23, pp.1741–1746, 1986); 2,3-dicyano-5-chloro-6-(methylthio)pyrazine (JP-A 55-167206); 2-oxy-3-ethoxycarbonyl-5,6-dicyanopyrazine (JP-A 51-34175); 6-methoxy-2,3-dicycloquinoxaline (JP-A 62-72678); 2,3-dichloro-6-(bis(ethoxycarbonyl)acetyl)quinoxaline obtained by allowing to react of 2,3-dichloroquinoxaline-6-carbonyl chloride (JP-A 57-98274 (Inventive Example 1)) with diethylmagnesium malonate which is prepared in accordance with the method of Chapman et al. (Journal of Chemical Society (to be referred to as "J. Chem. Soc." hereinafter), (C), pp.2747–2751, 1968), as well as its decarboxylation product 6-acetyl-2,3-dichloroquinoxaline; and 2,3-diiodoquinoxaline obtained from 2,3-dichloroquinoxaline in accordance with the method of Iijima et al. (Yakugaku Zasshi, vol.108, pp.437–442, 1988). As occasion demands, functional groups of these compounds may be reduced or oxidized in the usual way.

As described in the foregoing, the compound of the present invention contains various stereoisomers, and isolation of each of these stereoisomers can be made easily by those skilled in the art in the light of various text books such as "Fusei-gosei to kagaku-bunkatsu no shinpo (Advance in Asymmetric Synthesis and Optical Resolution)" (edited by Ohtsuka and Mukaiyama, Kagaku Zokan 97, published by Kagaku Dojin Shuppan, 1982) and "Kou-sentakuteki hannou (Highly Selective Reactions)" edited by Nozaki, Mukaiyama and Noyori, Kagaku Zokan 91, published by Kagaku Dojin Shuppan, 1981).

When the compound of formula (VI) to be used in the coupling reaction has an asymmetric carbon atom, the compound of formula (I) obtained therefrom contains optically active substances or diastereomers. When the compound of formula (I) is obtained as a mixture thereof through the synthesis steps, each of these isomers can be isolated by the use of an optical resolution column such as CHIRALCEL AD™ (hexane/ethanol system) manufactured by Daicel.

As described in the foregoing, when R$^1$ and R$^2$ in the formula (I) are represented by the formula (IV) and different from each other, isomers are present in the compound of formula (I) due to the difference in substituent groups between R$^4$ and R$^5$ or their substitution positions. Also, syn-anti isomers are present when R$^5$ is 1-hydroxyiminoethyl or 1-methoxyiminoethyl group. When the compound of formula (I) is obtained as a mixture of such isomers or syn-anti isomers through the synthesis steps, each of these isomers can be isolated by the use of a silica gel column chromatography.

In addition, when the compound of formula (VI) is a 1-alkyne derivative or a metal acetylide thereof obtained in accordance with a known method by allowing a corresponding alkynyl alcohol represented by the following formula (VIII),

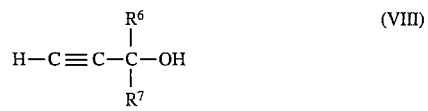

wherein R$^6$ represents a hydrogen atom or a straight- or branched-chain or cyclic alkyl group having 1 to 6 carbon atoms and R$^7$ represents a hydrogen atom or an alkyl group having 1 or 2 carbon atoms, to react with an alkyl halide represented by the formula (VII) wherein X is a halogen atom and R$^9$ represents an alkyl group having 1 to 4 carbon atoms which may be substituted with a group selected from a straight- or branched chain alkoxy group having 1 to 3 carbon atoms and an alkoxycarbonyl group having 1 or 2 carbon atoms, each isomer of the compound (I) can be obtained by the use of a corresponding optically active substance of the alkynyl alcohol.

Optically active substances of the alkynyl alcohol represented by the formula (VIII) can be obtained by various means, such as the method of Smith et al. in which a diastereomer salt prepared from phthalic acid ester of a racemic alcohol with an optically active amine is subjected to resolution (*Journal of Medicinal Chemistry* (to be referred to as "*J. Med. Chem.*" hereinafter), vol.31, 1558–1566, 1988); a method in which an inclusion compound is formed by allowing a racemic alcohol to react with brucine and then subjected to optical resolution (JP-A 62-246530); the method of Henderson et al. in which a diastereomeric carbamate or ester prepared from a racemic alcohol is separated to obtain an optically active alcohol (*J. Org. Chem.*, vol.53, pp.4736–4745, 1988); the method of Mori et al. in which acetate of a racemic alcohol is hydrolyzed using a bacterium to obtain an active alcohol (*Tetrahedron Lett.*, pp.4127–4130, 1978); the method of Amici et al. in which an optically active alcohol is obtained from its corresponding alkynyl ketone by an enzymatic asymmetric reduction (*J. Org. Chem.*, vol.54, pp.2646–2650, 1989); the method of Midland et al. (*J. Am. Chem. Soc.*, vol.102, pp.867–869, 1980) or of Noyori et al. (*J. Am. Chem. Soc.*, vol.106, pp.6717–6725, 1984) in which the asymmetric reduction reaction is carried out using an asymmetric ligand; and the method of Mukaiyama et al. in which an optically active alkynyl alcohol is obtained by asymmetric alkynylation of an aldehyde (*Chemistry Letters* (to be referred to as "*Chem. Lett.*" hereinafter), pp. 447–448, 1979). It is known also that an optically active alkynyl alcohol can be obtained by the method of Ito et al. which uses 1,2-dehydroiodination reaction of an optically active γ-iodoallylic alcohol obtained by Sharpless kinetic resolution (Tetrahedron Lett., vol.30, pp.7083–7086, 1989).

Optically active substances of the compound of formula (VIII) can be obtained in accordance with the aforementioned methods. In consequence, the use of the thus obtained optically active compound of formula (VIII) makes possible to prepare various optically active forms of the compound of formula (I), namely enantiomers or diastereomers, and its stereoisomers which become optically inactive due to the presence of symmetry plane in the molecule.

In the compound of formula (I), when $R^8$ in the $R^1$ represented by the formula (IV) is an alkoxy group having 1 to 4 carbon atoms which may be substituted with a group selected from a straight- or branched-chain alkoxy group having 1 to 3 carbon atoms and an alkoxycarbonyl group having 1 or 2 carbon atoms, the compound can be represented by the following formula (IX)

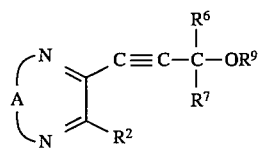

wherein A is a group represented by the following formula (II)

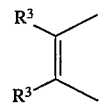

or the following formula (III);

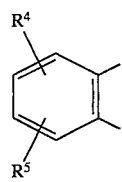

$R^2$ represents a hydrogen atom, a methoxy group, a halogen atom, an amino group which may be substituted with 1 or 2 alkyl groups having 1 or 2 carbon atoms, a trifluoromethyl group, a straight- or branched-chain alkyl group having 1 to 6 carbon atoms, an alkoxycarbonyl group having 1 or 2 carbon atoms, a methylthio group, a methylsulfinyl group, methylsulfonyl group or a group represented by the following formula (IV);

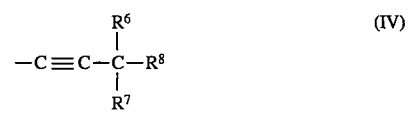

$R^6$ represents a hydrogen atom, a straight- or branched-chain or cyclic alkyl group having 1 to 6 carbon atoms or an alkoxy group having 1 or 2 carbon atoms; $R^7$ represents a hydrogen atom or an alkyl group having 1 or 2 carbon atoms, $R^6$ and $R^7$ together with their adjoining carbon atom may form a cycloalkylidene group having 3 to 6 carbon atoms or $R^6$, $R^7$ and $R^8$ together with their adjoining carbon atom may form a cycloalkyl group having 3 to 6 carbon atoms; $R^8$ represents a hydrogen atom, a straight- or branched-chain alkyl group having 1 to 3 carbon atoms which may be substituted with a group selected from an alkoxy group having 1 or 2 carbon atoms and an alkylthio group having 1 or 2 carbon atoms, an alkenyloxy group having 2 to 4 carbon atoms, a straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms, a carbamoyloxy group, an acetoxy group or a methylthio group; $R^9$ represents an alkyl group having 1 to 4 carbon atoms which may be substituted with a group selected from a straight- or branched-chain alkoxy group having 1 to 3 carbon atoms and an alkoxycarbonyl group having 1 or 2 carbon atoms; $R^3$ represents an alkoxycarbonyl group having 1 or 2 carbon atoms, a cyano group, a carboxyl group or a carbamoyl group; $R^4$ represents a hydrogen atom or a methoxy group; and $R^5$ represents a hydrogen atom, a methoxy group, a halogen atom, a methoxycarbonyl group, a methyl group, a hydroxymethyl group, a methoxymethyl group, a carbamoyl group, a bis(ethoxycarbonyl)acetyl group, an acetyl group, a 1-hydroxyiminoethyl group, a 1-methoxyiminoethyl group, a formyl group or a cyano group.

The compound of formula (IX) can also be prepared by the following alternative method.

<Reaction B>

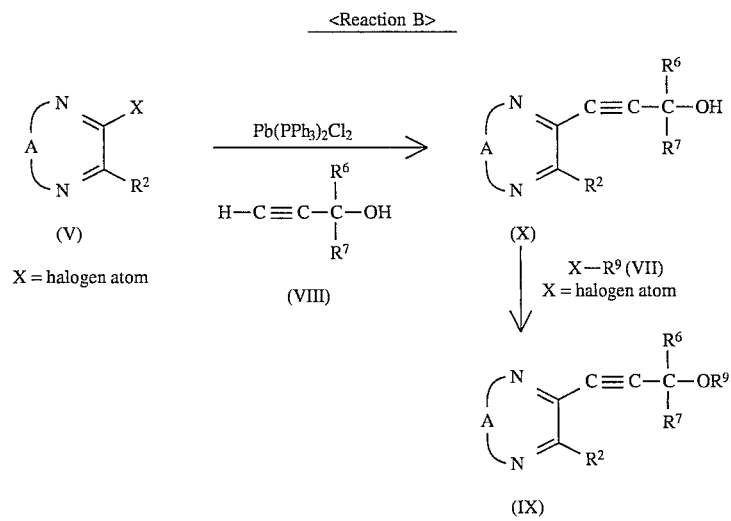

That is, the compound of formula (IX) can be obtained by allowing a compound represented by the formula (X), which is obtained by a coupling reaction of a compound of formula (V) and with a compound of formula (VIII) in the same manner as described in the foregoing, to react with an alkyl halide represented by the formula (VII) wherein X is a halogen atom and $R^9$ represents an alkyl group having 1 to 4 carbon atoms which may be substituted with a group selected from a straight- or branched-chain alkoxy group having 1 to 3 carbon atoms and an alkoxycarbonyl group having 1 to 2 carbon atoms.

When $R^2$ in the formula (V) is a halogen atom, a monoalkyne or dialkyne derivative can be prepared as the compound of formula (X) by using the compound of formula (VIII) with 1 or 2 equivalents amount, similar to the case of the reaction scheme A.

The compound of formula (IX) can also be obtained by allowing a dialkynyl alcohol derivative, in which 2 molecules of the alkynyl alcohol represented by the formula (VIII) are introduced, to react with the alkyl halide of formula (VII) wherein X is a halogen atom and $R^9$ represents an alkyl group having 1 to 4 carbon atoms which may be substituted with a group selected from a straight- or branched-chain alkoxy group having 1 to 3 carbon atoms and an alkoxycarbonyl group having 1 or 2 carbon atoms.

In the alkyl halide of formula (VII), X is preferably an iodine atom. The reaction with the compound of formula (X) should be carried out in the presence of an inorganic base such as sodium hydride, potassium hydroxide or the like, an organic base such as triethylamine, 1,8-diazabicyclo[5,4,0]undeca-7-ene or the like or silver oxide or the like. Solvents which can be used in this reaction include aromatic hydrocarbon solvents such as benzene, toluene and the like, ether solvents such as tetrahydrofuran, dioxane, ethylene glycol dimethyl ether and the like and polar organic solvents such as N,N-dimethylformamide, dimethyl sulfoxide, 1,3-dimethyl-2-imidazolidinone and the like, of which dimethyl sulfoxide, N,N-dimethylformamide and tetrahydrofuran are particularly preferred. The reaction may be carried out at −20° to 100° C., preferably at 0° to 40° C. when dimethyl sulfoxide or N,N-dimethylformamide is used or at room temperature to the boiling pint of solvent when tetrahydrofuran is used.

Next, effects of the compound of the present invention and the pharmaceutical composition of the present invention are described in detail. Pharmacological effects, toxicities and the like of typical compounds are shown in the following test examples by way of illustration and not by way of limitation.

(Test Example 1) $H^+,K^+$ Adenosine triphosphatase inhibition

Proton pump inhibition was evaluated by the $H^+,K^+$ adenosine triphosphatase (to be referred to as "$H^+,K^+$ ATPase" hereinafter) inhibition.

This test was carried out basically according to the method of Keeling et al. (*Biochemical Pharmacology*, vol.34, pp.2967–2973, 1985). That is, hog stomach was homogenized and subjected to ultracentrifugation to obtain a microsome fraction, and the microsomes were subjected to discontinuous density gradient ultracentrifugation using 0 and 9% Ficoll solutions to obtain a fraction containing $H^+,K^+$ ATPase. The $H^+,K^+$ ATPase activity was determined by measuring the released inorganic phosphorus using ATP as the substrate and an inorganic phosphorus measuring reagent PiSET(IATRON) manufactured by IATRON. The compounds shown in Examples which will be described later were used as test compounds, and the concentration of each test compound required to inhibit 50% of the enzyme activity ($IC_{50}$ value) was calculated. The results are shown in Table 1.

TABLE 1

| Compound (Ex. No.) | Enzyme inhibition $IC_{50}$ value (μg/ml) |
| --- | --- |
| 1 | 34 |
| 7 | 0.5 |
| 10 | 31 |
| 11 | 9.8 |
| 12 | 82 |
| 13 | 11 |
| 18 | 51 |
| 21 | 42 |
| 22 | 13 |
| 23 | 24 |
| 25 | 15 |
| 26 | 12 |
| 29 | 56 |
| 30 | 18 |
| 33 | 3.6 |
| 44 | 39 |
| 53 | 1.9 |
| 56 | 6.0 |
| 59 | 3.5 |

TABLE 1-continued

| Compound (Ex. No.) | Enzyme inhibition IC$_{50}$ value (µg/ml) |
| --- | --- |
| 62 | 1.7 |
| 73 | 0.5 |
| 77 | 0.4 |
| 81 | 0.4 |
| 89 | 0.1 |
| 95 | 0.2 |
| 101 | 1.5 |
| 102 | 1.1 |
| 111 | 2.7 |
| 114 | 30 |
| 116 | 77 |
| 117 | 54 |
| 119 | 5.2 |
| 123 | 41 |
| 127 | 88 |
| 129 | 8.9 |
| 133 | 8.0 |
| 138 | 4.7 |
| 140 | 12 |
| 144 | 12 |
| 145 | 9.6 |
| 151 | 8.7 |
| 158 | 8.0 |
| 159 | 7.9 |

As shown in Table 1, all of the tested compounds showed H$^+$,K$^+$ ATPase inhibition activity, namely proton pump inhibition activity.

(Test Example 2) Gastric acid secretion inhibition activity

Basically according to the method of Satoh et (*Journal of Pharmacology and Experimental Therapeutics*, vol.248, pp.806–815, 1988), each of the compounds shown in Examples was orally administered at a dose of 30 mg/kg to Sprague-Dawley (SD) male rats which have been subjected to fasting of 24 hours (free drinking).

After 3 hours of the compound administration, the pylorus of each rat was ligated under urethane anesthesia, and 30 mg of histamine hydrochloride per Kg was administered to the rat by subcutaneous injection. After 3 hours of the ligation, the gastric juice was collected to measure its volume and calculate total acidity (mEqH$^+$/3 hours) by sodium hydroxide titration. The inhibition rate (%) was calculated by the following formula in which A represents the total gastric juice acidity of control group rat and B represents the total gastric juice acidity of test compound-administered group rat.

$$\text{Inhibition rate (\%)} = \frac{A - B}{A} \times 100$$

The results are shown in Table 2.

TABLE 2

| Compound of Examples | Acid secretion inhibition rate (%) |
| --- | --- |
| 1 | 50 |
| 2 | 66 |
| 5 | 61 |
| 10 | 38 |
| 11 | 27 |
| 12 | 41 |
| 19 | 28 |
| 33 | 23 |
| 56 | 80 |
| 59 | 79 |
| 62 | 69 |
| 69 | 70 |

TABLE 2-continued

| Compound of Examples | Acid secretion inhibition rate (%) |
| --- | --- |
| 77 | 55 |
| 81 | 61 |
| 114 | 30 |
| 116 | 32 |
| 117 | 35 |
| 133 | 44 |

As shown in Table 2, each of the tested compounds showed marked effect to inhibit secretion of gastric acid.

(Test Example 3) Stress ulcer

Basically according to the method of Takagi et al. (*Japanese Journal of Pharmacology* (to be referred to as "Japan. J. Pharmacol." hereinafter), vol.18, pp.9–18, each of the compounds shown in Examples was orally administered to Wistar male rats which have been subjected to fasting of 24 hours (free drinking). Each rat was transferred into a stress cage 30 minutes thereafter and subjected to stress loading by suspending the cage in a water bath controlled at 23° C. to such a depth that the rat was soaked up to its breast.

After 7 hours of the stress loading, the rat was recovered from the water bath to excise the stomach. The length (mm) of each ulcer developed in the stomach was measured under a stereoscopic microscope, and the total length of ulcers per one animal was used as an ulcer index. The dose of each test compound required to inhibit 50% of the ulcer index of the control group was calculated (ED$_{50}$). The results are shown in Table 3, together with the results of the following pylorus ligation ulcer test.

(Test Example 4) Pylorus ligation ulcer

Basically according to the method of Shay et al. (*Gastroenterology*, vol.5, pp.43–61, 1945), each of the compounds shown in Examples was orally administered to Wistar male rats which have been subjected to fasting of 48 hours (free drinking). After 30 minutes of the compound administration, the pylorus of each rat was ligated.

After 14 hours of standing, the stomach was excised. The length and width of each ulcer developed in the forestomach part were measured under a stereoscopic microscope to calculate the ulcer area (length×width). In accordance with the method of Takagi et al. (*Japan. J. Pharmacol.*, vol.24, pp.357–361, 1974), ulcer index was calculated based on the total ulcer area per animal. The dose of each test compound required to inhibit 50% of the ulcer index of the control group was calculated (ED$_{50}$). The results are shown in Table 3.

TABLE 3

| Compound of Examples | Antiulcer activity (ED$_{50}$ value, mg/kg) | |
| --- | --- | --- |
| | Stress ulcer | Pylorus ligation ulcer |
| 1 | — | 28 |
| 2 | 60 | 66 |
| 7 | 5.6 | 1.2 |
| 10 | 15 | 11 |
| 11 | — | 35 |
| 12 | 24 | — |
| 44 | 59 | — |
| 56 | 12 | 17 |
| 59 | 18 | 21 |
| 81 | 42 | 5.2 |
| 107 | 29 | 30 |
| 116 | 39 | — |
| 117 | 6.1 | 28 |

As shown in Table 3, each of the tested compounds showed marked antiulcer activities on stress ulcer and pylorus ligation ulcer.

(Test Example 5) Cell protection effect

Basically according to the method of Mizui and Doteuchi (*Japan. J. Pharmacol.*, vol.33, pp.939–945, 1983), each of the compounds shown in Examples was orally administered to Wistar male rats which have been subjected to fasting of 24 hours (free drinking). After 30 minutes of the compound administration, a mixture solution of 0.15N hydrochloric acid and 60% ethanol was orally administered at a dose of 5 ml/kg. After 1 hour of standing, the stomach was excised. The length (mm) of each ulcer developed in the stomach was measured under a stereoscopic microscope to calculate the total length of ulcers per animal as an ulcer index. The dose of each test compound required to inhibit 50% of the ulcer index of the control group was calculated ($ED_{50}$). The results are shown in Table 4.

TABLE 4

| Compounds of Examples | Cell protection effect $ED_{50}$ value (mg/kg) |
| --- | --- |
| 7 | 1.2 |
| 10 | 1.9 |
| 11 | 41 |
| 43 | 13 |
| 44 | 13 |
| 114 | 22 |
| 116 | 2.7 |
| 117 | 8.0 |
| 119 | 22 |
| 138 | 9.8 |

As shown in Table 4, each of the tested compounds showed marked cell protection effect.

(Test Example 6) Acute toxicity test

Each of the compounds shown in Examples was orally administered to three ICR male mice per group. During one week after the administration, mortality of the animals was observed to calculate $LD_{50}$ value. The results are shown in Table 5.

TABLE 5

| Compounds of Examples | Acute toxicity $LD_{50}$ (mg/kg) |
| --- | --- |
| 1 | >1,000 |
| 2 | >1,000 |
| 7 | >1,000 |
| 11 | >1,000 |
| 12 | >1,000 |
| 43 | >1,000 |
| 44 | >1,000 |
| 59 | >1,000 |
| 81 | >1,000 |
| 108 | >1,000 |
| 113 | >1,000 |
| 114 | >1,000 |
| 115 | >1,000 |
| 116 | >1,000 |
| 117 | >1,000 |

As shown in Table 5, each of the tested compounds showed an $LD_{50}$ value of 1,000 mg/kg or more.

As is evident from the above description and test results, the compound of the present invention has a broad range of antiulcer activities, because it shows efficient function to inhibit proton pump and gastric acid secretion in various test systems. In addition, the compound of the present invention has a cell protection effect and high safety. In other words, it can be expected that the compound of the present invention shows strong acid secretion inhibition activity and mucosa protection effect in clinical or animal experimental systems and exhibits excellent effects in preventing and/or treating peptic ulcer-related diseases and in preventing relapse thereof.

The pharmaceutical composition of the present invention can be used as a drug for the prevention and/or treatment of a broad range of peptic ulcer-related diseases. Particularly, it can achieve the purpose of preventing and/or treating various diseases generally known as the indication of gastric acid secretion inhibitors or gastric mucosa protecting drugs. That is, the inventive composition is effective in preventing and/or treating gastric ulcer, duodenal ulcer, anastomotic ulcer, Zollinger-Ellison syndrome, gastritis and reflux esophagitis, as well as in treating and/or preventing morbid states of these diseases on which prior art drugs cannot show sufficient efficacy. It can also be used in NSAID (non-steroidal anti-inflammatory drug)-induced gastritis, patients of acute upper gastrointestinal bleeding and patients having past history of gastritis caused by chronic or acute alcohol taking. It is also useful for the medication prior to anesthesia.

The compound of the present invention can be administered orally or parenterally as an antiulcer drug for the prevention and/or treatment of diseases in humans and animals, and its oral administration shows higher efficacy and therefore is preferable.

The animals include all domestic and wild animals, including, without limitation, cattle, horses, swine, sheep, goats, dogs, cats, and the like.

When the compound of the present invention is used as a drug, it can be made into various dosage forms suitable for its oral administration in the usual way. For example, the compound of the present invention can be made into oral preparations (such as tablets, capsules, granules, powders, syrups and the like) as pharmaceutical preparations which are suitable for effective administration to patients, by combining the compound with optional additives such as a filler, a binder, a lubricant, a disintegrating agent, an antiseptic agent, a tonicity agent, a stabilizing agent, a dispersing agent, an antioxidant, a coloring agent, a flavoring agent, a buffer agent, a preservative, an aromatic agent, a suspending agent, an emulsifying agent and the like and generally used carriers and solvents such as sterile water, a plant oil, a physiologically acceptable solvent, a solubilizing agent and the like. When a member of the compound of the present invention is oily at ordinary temperature, it can be made into powder form by mixing it with an optional ratio of a filler which is generally used to make liquid, oily or low boiling point principal agents into powders, such as soft anhydrous silicic acid, synthetic aluminum silicate, magnesium metasilicate aluminate, calcium silicate, synthetic hydrotalcite or the like.

The compound of the present invention, when made into a drug, may be administered at a daily dose per adult of from 1 to 1,500 mg, preferably from 3 to 1,000 mg, which may be further divided into 1 to 6 doses per day. When orally administered, it may be used at a daily dose per adult of from 1 to 1,500 mg, preferably from 3 to 1,000 mg, more preferably from 10 to 500 mg, which may be further divided into 1 to 6 doses per day.

In any route of administration, the daily dose can be optionally changed depending on the age, body weight, symptoms and the like of each patient.

The compound of the present invention, when made into a drug for animals, may be administered at a daily dose per 1 Kg body weight of from 0.02 to 25 mg, preferably from 0.05 to 16.7 mg, more preferably from 0.2 to 8.3 mg, which may be further divided into 1 to 6 doses per day.

The daily dose can be optionally changed depending on the symptoms and the like of each animals.

EXAMPLES

The following examples are provided to further illustrate the compounds having an autiulcer activity of the present invention represented by the aforementioned general formula (I), salts thereof, production processes thereof and pharmaceutical preparations thereof. It is to be understood, however, that the examples are for purpose of illustration only and are not intended as a definition of the limits of the invention.

In the following examples, melting point (°C.), $^1$H-NMR or $^{13}$C-NMR spectrum ($\delta$ value, ppm), IR spectrum (cm$^{-1}$), specific rotation and the like were described as occasion demands. Unless otherwise noted, the $^1$H-NMR spectral data were measured in CDCl$_3$ at 90 MHz or 270 MHz (the mark * in Table 6 indicates 270 MHz) using TMS (tetramethylsilane) as the internal standard. The $^{13}$C-NMR spectral data were measured at 60 MHz (shown in Table 6 as "$^{13}$C-NMR (60 MHz)"). The IR spectral data were measured by the KBr tablet method in the case of crystalline compounds or by the neat method in the case of oily compounds. Unless otherwise noted, the specific rotation was calculated from the optical rotations measured at a 10 cm of path length using the D-line of a sodium lamp.

Example 1

Preparation of 5,6-bis(3-n-propoxy-1-propynyl)pyrazine-2,3-dicarboxylic acid dimethyl ester (Step 1) Preparation of 3-n-propoxy-1-propyne A 35.9 g portion of potassium hydroxide and 31.7 ml of propargyl alcohol were added to 100 ml of dimethyl sulfoxide and the mixture was stirred for 30 minutes on a water bath at 40° C. With cooling on an ice bath, 100 g of n-propyl iodide was added dropwise to the resulting mixture which was subsequently stirred for 2 hours at 40° C. After spontaneous cooling, the upper layer was separated, washed with water and brine and then dried over anhydrous sodium sulfate. Thereafter, the drying agent was removed by filtration, and the filtrate was distilled to obtain 16.6 g of 3-n-propoxy-1-propyne.

Boiling point (°C.): 102–103 (colorless oil)

NMR (90 MHz, CDCl$_3$, $\delta$, ppm): 4.14 (2H, d), 3.48 (2H, t), 2.41 (1H, t), 1.74–1.43 (2H, m), 0.94 (3H, t)

(Step 2) Preparation of tri-n-butyl-(3-n-propoxy-1-propynyl)tin

A 9.03 g portion of the compound obtained in the above step 1 was added to 140 ml of anhydrous ether and, in an atmosphere of nitrogen, cooled to −70° C. on a dry ice-acetone bath. To this solution was added dropwise 58 ml of 1.6M n-butyllithium (hexane solution) below −65° C. After stirring at the same temperature for 15 minutes, the reaction mixture was warmed to 0° C. and then cooled again below −70° C.

Next, to the resulting solution was added dropwise a solution of 25 ml of tri-n-butyltin chloride in 100 ml of anhydrous ether, and the reaction mixture was stirred at room temperature for 16 hours. The react ion solution was poured into 100 ml of ice-cold water and mixed with 200 ml of ether. The resulting ether layer was separated, washed twice with 100 ml of water and once with 100 ml of brine and then dried over anhydrous sodium sulfate. The solvent was then evaporated under a reduced pressure.

Thereafter, the resulting residue was distilled under a reduced pressure to obtain 28.4 g of tri-n-butyl-(3-n-propoxy-1-propynyl)tin.

Boiling point (°C.): 133–137 (3 mmHg; colorless oil)

NMR (90 MHz, CDCl$_3$, $\delta$, ppm): 4.15 (2H, s), 3.48 (2H, t), 1.66–1.21 (20H, m), 1.07–0.82 (12H, m)

(Step 3) Preparation of 5,6-dichloropyrazine-2,3-dicarboxylic acid dimethyl ester In accordance with the method of Elina et al. (*Khim. Geterotsikl. Soedin.*, pp.1548–1551, 1973), 16.0 g of 2,3-dichloroquinoxaline was allowed to react with 76.8 g of potassium permanganate to obtain 10.4 g of 5,6-dichloropyrazine-2,3-dicarboxylic acid. This was then methylated to obtain 9.2 g of 5,6-dichloropyrazine-2,3-dicarboxylic acid dimethyl ester.

Boiling point (°C.): 78.7–79.2

IR (KBr, cm$^{-1}$): 2962, 1756, 1735, 1523, 1442, 1373, 1260, 1208, 1181, 1101, 956

NMR (90 MHz, CDCl$_3$, $\delta$, ppm): 4.02 (6H, s)

(Step 4) Preparation of 5,6-bis(3-n-propoxy-1-propynyl)pyrazine-2,3-dicarboxylic acid dimethyl ester A 3 g portion of 5,6-dichloropyrazine-2,3-dicarboxylic acid dimethyl ester obtained in the above step 3 was mixed with 8.77 g of the compound obtained in the above step 2, 57 ml of anhydrous 1,4-dioxane and 1.05 g of Pd(PPh$_3$)$_4$, and the mixture was refluxed for 1 hour in an atmosphere of nitrogen.

The reaction solution was poured into 300 ml of ice-cold water and extracted twice with ethyl acetate (300 ml, 100 ml). The resulting organic layers were combined, mixed with 400 ml of saturated potassium fluoride aqueous solution and then stirred vigorously for 30 minutes at room temperature. Insoluble materials were removed by filtration, and the organic layer separated from the resulting filtrate was washed with brine and dried over anhydrous sodium sulfate, and the solvent was evaporated under a reduced pressure.

The resulting residue was purified by chromatography on a silica gel column (eluent, hexane/ethyl acetate) and then crystallized from hexane to obtain 1.7 g of the title compound.

Melting point (°C.): 56.1–56.8

IR (KBr, cm$^{-1}$): 2962, 2935, 2876, 2230, 1746, 1732, 327, 1284, 1071

NMR (90 MHz, CDCl$_3$, $\delta$, ppm): 4.45 (4H, s), 4.01 (6H, s), 3.58 (4H, t), 1.86–1.41 (4H, m), 0.96 (6H, t)

Example 2

Preparation of 5,6-bis(5-methoxy-1-pentynyl)pyrazine-2,3-dicarboxylic acid dimethyl ester (Step 1) Preparation of 5-methoxy-1-pentyne In accordance with the method of Jackson et al. (*Aust. J. Chem.*, vol.41, pp.251–261, 1988), 25 g of 4-pentyn-1-ol was allowed to react with 63.3 g of iodomethane to obtain 10.7 g of 5-methoxy-1-pentyne.

Boiling point (°C.): 108–111 (760 mmHg; colorless oil)

NMR (90 MHz, CDCl$_3$, $\delta$, ppm): 3.47 (2H, t), 3.35 (3H, s), 2.29 (2H, dt), 1.95 (1H, t), 1.89–1.59 (2H, m)

(Step 2) Preparation of 5-methoxy-1-pentynylcopper

A 25 g portion of copper(I) iodide was dissolved in 450 ml of 28% aqueous ammonia, to this solution was subsequently added 250 ml of ethanol. In an atmosphere of nitrogen, to this was added dropwise a solution of 7.34 g of the compound obtained in the above step 1 in 20 ml of ethanol. After stirring for 13.5 hours at room temperature, the thus precipitated crystals were filtered and washed with 200 ml of 10% aqueous ammonia, 150 ml of water, 150 ml of ethanol and 150 ml of ether successively, followed by drying under a reduced pressure, to obtain 7.72 g of 5-methoxy-1-pentynylcopper.

(Step 3) Preparation of 5,6-bis(5-methoxy-1-pentynyl)pyrazine-2,3-dicarboxylic acid dimethyl ester To a mixture of 2.4 g of the compound obtained in the above step 2 and 2.5 g of potassium iodide was added 67 ml of N,N-dimethylformamide. In an atmosphere of nitrogen, to this were added 870 mg of Pd(PPh$_3$)$_4$ and 1.8 g of 5,6-dichloropyrazine-2,3-dicarboxylic acid dimethyl ester. After stirring at room temperature for 1.5 hours, the reaction mixture was poured into 150 ml of ice-cold water and mixed with 150 ml of ethyl acetate, and the resulting insoluble materials were removed by filtration.

The residue was washed with 150 ml of ethyl acetate, and the water layer separated from the resulting filtrate was extracted with 100 ml of ethyl acetate. The thus separated organic layers were combined, washed with 100 ml of brine and then dried over anhydrous sodium sulfate. The drying agent was removed by filtration, and the resulting filtrate was concentrated. After the purification by chromatography on a silica gel column (eluent, hexane/ethyl acetate), 2.3 g of the title compound was obtained as an oil.

IR (neat, cm$^{-1}$): 2955, 2930, 2870, 2830, 2229, 1751, 1729, 1335, 1279, 1213, 1162, 1118, 1080

NMR (90 MHz, CDCl$_3$, δ, ppm): 3.99 (6H, s), 3.53 (4H, t), 3.36 (6H, s), 2.65 (4H, t), 2.10–1.74 (4H, m)

Example 3

Preparation of 5-chloro-6-(3-methoxy-1-butynyl)pyrazine-2,3-dicarboxylic acid dimethyl ester (Step 1) Preparation of 3-methoxy-1-butyne In accordance with the method of Bell et al. (*J. Chem. Soc. Perkin Trans.* 1, pp.2879–2891, 1983), 23.2 g of 1-butyn-3-ol was allowed to react with 27.0 ml of dimethyl sulfate to obtain 9.61 g of 3-methoxy-1-butyne.

Boiling point (°C.): 62–68 (760 mmHg; colorless oil)

NMR (90 MHz, CDCl$_3$, δ, ppm): 4.07 (1H, dq), 3.41 (3H, s), 2.42 (1H, d), 1.44 (3H, d)

(Step 2) Preparation of tri-n-butyl-(3-methoxy-1-butynyl)tin

Using 7.74 g of the compound obtained in the above step 1, the step 2 of Example 1 was repeated to obtain 22.2 g of tri-n-butyl-(3-methoxy-1-butynyl)tin.

Boiling point (°C.): 104–110 (1 mmHg; colorless oil)

NMR (90 MHz, CDCl$_3$, δ, ppm): 4.07 (1H, q), 3.40 (3H, s), 1.74–1.14 (18H, m), 1.07–0.73 (12H, m)

(Step 3) Preparation of 5-chloro-6-(3-methoxy-1-butynyl)pyrazine-2,3-dicarboxylic acid dimethyl ester A 6 g portion of the compound obtained in the step 3 of Example 1 was mixed with 8.45 g of the compound obtained in the above step 2, 115 ml of anhydrous 1,4-dioxane and 1.05 g of Pd(PPh$_3$)$_4$, and the mixture was refluxed for 2 hours in an atmosphere of nitrogen.

The reaction mixture was poured into 300 ml of ice-cold water and extracted twice with 150 ml of ethyl acetate. The organic layers were combined, mixed with 150 ml of saturated potassium fluoride aqueous solution and then vigorously stirred for 15 minutes. Insoluble materials were removed by filtration, and the organic layer separated from the resulting filtrate was washed with brine and dried over anhydrous sodium sulfate. The drying agent was removed by filtration, and the filtrate was evaporated under a reduced pressure. The resulting residue was purified by chromatography on a silica gel column (eluent, hexane/ethyl acetate) to obtain 5 g of the title compound as an oil.

NMR (90 MHz, CDCl$_3$, δ, ppm): 4.40 (1H, q), 4.01 (6H, s), 3.52 (3H, s), 1.58 (3H, d)

Example 4

Preparation of 5-(3-methoxy-1-butynyl)-6-(3-n-propoxy-1-propynyl)pyrazine-2,3-dicarboxylic acid dimethyl ester A 2 g portion of the compound obtained in Example 3 was mixed with 2.48 g of the compound obtained in the step 2 of Example 1, 115 ml of anhydrous 1,4-dioxane and 300 mg of Pd(PPh3)$_4$, and the mixture was refluxed for 1 hour in an atmosphere of nitrogen. The reaction mixture was poured into 150 ml of ice-cold water and extracted twice with 200 ml of ethyl acetate. The ethyl acetate layers were combined, mixed with 200 ml of saturated potassium fluoride aqueous solution and then vigorously stirred for 30 minutes. Insoluble materials were removed by filtration.

The organic layer separated from the resulting filtrate was washed with brine and dried over anhydrous sodium sulfate. The drying agent was removed by filtration, and the solvent was evaporated under a reduced pressure. The resulting residue was purified by chromatography on a silica gel column (eluent, hexane/ethyl acetate) to obtain 773 mg of the title compound as an oil.

IR (neat, cm$^{-1}$): 2957, 2939, 2879, 2227, 1751, 1733, 1328, 1280, 1209, 1161, 1104

NMR (90 MHz, CDCl$_3$, δ, ppm): 4.45 (2H, s), 4.38 (1H, q), 4.00 (6H, s), 3.56 (2H, t), 3.50 (3H, s), 1.83–1.44 (2H, m), 1.56 (3H, d), 0.95 (3H, t)

Example 5

Preparation of 5,6-bis(3-n-propoxy-1-propynyl)pyrazine-2,3-dicarboxylic acid

A 1.46 g portion of the compound obtained in Example 1 was dissolved in 29.2 ml of methanol to which was subsequently added 7.6 ml of 1N sodium hydroxide. After stirring for 80 minutes at room temperature, the reaction mixture was mixed with 45 ml of water and washed 8 times with 30 ml of ethyl acetate. The aqueous layer was mixed with 7.6 ml of 1N hydrochloric acid and extracted three times with 50 ml of ethyl acetate. The ethyl acetate layers were combined, washed with 50 ml of water and 50 ml of brine and then dried over anhydrous magnesium sulfate. The drying agent was removed by filtration, and the solvent was evaporated under a reduced pressure. Hexane was added to the resulting residue to effect crystallization. The thus formed crystals were collected by filtration, washed with hexane and then dried to obtain 1.06 g of the title compound.

Melting point (°C.): 89.0–91.9

IR (KBr, cm$^{-1}$): 3432, 3204, 2965, 2940, 2880, 2229, 1726, 1368, 1324, 1198, 1103

NMR (90 MHz, CDCl$_3$, δ, ppm): 6.16 (2H, br. s), 4.44 (4H, s), 3.58 (4H, t), 1.83–1.38 (4H, m), 0.96 (6H, t)

Example 6

Preparation of 5,6-bis(3-n-propoxy-1-propynyl)pyrazine-2,3-dicarboxamide

A 1.2 g portion of the compound obtained in Example 1 was dissolved in 12 ml of tetrahydrofuran, and to the solution was added 12 ml of 28% aqueous ammonia and 60 mg of ammonium chloride. After 3 hours of stirring at room temperature, the reaction mixture was mixed with 50 ml of water and extracted with 200 ml of ethyl acetate. The resulting organic layer was washed with 1N hydrochloric acid and water successively and then dried over anhydrous sodium sulfate. After removing the drying agent by filtration, the resulting filtrate was concentrated and purified by chromatography on a silica gel column (eluent, hexane/ethyl acetate) to obtain 700 mg of the title compound.

Melting point (°C.): 161.6–163.2

IR (KBr, cm$^{-1}$): 3420, 3319, 3199, 2970, 2940, 2870, 2240, 1684, 1677, 1364, 1101

NMR (90 MHz, DMSO-d$_6$, δ, ppm): 7.99 (2H, br. s), 7.71 (2H, br. s), 4.49 (4H, s), 3.52 (4H, t), 1.84–1.31 (4H, m), 0.91 (6H, t)

Example 7

Preparation of 5,6-bis(3-methoxy-1-propynyl)-2,3-dicyanopyrazine

In an atmosphere of nitrogen and at −5° to 0° C., 42 ml of n-butyllithium (1.6M hexane solution) was added dropwise to a solution of 5.61 ml of methyl propargyl ether in 150 ml of tetrahydrofuran. After stirring at the same temperature for 20 minutes, 12.6 g of copper(I) iodide was added and the stirring was continued for additional 30 minutes. At room temperature, the solvent was evaporated under a reduced pressure, and the resulting residue was mixed with 300 ml of N,N-dimethylformamide. In an atmosphere of nitrogen and with cooling on an ice bath, to this were added 11.0 g of potassium iodide, 2.78 g of Pd(PPh$_3$)$_4$ and 6.0 g of 2,3-dichloro-5,6-dicyanopyrazine. After stirring for 35 minutes, the reaction mixture was poured into 300 ml of ice-cold water and mixed with 500 ml of ethyl acetate and then resulting insoluble materials were removed by filtration.

The resulting filtrate was separated, and the organic layer was washed with 100 ml of brine and dried over anhydrous sodium sulfate. After removing the drying agent by filtration, the resulting filtrate was concentrated, purified by chromatography on a silica gel column (eluent, hexane/ethyl acetate) and then recrystallized from ethanol to obtain 1.40 g of the title compound.

Melting point (°C.): 94.7–95.0

IR (KBr, cm$^{-1}$): 3009, 2939, 2908, 2891, 2831, 2243, 2233, 1509, 1389, 1181, 1102, 952

NMR (90 MHz, CDCl$_3$, δ, ppm): 4.46 (4H, s), 3.50 (6H, s)

Example 8

Preparation of 5,6-bis(3-acetoxy-1-propynyl)-2,3-dicyanopyrazine (Step 1) Preparation of 5,6-bis(3-t-butyldimethylsilyloxy-1-propynyl)-2,3-dicyanopyrazine In an atmosphere of nitrogen, to the solution of 20.9 g of t-butyl dimethylsilylpropargyl ether dissolved in 280 ml of tetrahydrofuran was added dropwise 76.9 ml of n-butyllithium (1.6M hexane solution) below −60° C. After stirring for 40 minutes at the same temperature, the reaction solution was warmed to 0° C., cooled again to −60° C. and then mixed with 23.4 g of copper(I) iodide. After stirring for 1.5 hours on an ice bath, the solvent was evaporated under a reduced pressure at room temperature, and the resulting residue was mixed with 560 ml of N,N-dimethylformamide. In an atmosphere of nitrogen and with cooling on an ice bath, to this were added 20.4 g of potassium iodide, 5.0 g of Pd(PPh$_3$)$_4$ and 11.1 g of 2,3-dichloro-5,6-dicyanopyrazine, and the mixture was stirred for 30 minutes.

The reaction mixture was poured into 1 liter of ice-cold water and mixed with 1 liter of ethyl acetate, and insoluble materials were removed by filtration. The water layer separated from the resulting filtrate was extracted with 300 ml of ethyl acetate. The organic layers were combined, washed with 500 ml of brine and then dried over anhydrous sodium sulfate. After removing the drying agent by filtration, the resulting filtrate was concentrated and purified by chromatography on a silica gel column (eluent, hexane/ethyl acetate) to obtain 9.2 g of 5,6-bis(3-t-butyldimethylsilyloxy-1-propynyl)-2,3-dicyanopyrazine as an oil.

NMR (90 MHz, CDCl$_3$, δ, ppm): 4.65 (4H, s), 0.93 (18H, s), 0.17 (12H, s)

(Step 2) Preparation of 5,6-bis(3-hydroxy-1-propynyl)-2,3-dicyanopyrazine

A 9.2 g portion of the compound obtained in the above step 1 was dissolved in 36 ml of tetrahydrofuran, and the solution was mixed with 36 ml of water and 108 ml of acetic acid and then stirred at room temperature for 17 hours. The reaction mixture was poured into 300 ml of ice-cold water and extracted twice with 400 ml and 100 ml of ethyl acetate. The resulting organic layer was washed twice with 100 ml of water and once with 100 ml of brine and then dried over anhydrous sodium sulfate. After removing the drying agent by filtration, the resulting filtrate was concentrated, and the resulting residue was crystallized from ether and hexane to obtain 2.0 g of 5,6-bis(3-hydroxy-1-propynyl)-2,3-dicyanopyrazine.

Melting point (°C.): 169.0–172.2

IR (KBr, cm$^{-1}$): 3350, 2938, 2240, 2224, 1515, 1436, 1376, 1190, 1013

NMR (90 MHz, DMSO-d$_6$, δ, ppm): 5.67 (2H, t), 4.48 (4H, d)

(Step 3) Preparation of 5,6-bis(3-acetoxy-1-propynyl)-2,3-dicyanopyrazine

A 8.3 ml portion of acetic anhydride was added to 700 mg of 5,6-bis(3-hydroxy-1-propynyl)-2,3-dicyanopyrazine. The mixture was stirred at 70° C. for 7.5 hours. After spontaneous cooling, the reaction mixture was poured into 100 ml of ice-cold water and extracted with 200 ml of ethyl acetate. The resulting organic layer was washed twice with 50 ml of water and twice with 50 ml of brine and then dried over anhydrous sodium sulfate. After removing the drying agent by filtration, the resulting filtrate was concentrated and purified by chromatography on a silica gel column (eluent, hexane/ethyl acetate) to obtain 770 mg of the title compound as an oil.

IR (neat, cm$^{-1}$): 2950, 2236, 1751, 1744, 1510, 1386, 1374, 1226, 1218, 1185, 1044

NMR (90 MHz, CDCl$_3$, δ, ppm): 5.02 (4H, s), 2.17 (6H, s)

Example 9

Preparation of 5,6-bis(3-carbamoyloxy-1-propynyl)-2,3-dicyanopyrazine

A 500 mg portion of the compound obtained in the step 2 of Example 8 was suspended in 8 ml of benzene. To this was added 550 mg of sodium cyanate, followed by the dropwise addition of 0.68 ml of trifluoroacetic acid and resulting mixture was stirred for 64 hours at room temperature.

The reaction mixture was poured into 50 ml of ice-cold water and extracted twice with 100 ml and 50 ml of ethyl acetate. The resulting organic layer was washed with 50 ml of water and 50 ml of brine and then dried over anhydrous sodium sulfate. After removing the drying agent by filtration, the resulting filtrate was concentrated, and the resulting residue was recrystallized from methanol/ethyl acetate to obtain 140 mg of the title compound.

Melting point (°C.): >185 (decomposition)
IR (KBr, cm$^{-1}$): 3442,3417, 2237, 1734, 1378, 1325, 1083, 1066
NMR (90 MHz, DMSO-d$_6$, δ, ppm): 6.82 (4H, br. s), 5.00 (4H, s)

Example 10

Preparation of 2,3-bis(3-ethoxy-1-butynyl)quinoxaline (Step 1) Preparation of 3-ethoxy-1-butyne To 62 ml of dimethyl sulfoxide were added 21 g of potassium hydroxide and 25 ml of 1-butyn-3-ol. With cooling on an ice bath, 54.7 g of ethyl iodide was added dropwise to the above mixture and the mixture was stirred for 1.5 hours on a water bath at 40° C. The resulting upper layer was separated, washed with 50 ml of water and 50 ml of brine and then dried over anhydrous sodium sulfate. After removing the drying agent by filtration, the resulting filtrate was distilled to obtain 20.3 g of 3-ethoxy-1-butyne.

Boiling point (°C.): 79–85 (colorless oil)
NMR (90 MHz, CDCl$_3$, δ, ppm): 4.15 (1H, dq), 3.96–3.63 (1H, m), 3.60–3.27 (1H, m), 2.40 (1H, d), 1.44 (3H, d), 1.23 (3H, t)

(Step 2) Preparation of tri-n-butyl-(3-ethoxy-1-butynyl)tin

A 9 g portion of the compound obtained in the above step 1 was added to 140 ml of anhydrous ether and, in an atmosphere of nitrogen, the mixture was cooled to −70° C. or lower on a dry ice-acetone bath. To this was added dropwise 58 ml of 1.6M n-butyllithium (hexane solution) below −65° C. After stirring at the same temperature for 10 minutes, the reaction mixture was warmed to 0° C. and again cooled to −70° C. To this was added dropwise a solution 25 ml of tri-n-butyltin chloride in 100 ml of anhydrous ether. The mixture was warmed to room temperature and stirred for 16 hours at the same temperature.

The reaction solution was poured into 100 ml of ice-cold water and mixed with 200 ml of ether. The ether layer separated therefrom was washed twice with 100 ml of water and once with 100 ml of brine and then dried over anhydrous sodium sulfate. The drying agent was removed by filtration, and the solvent was evaporated under a reduced pressure. The resulting residue was distilled under a reduced pressure to obtain 32 g of tri-n-butyl-(3-ethoxy-1-butynyl)tin.

Boiling point (°C.): 115–126 (1 mmHg; colorless oil)
NMR (90 MHz, CDCl$_3$, δ, ppm): 4.16 (1H, q), 3.91–3.64 (1H, m), 3.60–3.26 (1H, m), 1.63–1.14 (21H, m), 1.06–0.82 (12H, m)

(Step 3) Preparation of 2,3-bis(3-ethoxy-1-butynyl)quinoxaline

A mixture of 1.5 g portion of 2,3-dichloroquinoxaline, 5.8 g of the compound obtained in the above step 2,38 ml of anhydrous 1,4-dioxane and 690 mg of Pd(PPh$_3$)$_4$ was refluxed for 4.5 hours in an atmosphere of nitrogen. To this was further added 1,5 g of the compound obtained in the above step 2. After the reaction mixture was refluxed for 2 hours, the reaction mixture was poured into 100 ml of ice-cold water.

This was mixed with 100 ml of ethyl acetate and 100 ml of saturated potassium fluoride aqueous solution and the resulting mixture was vigorously stirred for 30 minutes at room temperature. After removing insoluble materials by filtration, the organic layer separated from the resulting filtrate, was washed with water and then dried over anhydrous sodium sulfate. After removing the drying agent by filtration and evaporating the solvent under a reduced pressure, the resulting residue was purified by chromatography on a silica gel column (eluent, hexane/ethyl acetate) and then recrystallized from hexane to obtain 1.63 g of the title compound.

Melting point (°C.): 43.8–44.8
IR (KBr, cm$^{-1}$): 2980, 2933, 2866, 2230, 1339, 1195, 1128, 1112, 1075, 765
NMR (90 MHz, CDCl$_3$, δ, ppm): 8.16–7.92 (2H, m), 7.86–7.60 (2H, m), 4.52 (2H, q), 4.17–3.77 (2H, m), 3.77–3.35 (2H, m), 1.62 (6H, d), 1.28 (6H, t)

Example 11

Preparation of 2,3-bis(3-methoxy-1-pentynyl)quinoxaline (Step 1) Preparation of 3-methoxy-1-pentyne In the similar manner to the step 1 of Example 3, 50.0 g of 1-pentyn-3-ol was allowed to react with 48.6 ml of dimethyl sulfate to obtain 32.0 g of 3-methoxy-1-pentyne.

Boiling point (°C.): 87–100 (760 mmHg; colorless oil)
NMR (90 MHz, CDCl$_3$, δ, ppm): 3.88 (1H, dt), 3.41 (3H, s), 2.43 (1H, d), 1.93–1.52 (2H, m), 1.00 (3H, t)

(Step 2) Preparation of tri-n-butyl-(3-methoxy-1-pentynyl)tin

Using 9.0 g of the compound obtained in the above step 1, the step 2 of Example 1 was repeated to obtain 24.5 g of tri-n-butyl-(3-methoxy-1-pentynyl)tin.

Boiling point (°C.): 110–118 (1 mmHg; colorless oil)
NMR (90 MHz, CDCl$_3$, δ, ppm): 3.89 (1H, t), 3.41 (3H, s), 2.08–1.16 (20H, m), 1.09–0.60 (12H, m)

(Step 3) Preparation of 2,3-bis(3-methoxy-1-pentynyl)quinoxaline

A 1.0 g portion of 2,3-dichloroquinoxaline was dissolved in 25 ml of 1,4-dioxane. In an atmosphere of nitrogen, to this were added 4.49 g of the compound obtained in the above step 2 and 460 mg of Pd(PPh$_3$)$_4$, and the resulting mixture was refluxed for 6.5 hours. After spontaneous cooling, the reaction mixture was poured into 50 ml of ice-cold water, mixed with 100 ml of ethyl acetate and 50 ml of saturated potassium fluoride aqueous solution and then vigorously stirred for 15 minutes. After removing insoluble materials by filtration, the organic layer was separated from the resulting filtrate, washed twice with 50 ml of water and once with 100 ml of brine and then dried over anhydrous sodium sulfate. After removing the drying agent by filtration, the resulting filtrate was concentrated, purified by chromatography on a silica gel column (eluent, hexane/ethyl acetate) and then crystallized from hexane to obtain 1.12 g of the title compound.

Melting point (°C.): 49.6–51.4
IR (KBr, cm$^{-1}$): 2979, 2932, 2821, 2225, 1340, 1187, 1131, 1124, 1102, 1091, 1077, 779

NMR (90 MHz, CDCl$_3$, δ, ppm): 8.13–7.95 (2H, m), 7.86–7.68 (2H, m), 4.24 (2H, t), 3.54 (6H, s), 2.10–1.71 (4H, m), 1.12 (6H, t)

Example 12

Preparation of 2,3-bis(4-methoxy-1-butynyl)quinoxaline (Step 1) Preparation of 4-methoxy-1-butyne In accordance with the method of Jackson et al. (*Aust. J. Chem.*, vol.41, pp.251–261, 1988), 50 g of 3-butyn-1-ol was allowed to react with 49.5 g of dimethyl sulfate to synthesize 20.6 g of 4-methoxy-1-butyne.

Boiling point (°C.): 70–84 (760 mmHg; colorless oil)

NMR (90 MHz, CDCl$_3$, δ, ppm): 3.52 (2H, t), 3.38 (3H, s), 2.47 (2H, dt), 1.99 (1H, t)

(Step 2) Preparation of 4-methoxy-1-butynylcopper

In an atmosphere of nitrogen and with stirring at room temperature, to a solution of 51.6 g portion of copper(I) iodide dissolved in 927 ml of 28% aqueous ammonia was added dropwise a solution 12.9 g of the compound obtained in the above step 1 in 42.3 ml of ethanol.

After stirring for 16 hours, the thus precipitated yellow crystals were collected by filtration and washed with 500 ml of 10% aqueous ammonia, 500 ml of water, 2 liters of ethanol, 1 liter of ethanol:ether (1:1) and 2 liters of ether in that order, followed by drying under a reduced pressure, to obtain 11.6 g of 4-methoxy-1-butynylcopper as light yellow crystals.

(Step 3) Preparation of 2,3-bis(4-methoxy-1butynyl)quinoxaline

In an atmosphere of nitrogen and at room temperature, to a suspension of 2 g of 2,3-dichloroquinoxaline, 3.7 g of potassium iodide and 3.2 g of the compound obtained in the above step 2 in 100 ml of anhydrous N,N-dimethylformamide was added 1.28 g of Pd(PPh$_3$)$_4$ and the mixture was stirred for 23.5 hours. The reaction solution was mixed with 100 ml of water and 150 ml of ethyl acetate. After removing insoluble materials by filtration, the organic layer was separated from the resulting filtrate, washed with water and brine and then dried over anhydrous sodium sulfate. After removing the drying agent by filtration and evaporating the solvent under a reduced pressure, the resulting residue was purified by chromatography on a silica gel column (eluent, hexane/ethyl acetate) and then crystallized from hexane to obtain 0.75 g of the title compound.

Melting point (°C.): 43.3–44.1

IR (KBr, cm$^{-1}$): 2936, 2886, 2232, 1339, 1326, 1197, 1111, 764

NMR (90 MHz, CDCl$_3$, δ, ppm): 8.07–7.84 (2H, m), 7.77–7.52 (2H, m), 3.71 (4H, t), 3.43 (6H, s), 2.86 (4H, t)

Example 13

Preparation of 2,3-bis(3-ethoxy-3-methyl-1-butynyl)quinoxaline (Step 1) Preparation of 2,3-bis(3-hydroxy-3-methyl-1-butynyl)quinoxaline A 5.0 g portion of 2,3-dichloroquinoxaline was dissolved in 75 ml of dimethyl sulfoxide. A 380 mg portion of copper(I) iodide, 1.41 g of bis(triphenylphosphine)palladium(II) chloride and 7.31 ml of 3-methyl-1-butyn-3-ol were added to the above solution. After further adding 200 ml of triethylamine, the resulting mixture was stirred for 17 hours at room temperature in an atmosphere of argon.

Triethylamine was evaporated under a reduced pressure, and the resulting residue was poured into 300 ml of ice-cold water. The thus formed precipitate was collected by filtration and washed with 100 ml of water. After drying, the crystals were purified by chromatography on an alumina column (eluent, hexane/ethyl acetate) and a silica gel column (eluent, 4% methanol-dichloromethane) to obtain 6.52 g of 2,3-bis(3-hydroxy-3-methyl-1-butynyl)quinoxaline.

Melting point (°C.): 161.6–162.0

IR (KBr, cm$^{-1}$): 3458, 3367, 2983, 2226, 1356, 1340, 1225, 1173, 1130, 966, 775

NMR (90 MHz, CDCl$_3$, δ, ppm): 8.08–7.90 (2H, m), 7.82–7.64 (2H, m), 3.09 (2H, br. s), 1.71 (12H, s)

(Step 2) Preparation of 2,3-bis(3-ethoxy-3-methyl-1-butynyl)quinoxaline

A 0.7 g portion of the compound obtained in the above step 1 was dissolved in 5 ml of N,N-dimethylformamide. With cooling on an ice bath, to this was added 220 mg of sodium hydride in portions. After adding 0.45 ml of iodoethane, the resulting mixture was stirred for 1 hour on an ice bath. The reaction solution was poured into 50 ml of ice-cold water and extracted with 100 ml of ethyl acetate. The resulting organic layer was washed with 30 ml of water and 30 ml of brine and then dried over anhydrous sodium sulfate. After removing the drying agent by filtration, the resulting filtrate was concentrated and purified by chromatography on an alumina column (eluent, hexane/ethyl acetate) to obtain 580 mg of the title compound.

IR (neat, cm$^{-1}$): 2983, 2933, 2900, 2877, 2227, 1336, 1234, 1165, 1109, 1070

NMR (90 MHz, CDCl$_3$, δ, ppm): 8.10–7.89 (2H, m), 7.80–7.59 (2H, m), 3.77 (4H, q), 1.66 (12H, s), 1.26 (6H, t)

Example 14

Preparation of 2,3-bis((S)-3-ethoxy-1-butynyl)quinoxaline (Step 1) Preparation of (S)-3-butyn-2-ol In accordance with the method of Smith et al. (*J. Med. Chem.*, vol.31, pp.1558–1566, 1988), 138 g of 3-butyn-2-ol was subjected to optical resolution to obtain 21.8 g of (S)-3-butyn-2-ol.

NMR (90 MHz, CDCl$_3$, δ, ppm): 4.53 (1H, m), 2.45 (1H, d), 2.00 (1H, br. s), 1.48 (3H, d)

(Step 2) Preparation of (S)-3-ethoxy-1-butyne

In the same manner as the step 1 of Example 10, 6.5 g of the compound obtained in the above step 1 was allowed to react with 15.9 g of iodoethane to obtain 7.9 g of (S)-3-ethoxy-1-butyne.

Boiling point (°C.): 78–84 (colorless oil)

NMR (90 MHz, CDCl$_3$, δ, ppm): 4.19 (1H, dq), 3.96–3.60 (1H, m), 3.56–3.27 (1H, m), 2.39 (1H, d), 1.45 (3H, d), 1.23 (3H, t)

(Step 3) Preparation of (S)-tri-n-butyl-(3-ethoxy-1-butynyl)tin

Using 7.0 g of the compound obtained in the above step 2, the step 2 of Example 10 was repeated to obtain 19.8 g of (S)-tri-n-butyl-(3-ethoxy-1-butynyl)tin.

Boiling point (°C.): 101–111 (1 mmHg; colorless oil)

NMR (90 MHz, CDCl$_3$, δ, ppm): 4.16 (1H, q), 3.94–3.64 (1H, m), 3.60–3.24 (1H, m), 1.76–1.14 (21H, m), 1.07–0.60 (12H, m)

(Step 4) Preparation of 2,3-bis((S)-3-ethoxy-1-butynyl)quinoxaline

Using 7.3 g of the compound obtained in the above step 3, the step 3 of Example 10 was repeated to obtain 1.41 g of the title compound.

Melting point (°C.): 76.4–77.0

IR (KBr, cm$^{-1}$): 2977, 2868, 2222, 1339, 1318, 1195, 1127, 1112, 1075, 767

NMR (90 MHz, CDCl$_3$, δ, ppm): 8.17–7.93 (2H, m), 7.93–7.66 (2H, m), 4.51 (2H, q), 4.19–3.78 (2H, m), 3.78–3.36 (2H, m), 1.62 (6H, d), 1.28 (6H, t)

$[\alpha]^{25.5}_D$ –148.5° (CHCl$_3$, C=0.80)

Examples 15 and 16

Preparation of
2,3-bis((R)-3-ethoxy-1-butynyl)quinoxaline
(Example 15) and
2-chloro-3-((R)-3-ethoxy-1-butynyl)quinoxaline
(Example 16)

(Step 1) Preparation of (R)-3-butyn-2-ol

In accordance with the method of Smith et al. (*J. Med. Chem.*, vol.31, pp.1558–1566, 1988), 143.4 g of 3-butyn-2-ol was subjected to optical resolution to obtain 14.9 g of (R)-3-butyn-2-ol.

NMR (90 MHz, CDCl$_3$, δ, ppm): 4.71–4.35 (1H, m), 2.45 (1H, d), 1.88 (1H, d), 1.48 (3H, d)

(Step 2) Preparation of (R)-3-ethoxy-1-butyne

In the same manner as the step 1 of Example 10, 13.0 g of the compound obtained in the above step 1 was allowed to react with 31.9 g of iodoethane to obtain 11.8 g of (R)-3-ethoxy-1-butyne.

Boiling point (°C.): 76–84 (colorless oil)

NMR (90 MHz, CDCl$_3$, δ, ppm): 4.15 (1H, dq), 3.96–3.63 (1H, m), 3.60–3.27 (1H, m), 2.40 (1H, d), 1.44 (3H, d), 1.23 (3H, t)

(Step 3) Preparation of 2,3-bis((R)-3-ethoxy-1-butynyl)quinoxaline and 2-chloro-3-((R)-3-ethoxy-1-butynyl)quinoxaline To a mixture of 3.0 g of 2,3-dichloroquinoxaline, 120 ml of triethylamine and 45 ml of dimethyl sulfoxide were added 57.3 mg of copper(I) iodide and 296 mg of Pd(PPh$_3$)$_2$Cl$_2$, and then the mixture was stirred for 10 minutes at room temperature in an atmosphere of nitrogen. A 3.7 g portion of the compound obtained in the above step 2 was added to the reaction mixture and the resulting mixture was stirred overnight at room temperature and then for 8 hours at 30° C. The reaction solvent was evaporated under a reduced pressure, and the resulting residue was mixed with 200 ml of ethyl acetate and 200 ml of water. The thus separated organic layer was washed twice with 100 ml of water and once with 100 ml of brine and then dried over anhydrous sodium sulfate. After removing the drying agent by filtration and evaporating the solvent under a reduced pressure, the resulting residue was subjected to a silica gel column chromatography (eluent, ethyl acetate :hexane=1:5) to obtain 2.5 g of 2,3-bis((R)-3-ethoxy-1-butynyl)quinoxaline and 1.73 g of 2-chloro-3-((R)-3-ethoxy-1-butynyl)quinoxaline.

(1) 2,3-bis((R)-3-ethoxy-1-butynyl)quinoxaline (Example 15)

Melting point (°C.): 75.6–76.6

IR (KBr, cm$^{-1}$): 2977, 2867, 2223, 1339, 1318, 1195, 1127, 1112, 1075, 767

NMR (90 MHz, CDCl$_3$, δ, ppm): 8.13–7.88 (2H, m), 7.84–7.56 (2H, m), 4.52 (2H, q), 4.12–3.73 (2H, m), 3.73–3.32 (2H, m), 1.62 (6H, d), 1.28 (6H, t)

$[\alpha]^{31}_D$ +154.9° (CHCl$_3$, C=1.0)

(2) 2-chloro-3-((R)-3-ethoxy-1-butynyl)quinoxaline (Example 16)

NMR (90 MHz, CDCl$_3$, δ, ppm): 8.21–7.96 (2H, m), 7.96–7.68 (2H, m), 4.53 (1H, q), 4.20–3.81 (1H, m), 3.81–3.42 (1H, m), 1.63 (3H, d), 1.30 (3H, t)

Example 17

Preparation of
2-((R)-3-ethoxy-1-butynyl)-3-((S)-3-ethoxy-1-butynyl)quinoxaline

In the same manner as the procedure of Example 4, 3.36 g of the compound obtained in the step 3 of Example 14 was allowed to react with 1.59 g of the compound of Example 16 to obtain 0.8 g of the title compound.

IR (KBr, cm$^{-1}$): 2981, 2868, 2221, 1339, 1194, 1111, 1073, 764

NMR (90 MHz, CDCl$_3$, δ, ppm): 8.17–7.95 (2H, m), 7.90–7.65 (2H, m), 4.52 (2H, q), 4.18–3.78 (2H, m), 3.78–3.37 (2H, m), 1.62 (6H, d), 1.28 (6H, t)

Example 18

Preparation of 2,3-bis((S)-3-(2-methoxyethoxy)-1-pentynyl)quinoxaline (Step 1) Preparation of (S)-1-pentyn-3-ol In the same manner as the procedure of the step 1 of Example 14, 100 g of 1-pentyn-3-ol was subjected to optical resolution to obtain 14.7 g of (S)-1-pentyn-3-ol.

NMR (90 MHz, CDCl$_3$, δ, ppm): 4.33 (1H, dt), 2.46 (1H, d), 1.89–1.52 (2H, m), 1.03 (3H, t)

(Step 2) Preparation of (S)-3-(2-methoxyethoxy)-1-pentyne

Using 13.8 g of the compound obtained in the above step 1 and 15.5 g of 2-chloroethyl methyl ether, the procedure of the step 1 of Example 10 was repeated to obtain 7.3 g of (S)-3-(2-methoxyethoxy)-1-pentyne.

Boiling point (°C.): 140–162 (colorless oil)

NMR (90 MHz, CDCl$_3$, δ, ppm): 4.04 (1H, dt), 3.99–3.75 (1H, m), 3.69–3.49 (3H, m), 3.40 (3H, s), 2.43 (1H, d), 1.97–1.54 (2H, m), 1.03 (3H, t)

(Step 3) Preparation of (S)-tri-n-butyl-(3-(2-methoxyethoxy)-1-pentynyl)tin

Using 7.2 g of the compound obtained in the above step 2, the procedure of the step 2 of Example 10 was repeated to obtain 16.6 g of (S)-tri-n-butyl-(3-(2-methoxyethoxy)-1-pentynyl)tin.

Boiling point (°C.): 138–143 (0.5 mmHg; colorless oil)

NMR (90 MHz, CDCl$_3$, δ, ppm): 4.03 (1H, t), 3.96–3.75 (1H, m), 3.69–3.47 (3H, m), 3.38 (3H, s), 1.82–1.16 (20H, m), 1.07–0.66 (12H, m)

(Step 4) Preparation of 2,3-bis((S)-3-(2-methoxyethoxy)-1-pentynyl)quinoxaline

Using 8.5 g of the compound obtained in the above step 3, the procedure of the step 3 of Example 10 was repeated to obtain 2.39 g of the title compound.

IR (neat, cm$^{-1}$): 2970, 2929, 2877, 2226, 1338, 1132, 1109, 1090, 766

NMR (90 MHz, CDCl$_3$, δ, ppm): 8.10–7.92 (2H, m), 7.83–7.65 (2H, m), 4.40 (2H, t), 4.14–3.84 (2H, m), 3.84–3.48 (6H, m), 3.40 (6H, s), 2.10–1.74 (4H, m), 1.13 (6H, t)

$[\alpha]^{24.5}_D$ –106.5° (CHCl$_3$, C=1.0)

Example 19

Preparation of 2,3-bis((R)-3-(2-methoxyethoxy)-1-pentynyl)quinoxaline (Step 1) Preparation of (R)-1-pentyn-3-ol In the same manner as the procedure of the step 1 of Example 15, 100 g of 1-pentyn-3-ol was subjected to optical resolution to obtain 16.1 g of (R)-1-pentyn-3-ol.

NMR (90 MHz, CDCl$_3$, δ, ppm): 4.33 (1H, dt), 2.44 (1H, d), 1.93–1.52 (2H, m), 1.02 (3H, t)

(Step 2) Preparation of (R)-3-(2-methoxyethoxy)-1-pentyne

In the same manner as the procedure of the step 1 of Example 10, 8.0 g of the compound obtained in the above step 1 was allowed to react with 13.2 g of 2-bromoethyl methyl ether to obtain 7.87 g of (R)-3-(2-methoxyethoxy)-1-pentyne.

Boiling point (°C.): 138–162 (colorless oil)

NMR (90 MHz, CDCl$_3$, δ, ppm): 4.04 (1H, dt), 3.99–3.75 (1H, m), 3.69–3.49 (3H, m), 3.40 (3H, s), 2.43 (1H, d), 1.97–1.54 (2H, m), 1.03 (3H, t)

$[\alpha]^{31}_D$+74.0° (CHCl$_3$, C=1.08)

(Step 3) Preparation of (R)-tri-n-butyl-(3-(2-methoxyethoxy)-1-pentynyl)tin

Using 7.5 g of the compound obtained in the above step 2, the procedure of the step 2 of Example 10 was repeated to obtain 16.39 g of (R)-tri-n-butyl-(3-(2-methoxyethoxy)-1-pentynyl)tin.

Boiling point (°C.): 125–140 (0.15 mmHg; colorless oil)

NMR (90 MHz, CDCl$_3$, δ, ppm): 4.03 (1H, t), 3.99–3.81 (1H, m), 3.71–3.45 (3H, m), 3.38 (3H, s), 1.93–1.20 (20H, m), 1.11–0.60 (12H, m)

(Step 4) Preparation of 2,3-bis((R)-3-(2-methoxyethoxy)-1-pentynyl)quinoxaline

Using 3.52 g of the compound obtained in the above step 3, the procedure of the step 3 of Example 10 was repeated to obtain 0.64 g of the title compound.

IR (neat, cm$^{-1}$): 2970, 2926, 2875, 2224, 1338, 1130, 1109, 1084, 766

NMR (90 MHz, CDCl$_3$, δ, ppm): 8.10–7.92 (2H, m), 7.83–7.65 (2H, m), 4.40 (2H, t), 4.14–3.84 (2H, m), 3.84–3.48 (6H, m), 3.40 (6H, s), 2.10–1.74 (4H, m), 1.13 (6H, t)

$[\alpha]^{29}_D$+104.6° (CHCl$_3$, C=0.82)

Example 20

Preparation of 2-chloro-3-((S)-3-(2-methoxyethoxy)-1-pentynyl)quinoxaline

Using 3.25 g of the compound obtained in the step 3 of Example 18 and 1.5 g of 2,3-dichloroquinoxaline, the procedure of Example 3 was repeated to obtain 2 g of the title compound.

NMR (90 MHz, CDCl$_3$, δ, ppm): 8.14–7.95 (2H, m), 7.89–7.69 (2H, m), 4.42 (1H, t), 4.20–3.92 (1H, m), 3.86–3.54 (3H, m), 3.42 (3H, s), 2.10–1.80 (2H, m), 1.14 (3H, t)

Example 21

Preparation of 2-((R)-3-(2-methoxyethoxy)-1-pentynyl)-3-((S)-3-(2-methoxyethoxy)-1-pentynyl)quinoxaline Using 1.9 g of the compound obtained in Example 20 and 3.2 g of the compound obtained in the step 3 of Example 19, the procedure of Example 4 was repeated to obtain 0.99 g of the title compound.

IR (neat, cm$^{-1}$): 2972, 2931, 2877, 2226, 1338, 1132, 1107, 1090, 766

NMR (90 MHz, CDCl$_3$, δ, ppm): 8.10–7.92 (2H, m), 7.83–7.65 (2H, m), 4.40 (2H, t), 4.14–3.84 (2H, m), 3.84–3.48 (6H, m), 3.40 (6H, s), 2.10–1.74 (4H, m), 1.13 (6H, t)

Example 22

Preparation of 2,3-bis((S)-3-(2-ethoxyethoxy)-1-pentynyl)quinoxaline (Step 1) Preparation of (S)-3-(2-ethoxyethoxy)-1-pentyne In the same manner as the procedure of the step 1 of Example 10, 8.1 g of the compound obtained in the step 1 of Example 18 was allowed to react with 16.2 g of 2-bromoethyl ethyl ether to obtain 11.0 g of (S)-3-(2-ethoxyethoxy)-1-pentyne.

Boiling point (°C.): 134–170 (colorless oil)

NMR (90 MHz, CDCl$_3$, δ, ppm): 4.04 (1H, dt), 4.00–3.77 (1H, m), 3.71–3.54 (3H, m), 3.54 (2H, q), 2.41 (1H, d), 1.93–1.59 (2H, m), 1.21 (3H, t), 1.00 (3H, t)

$[\alpha]^{25}_D$−65.1° (CHCl$_3$, C=1.96)

(Step 2) Preparation of (S)-tri-n-butyl-(3-(2-ethoxyethoxy)-1-pentynyl)tin

Using 11.0 g of the compound obtained in the above step 1, the procedure of the step 2 of Example 10 was repeated to obtain 25.0 g of (S)-tri-n-butyl-(3-(2-ethoxyethoxy)-1-pentynyl)tin.

Boiling point (°C.): 131–145 (0.15 mmHg; colorless oil)

NMR (90 MHz, CDCl$_3$, δ, ppm): 4.04 (1H, t), 3.99–3.81 (1H, m), 3.77–3.56 (3H, m), 3.54 (2H, q), 1.97–0.60 (35H, m)

(Step 3) Preparation of 2,3-bis((S)-3-(2-ethoxyethoxy)-1-pentynyl)quinoxaline

Using 8.5 g of the compound obtained in the above step 2, the procedure of the step 3 of Example 10 was repeated to obtain 2.39 g of the title compound.

IR (neat, cm$^{-1}$): 2974, 2933, 2872, 2226, 1475, 1460, 1394, 1338, 1211, 1190, 1107, 766

NMR (270 MHz, CDCl$_3$, δ, ppm): 8.08–8.02 (2H, m), 7.80–7.74 (2H, m), 4.41 (2H, t), 4.07–3.97 (2H, m), 3.75–3.62 (6H, m), 3.56 (4H, q), 2.00–1.87 (4H, m), 1.22 (6H, t), 1.13 (6H, t)

$[\alpha]^{29.5}_D$−105.2° (CHCl$_3$, C=1.03)

Example 23

Preparation of 2,3-bis((R)-3-(2-ethoxyethoxy)-1-pentynyl)quinoxaline (Step 1) Preparation of (R)-3-(2-ethoxyethoxy)-1-pentyne Using 7.9 g of the compound obtained in the step 1 of Example 19 and 15.8 g of 2-bromoethylethyl ether, the procedure of the step 1 of Example 10 was repeated to obtain 10.8 g of (R)-3-(2-ethoxyethoxy)-1-pentyne.

Boiling point (°C.): 150–170 (colorless oil)

NMR (90 MHz, CDCl$_3$, δ, ppm): 4.03 (1H, dt), 4.01–3.79 (1H, m), 3.73–3.51 (3H, m), 3.54 (2H, q), 2.41 (1H, d), 1.95–1.59 (2H, m), 1.21 (3H, t), 1.00 (3H, t)

$[\alpha]^{26}_D$+65.2° (CHCl$_3$, C=0.92)

(Step 2) Preparation of (R)-tri-n-butyl-(3-(2-ethoxyethoxy)-1-pentynyl)tin

Using 10.8 g of the compound obtained in the above step 1, the procedure of the step 2 of Example 10 was repeated to obtain 24.67 g of (R)-tri-n-butyl-(3-(2-ethoxyethoxy)-1-pentynyl)tin.

Boiling point (°C.): 125–140 (0.15 mmHg; colorless oil)

NMR (90 MHz, CDCl$_3$, δ, ppm): 4.04 (1H, t), 3.99–3.79 (1H, m), 3.75–3.54 (3H, m), 3.54 (2H, q), 2.01–0.60 (35H, m)

(Step 3) Preparation of 2,3-bis((R)-3-(2-ethoxyethoxy)-1-pentynyl)quinoxaline

Using 3.9 g of the compound obtained in the above step 2, the procedure of the step 3 of Example 10 was repeated to obtain 1.09 g of the title compound.

IR (neat, cm$^{-1}$): 2974, 2931, 2872, 2226, 1475, 1460, 1394, 1338, 1211, 1190, 1109, 766

NMR (270 MHz, CDCl$_3$, δ, ppm): 8.06–8.03 (2H, m), 7.80–7.74 (2H, m), 4.41 (2H, t), 4.08–3.97 (2H, m), 3.75–3.62 (6H, m), 3.56 (4H, q), 2.02–1.87 (4H, m), 1.22 (6H, t), 1.13 (6H, t)

$[\alpha]^{29}_D$+101.8° (CHCl$_3$, C=1.04)

Example 24

Preparation of 2-chloro-3-((R)-3-(2-ethoxyethoxy)-1-pentynyl)quinoxaline

Using 2.46 g of the compound obtained in the step 2 of Example 23 and 1 g of 2,3-dichloroquinoxaline, the procedure of Example 3 was repeated to obtain 0.93 g of the title compound.

NMR (90 MHz, CDCl$_3$, δ, ppm): 8.14–7.93 (2H, m), 7.89–7.67 (2H, m), 4.42 (1H, t), 4.20–3.90 (1H, m), 3.86–3.60 (3H, m), 3.57 (2H, q), 2.14–1.76 (2H, m), 1.22 (3H, t), 1.13 (3H, t)

$[\alpha]^{27}_D$+59.1° (CHCl$_3$, C=0.92)

Example 25

Preparation of 2-((R)-3-(2-ethoxyethoxy)-1-pentynyl)-3-((S)-3-(2-ethoxyethoxy)-1-pentynyl)quinoxaline Using 2 g of the compound obtained in Example 24 and 3.35 g of the compound obtained in the step 2 of Example 22, the procedure of Example 4 was repeated to obtain 2.17 g of the title compound.

IR (neat, cm$^{-1}$): 2974, 2933, 2872, 2226, 1475, 1460, 1394, 1338, 1211, 1190, 1109, 766

NMR (270 MHz, CDCl$_3$, δ, ppm): 8.08–8.01 (2H, m), 7.80–7.74 (2H, m), 4.41 (2H, t), 4.08–3.97 (2H, m), 3.75–3.61 (6H, m), 3.56 (4H, q), 2.00–1.87 (4H, m), 1.22 (6H, t), 1.13 (6H, t)

Example 26

Preparation of 2,3-bis(2-(1-methoxycyclopentyl)ethynyl)quinoxaline (Step 1) Preparation of 2,3-bis(2-(1-hydroxycyclopentyl)ethynyl)quinoxaline To a solution of 1.2 g of 2,3-dichloroquinoxaline dissolved in 18 ml of dimethyl sulfoxide were added 92 mg of copper(I) iodide, 338 mg of bis(triphenylphosphine)palladium(II) chloride and 2.07 ml of 1-ethynylcyclopentanol. After adding 48 ml of triethylamine, the resulting mixture was stirred at room temperature for 17 hours in an atmosphere of argon. Triethylamine was evaporated under a reduced pressure, and the resulting residue was poured into 100 ml of ice-cold water. The thus formed precipitate was collected by filtration, washed with 50 ml of water, dissolved in 200 ml of ethyl acetate and then mixed with 50 ml of water. After removing insoluble materials by filtration, the organic layer was separated from the resulting filtrate, washed with 50 ml of brine and then dried over anhydrous sodium sulfate. The drying agent was removed by filtration, and the resulting filtrate was concentrated.

Thereafter, the resulting residue was purified by chromatography on an alumina column (eluent, hexane/ethyl acetate) and a silica gel column (eluent, 4% methanoldichloromethane) to obtain 1.50 g of 2,3-bis(2-(1-hydroxycyclopentyl)ethynyl)quinoxaline.

Melting point (°C.): 158.2–158.7

IR (KBr, cm$^{-1}$): 3408, 3282, 2970, 2872, 2222, 1398, 1342, 1221, 999, 762

NMR (90 MHz, CDCl$_3$, δ, ppm): 8.04–7.86 (2H, m), 7.78–7.60 (2H, m), 2.79 (2H, br. s), 2.28–1.62 (16H, m)

(Step 2) Preparation of 2,3-bis(2-(1-methoxycyclopentyl)ethynyl)quinoxaline

To a solution of 650 mg of the compound obtained in the above step 1 in 7.2 ml of dimethyl sulfoxide were added 270 mg of potassium hydroxide (85%) and 0.35 ml of iodomethane successively at room temperature. In an atmosphere of argon, the thus prepared mixture was stirred at 40° C. for 7.5 hours. The reaction solution was poured into 100 ml of water and extracted with 100 ml of ethyl acetate. The resulting organic layer was washed twice with 20 ml of water and once with 20 ml of brine and then dried over anhydrous sodium sulfate.

After removing the drying agent by filtration and concentrating the filtrate, the resulting residue was purified by chromatography on a silica gel column (eluent, hexane/ethyl acetate) and an alumina column (eluent, hexane/ethyl acetate) to obtain 420 mg of the title compound.

IR (neat, cm$^{-1}$): 2970, 2943, 2873, 2226, 1342, 1223, 1130, 1117, 1074, 764

NMR (90 MHz, CDCl$_3$, δ, ppm): 8.10–7.89 (2H, m), 7.80–7.59 (2H, m), 3.47 (6H, s), 2.25–1.62 (16H, m)

Example 27

Preparation of 2,3-bis(2-(1-(2-methoxyethoxy)cyclobutyl)ethynyl)quinoxaline (Step 1) Preparation of 1-ethynylcyclobutanol A 8.26 g portion of cyclobutanone was added to 244 ml of ethynylmagnesium bromide (0.5M THF solution) and the mixture was refluxed for 4.5 hours. After spontaneous cooling, 300 ml of saturated ammonium chloride aqueous solution was added to the reaction solution. The aqueous layer separated from that was extracted with 200 ml of tetrahydrofuran, the organic layers were combined and dried over anhydrous sodium sulfate. The drying agent was removed by filtration, and tetrahydrofuran was removed by distillation. Thereafter, the resulting residue was distilled under a reduced pressure to obtain 7.98 g of 1-ethynylcyclobutanol.

Boiling point (°C.): 75–86 (50 mmHg)

NMR (90 MHz, CDCl$_3$, δ, ppm): 2.53 (1H, s), 2.64–2.04 (4H, m), 2.00–1.56 (2H, m)

(Step 2) Preparation of 1-ethynyl-1-(2-methoxyethoxy)cyclobutane

A 4.0 g portion of the compound obtained in the above step 1 was dissolved in 8 ml of dimethyl sulfoxide. To this were added 3.02 g of KOH (85%) and 4.7 ml of 2-bromoethyl methyl ether successively. The thus prepared mixture was stirred at room temperature for 2 hours and then at 40° C. for 2 hours. After adding 60 ml of ice-cold water, the organic layer was separated and dried over anhydrous sodium sulfate. After removing the drying agent by filtration, the resulting filtrate was distilled under a reduced pressure to obtain 4.65 g of 1-ethynyl-1-(2-methoxyethoxy)cyclobutane.

Boiling point (°C.): 80–88 (23 mmHg)

NMR (90 MHz, CDCl$_3$, δ, ppm): 3.70–3.42 (4H, m), 3.39 (3H, s), 2.50 (1H, s), 2.43–2.10 (4H, m), 2.04–1.68 (2H, m)

(Step 3) Preparation of tri-n-butyl-(2-(1-(2-methoxyethoxy)cyclobutyl)ethynyl)tin A 4.65 g of the compound obtained in the above step 2 was dissolved in 45 ml of anhydrous ether. In an atmosphere of argon, 18.9 ml of n-butyllithium (1.6M hexane solution) was added dropwise to the thus prepared solution below −60° C. The resulting mixture was stirred for 20 minutes at the same temperature and then warmed to 0° C. After cooling again to −60° C., to this was added dropwise 33 ml of anhydrous ether solution of 8.2 ml of tri-n-butyltin chloride below −60° C.

After stirring for 18 hours at room temperature, the reaction solution was mixed with 50 ml of ice-cold water and 100 ml of ether. The resulting organic layer was separated, washed twice with 30 ml of water and once with 30 ml of brine and then dried over anhydrous sodium sulfate. After removing the drying agent by filtration, the resulting filtrate was concentrated and distilled under a reduced pressure to obtain 1.3 g of tri-n-butyl-(2-(1-(2-methoxyethoxy)cyclobutyl)ethynyl)tin.

Boiling point (°C.): 143–155 (0.2 mmHg)

NMR (90 MHz, CDCl$_3$, δ, ppm): 3.72–3.44 (4H, m), 3.38 (3H, s), 2.40–2.10 (4H, m), 2.04–0.72 (29H, m)

(Step 4) Preparation of 2,3-bis(2-(1-(2-methoxyethoxy)cyclobutyl)ethynyl)quinoxaline A 1.0 g portion of 2,3-dichloroquinoxaline and 5.57 g of the compound obtained in the above step 3 were dissolved in 25 ml of anhydrous 1,4-dioxane. The thus prepared solution was mixed with 465 mg of tetrakis(triphenylphosphine)palladium(O) and the mixture was refluxed for 9.5 hours in an atmosphere of argon. This was mixed with 60 ml of ice-cold water, 120 ml of ether and 60 ml of saturated potassium fluoride and vigorously stirred. After removing insoluble materials by filtration, the organic layer separated from the resulting filtrate was washed with 50 ml of water and 50 ml of brine and then dried over anhydrous sodium sulfate.

After removing the drying agent by filtration, the resulting filtrate was concentrated and purified by chromatography on a silica gel column (eluent, hexane/ethyl acetate) and an alumina column (eluent, hexane/ethyl acetate) to obtain 1.93 g of the title compound.

IR (neat, cm$^{-1}$): 2989, 2943, 2875, 2220, 1340, 1248, 1126, 766

NMR (90 MHz, CDCl$_3$, δ, ppm): 8.13–7.89 (2H, m), 7.86–7.62 (2H, m), 3.84–3.66 (4H, m), 3.66–3.48 (4H, m), 3.40 (6H, s), 2.70–2.19 (8H, m), 2.13–1.74 (4H, m)

Example 28

Preparation of 2,3-bis(2-(1-(2-ethoxyethoxy)cyclobutyl)ethynyl)quinoxaline (Step 1) Preparation of 1-ethynyl-1-(2-ethoxyethoxy)cyclobutane In the same manner as the procedure of the step 2 of Example 27, 4.0 g of the compound obtained in the step 1 of Example 27 was allowed to react with 6.11 ml of 2-bromoethyl ethyl ether to obtain 6.8 g of 1-ethynyl-1-(2-ethoxyethoxy)cyclobutane.

Boiling point (°C.): 90–103 (18 mmHg)

NMR (90 MHz, CDCl$_3$, δ, ppm): 3.61 (4H, s), 3.54 (2H, q), 2.49 (1H, s), 2.46–2.16 (4H, m), 2.04–1.71 (2H, m), 1.21 (3H, t)

(Step 2) Preparation of tri-n-butyl-(2-(1-(2-ethoxyethoxy)cyclobutyl)ethynyl)tin Using 6.8 g of the compound obtained in the above step 1, the procedure of the step 3 of Example 27 was repeated to obtain 15.2 g of tri-n-butyl-(2-(1-(2-ethoxyethoxy)cyclobutyl)ethynyl)tin.

Boiling point (°C.): 145–161 (0.2 mmHg)

NMR (90 MHz, CDCl$_3$, δ, ppm): 3.62 (4H, s), 3.54 (2H, q), 2.40–2.07 (4H, m), 2.07–0.69 (32H, m)

(Step 3) Preparation of 2,3-bis(2-(1-(2-ethoxyethoxy)cyclobutyl)ethynyl)quinoxaline In the same manner as the procedure of the step 4 of Example 27, 1.0 g of 2,3-dichloroquinoxaline was allowed to react with 4.59 g of the compound obtained in the above step 2 to obtain 1.98 g of the title compound.

IR (neat, cm$^{-1}$): 2976, 2943, 2870, 2222, 1394, 1340, 1248, 1122, 1068, 766

NMR (90 MHz, CDCl$_3$, δ, ppm): 8.10–7.89 (2H, m), 7.80–7.59 (2H, m), 3.81–3.45 (8H, m), 3.56 (4H, q), 2.70–2.13 (8H, m), 2.13–1.62 (4H, m), 1.21 (6H, t)

Example 29

Preparation of 2-chloro-3-(3-ethoxy-1-butynyl)quinoxaline

A mixture of 3 g of 2,3-dichloroquinoxaline, 5.83 g of tri-n-butyl-(3-ethoxy-1-butynyl)tin, 76.5 ml of anhydrous 1,4-dioxane and 697 mg of Pd(PPh$_3$)$_4$ was refluxed for 4 hours in an atmosphere of nitrogen. The reaction mixture was poured into 200 ml of ice-cold water, mixed with 400 ml of ethyl acetate and 200 ml of saturated potassium fluoride aqueous solution and then vigorously stirred for 15 minutes. After removing insoluble materials by filtration, the organic layer separated from the resulting filtrate was washed with brine and dried over anhydrous sodium sulfate.

After removing the drying agent by filtration and evaporating the solvent under a reduced pressure, the resulting residue was purified by chromatography on a silica gel column (eluent, hexane/ethyl acetate) to obtain 2.7 g of the title compound.

Melting point (°C.): 49.3–50.4

IR (KBr, cm$^{-1}$): 2984, 2891, 2225, 1330, 1113, 1081, 765

NMR (90 MHz, CDCl$_3$, δ, ppm): 8.16–7.86 (2H, m), 7.86–7.62 (2H, m), 4.53 (1H, q), 4.12–3.76 (1H, m), 3.76–3.40 (1H, m), 1.63 (3H, d), 1.29 (3H, t)

Example 30

Preparation of 2-t-butyl-3-(3-(2-methoxyethoxy)-1-propynyl)quinoxaline (Step 1) Preparation of 2-t-butyl-3,4-dihydro-3-oxo-quinoxaline A 83 ml portion of ethanol was added to a mixture of 4.14 g of trimethylpyruvic acid synthesized in accordance with the method of Jaeger et al. (*J. Am. Chem. Soc.*, pp.717–732, 1979) and 3.02 g of o-phenylenediamine. The thus prepared mixture was refluxed for 3 hours in an atmosphere of nitrogen. By concentrating the resulting reaction solution, 3.15 g of 2-t-butyl-3, 4-dihydro-3-oxoquinoxaline was obtained.

Melting point (°C.): 204.1–206.8

IR (KBr, cm$^{-1}$): 3007, 2968, 2954, 2893, 2846, 1649, 1612, 1552, 1080, 752

NMR (90 MHz, CDCl$_3$, δ, ppm): 11.75 (1H, br. s), 7.92–7.72 (1H, m), 7.56–7.24 (3H, m), 1.53 (9H, s)

(Step 2) Preparation of 3-chloro-2-t-butylquinoxaline

A 16 ml portion of phosphorus oxychloride was added to 3.5 g of the compound obtained in the above step 1 and the mixture was refluxed for 1.5 hours. The reaction solution was poured into 100 ml of ice-cold water and extracted with 200 ml of ethyl acetate. The organic layer was washed with 50 ml of water and 50 ml of brine and then dried over anhydrous sodium sulfate. After removing the drying agent by filtration, the resulting filtrate was concentrated and the residue was purified by chromatography on a silica gel column (eluent, dichloromethane) to obtain 3.8 g of 2-chloro-3-t-butylquinoxaline.

Melting point (°C.): 36.7–37.2

IR (KBr, cm$^{-1}$): 2960, 1560, 1396, 1363, 1292, 1169, 1103, 1022, 1003, 756, 596

NMR (90 MHz, CDCl$_3$, δ, ppm): 8.13–7.86 (2H, m), 7.83–7.62 (2H, m), 1.62 (9H, s)

(Step 3) Preparation of 2-t-butyl-3-(3-(2-methoxyethoxy)-1-propynyl)quinoxaline

Using 1.0 g of the compound obtained in the above step 2 and 1.83 g of tri-n-butyl-(3-(2-methoxyethoxy)-1-propynyl)tin, the procedure of Example 4 was repeated to obtain 1.10 g of the title compound.

IR (KBr, cm$^{-1}$): 2956, 2929, 2872, 2229, 1475, 1365, 1352, 1333, 1211, 1142, 1128, 1101, 1084, 762

NMR (90 MHz, CDCl$_3$, δ, ppm): 8.10–7.86 (2H, m), 7.83–7.59 (2H, m), 4.59 (2H, s), 3.93–3.72 (2H, m), 3.72–3.51 (2H, m), 3.42 (3H, s), 1.65 (9H, s)

Example 31

Preparation of 2,3-bis(3-ethoxy-1-butynyl)-6-hydroxymethylquinoxaline (Step 1) Preparation of 2,3-dichloro-6-hydroxymethylquinoxaline To a suspension of 25.3 g portion of 2,3-dichloroquinoxaline-6-carbonyl chloride synthesized in accordance with the procedure disclosed in JP-A 57-98274 in 400 ml of anhydrous 1,4-dioxane, was added 14.0 g of sodium borohydride, and the mixture was stirred at room temperature for 10 minutes in an atmosphere of nitrogen. With cooling on an ice bath, to this was added dropwise 100 ml of water. Thereafter, 1,4-dioxane was evaporated under a reduced pressure, and the resulting residue was purified by chromatography on a silica gel column (eluent, hexane/ethyl acetate) to obtain 8.75 g of 2,3-dichloro-6-hydroxymethylquinoxaline.

Melting point (°C.): 156.3–158.1

IR (KBr, cm$^{-1}$): 3385, 3350, 3304, 3255, 3207, 1676, 1624, 1610, 1408, 1281, 1269, 1161, 1120, 1009, 856, 598

NMR (90 MHz, DMSO-d$_6$, δ, ppm): 8.10–7.76 (3H, m), 5.60 (1H, t), 4.77 (2H, d)

(Step 2) Preparation of 2,3-bis(3-ethoxy-1-butynyl)-6-hydroxymethylquinoxaline

Using 3.0 g of the compound obtained in the above step 1 and 15.2 g of the compound obtained in the step 2 of Example 10, the procedure of the step 3 of Example 10 was repeated to obtain 2.25 g of the title compound.

Melting point (°C.): 73.5–74.5

IR (KBr, cm$^{-1}$): 3340, 2980, 2933, 2868, 2220, 1443, 1369, 1344, 1323, 1190, 1153, 1109, 1070, 1043, 825

NMR (90 MHz, CDCl$_3$, δ, ppm): 8.02 (1H, d), 7.97 (1H, d), 7.74 (1H, dd), 4.93 (2H, d), 4.51 (2H, q), 4.16–3.79 (2H, m), 3.73–3.36 (2H, m), 1.62 (6H, d), 1.28 (6H, t)

Example 32

Preparation of 2,3-bis(3-ethoxy-1-butynyl)-6-methoxymethylquinoxaline (Step 1) Preparation of 2,3-dichloro-6-methoxymethylquinoxaline To a suspension of 3.0 g of the compound obtained in the step 1 of Example 31 in 50 ml of anhydrous 1,4-dioxane was added 2.9 g of trimethyloxonium tetrafluoroborate. After stirring at room temperature for 4 hours in an atmosphere of nitrogen, 1.0 g of trimethyloxonium tetrafluoroborate was again added, and the mixture was stirred at 40° C. for 2 hours. The reaction solution was poured into water and extracted with ethyl acetate. The ethyl acetate layer was washed with water and dried over anhydrous sodium sulfate.

After evaporating the solvent under a reduced pressure, the resulting residue was purified by chromatography on a silica gel column (eluent, hexane/ethyl acetate) to afford 0.92 g of 2,3-dichloro-6-methoxymethylquinoxaline.

NMR (90 MHz, CDCl$_3$, δ, ppm): 8.00 (1H, d), 7.96 (1H, s), 7.77 (1H, dd), 4.67 (2H, s), 3.47 (3H, s)

(Step 2) Preparation of 2,3-bis(3-ethoxy-1-butynyl)-6-methoxymethylquinoxaline

In accordance with the procedure of the step 3 of Example 10, 890 mg of the compound obtained in the above step 1 was allowed to react with 3.9 g of the compound obtained in the step 2 of Example 10 to afford 720 mg of the title compound.

IR (KBr, cm$^{-1}$): 2981, 2935, 2893, 2872, 2224, 1622, 1444, 1402, 1383, 1369, 1342, 1196, 1159, 1109, 1074, 831

NMR (90 MHz, CDCl$_3$, δ, ppm): 8.02 (1H, d), 7.97 (1H, d), 7.76 (1H, dd), 4.66 (2H, s), 4.51 (2H, q), 4.14–3.79 (2H, m), 3.73–3.39 (2H, m), 3.46 (3H, s), 1.62 (6H, d), 1.28 (6H, t)

Example 33

Preparation of 6-acetyl-2,3-bis(3-ethoxy-1-butynyl)quinoxaline (Step 1) Preparation of 2,3-dichloro-6-bis(ethoxycarbonyl)acetylquinoxaline With cooling on an ice bath, a tetrahydrofuran (49.1 ml) solution of 25.4 g of 2,3-dichloroquinoxaline-6-carbonyl chloride synthesized in accordance with the method disclosed in Example 1 of JP-A 57-98274 was added to a solution containing 19.6 g of diethylmagnesium malonate prepared in accordance with the method of Chapman et al. (*J. Chem. Soc.*, (C), pp.2747–2751, 1968). After stirring at the same temperature for 1.5 hours, to resulting mixture was added 500 ml of ice-cold water and 1.5 liters of ethyl acetate. After adding 200 ml of 10% sulfuric acid, the organic layer was separated and the aqueous layer was extracted with 300 ml of ethyl acetate.

The organic layers were combined, washed twice with 200 ml of water and 100 ml of brine and then dried over anhydrous sodium sulfate. The drying agent was removed by filtration, and the resulting filtrate was concentrated. The residue was dispersed in ether, mixed with hexane, collected by filtration and then air-dried to obtain 28.5 g of 2,3-dichloro-6-bis(ethoxycarbonyl)acetylquinoxaline.

Melting point (°C.): 102.1–103.1

IR (KBr, cm$^{-1}$): 1741, 1686, 1369, 1308, 1286, 1269, 1234, 1178, 1161, 1151, 1140, 1119, 1099, 1001, 854, 627

NMR (90 MHz, CDCl$_3$, δ, ppm): 8.50 (1H, d), 8.35 (1H, dd), 8.11 (1H, d), 5.37 (1H, s), 4.30 (4H, q), 1.28 (6H, t)

(Step 2) Preparation of 6-acetyl-2,3-dichloroquinoxaline

A 2.0 g portion of the compound obtained in the above step 1 was dissolved in 4.7 ml of N,N-dimethylformamide. To this were added 0.61 g of sodium chloride and 0.37 ml of water. After stirring at 140° C. for 2 hours in an atmosphere of nitrogen, the reaction solution was poured into 50 ml of ice-cold water and extracted with 200 ml of ethyl acetate. The organic layer was washed 3 times with 25 ml of water and once with brine and then dried over anhydrous sodium sulfate. After removing the drying agent by filtration, the filtrate was concentrated.

Thereafter, the residue was purified by chromatography on a silica gel column (eluent, hexane/ethyl acetate) to obtain 0.67 g of 6-acetyl-2,3-dichloroquinoxaline.

Melting point (°C.): 135.4–137.7

IR (KBr, cm$^{-1}$): 1684, 1365, 1292, 1269, 1265, 1151, 1120, 999, 841, 638, 617

NMR (90 MHz, CDCl$_3$, δ, ppm): 8.58 (1H, d), 8.37 (1H, dd), 8.09 (1H, d), 2.76 (3H, s)

(Step 3) Preparation of 6-acetyl-2,3-bis(3-ethoxy-1-butynyl)quinoxaline

In accordance with the procedure of the step 3 of Example 10, 2.0 g of the compound obtained in the above step 2 was allowed to react with 8.99 g of the compound obtained in the step 2 of Example 10 to obtain 2.19 g of the title compound.

Melting point (°C.): 70.8–72.8

IR (KBr, cm$^{-1}$): 2980, 2864, 2222, 1689, 1363, 1340, 1300, 1194, 1151, 1107, 1072, 845

NMR (90 MHz, CDCl$_3$, δ, ppm): 8.59 (1H, d), 8.32 (1H, dd), 8.07 (1H, d), 4.52 (2H, q), 4.17–3.78 (2H, m), 3.78–3.39 (2H, m), 2.74 (3H, s), 1.63 (6H, d), 1.28 (6H, t)

Example 34

Preparation of 6-bis(ethoxycarbonyl)acetyl-2,3-bis(3-ethoxy-1-butynyl)quinoxaline A 27 ml portion of dimethyl sulfoxide was added to a mixture of 3.5 g of the compound obtained in the step 1 of Example 33, 2.55 g of 3-ethoxy-1-butyne, 510 mg of bis-(triphenylphosphine)palladium(II) chloride and 140 mg of copper(I) iodide. After adding 73 ml of triethylamine, the thus prepared mixture was stirred at room temperature for 6 hours in an atmosphere of nitrogen. The reaction solution was concentrated, and the residue was poured into 200 ml of 3N hydrochloric acid under ice cooling and then extracted with 500 ml of ethyl acetate.

The organic layer was washed twice with 100 ml of water and once with brine and then dried over anhydrous sodium sulfate. The drying agent was removed by filtration, and the filtrate was concentrated. The residue was purified by chromatography on a silica gel column (eluent, hexane/ethyl acetate) and crystallized from ether-hexane. The crystals were collected by filtration and air-dried to obtain 820 mg of the title compound.

Melting point (°C.): 63.2–64.0

IR (KBr, cm$^{-1}$): 2980, 2222, 1741, 1726, 1689, 1340, 1321, 1306, 1174, 1144, 1115

NMR (90 MHz, CDCl$_3$, δ, ppm): 8.50 (1H, d), 8.31 (1H, dd), 8.11 (1H, d), 5.39 (1H, s), 4.53 (2H, q), 4.29 (4H, q), 4.20–3.78 (2H, m), 3.78–3.36 (2H, m), 1.63 (6H, d), 1.28 (12H, t)

Example 35

Preparation of 2,3-bis(3-ethoxy-1-butynyl)-6-formylquinoxaline (Step 1) Preparation of 2,3-dichloro-6-formylquinoxaline A 46 g portion of the compound obtained in the step 1 of Example 31 was dissolved in a mixture of 160 ml dichloromethane and 160 ml dimethylformamide, and to this solution was added 126 g of manganese dioxide and the mixture was stirred at room temperature for 16 hours. Insoluble materials were removed by filtration, and the thus separated insoluble materials were washed with ethyl acetate. The filtrate and the washings were combined and washed with water. The organic layer was dried over anhydrous sodium sulfate, and the solvent was evaporated under a reduced pressure.

Thereafter, the resulting residue was purified by chromatography on a silica gel column (eluent, hexane/dichloromethane) to obtain 7.3 g of 2,3-dichloro-6-formylquinoxaline.

Melting point (°C.): 171.5–174.0

IR (KBr, cm$^{-1}$): 1701, 1267, 1122, 1007, 851, 843, 783

NMR (90 MHz, CDCl$_3$, δ, ppm): 10.3 (1H, s), 8.51 (1H, d), 8.31 (1H, dd), 8.14 (1H, d)

(Step 2) Preparation of 2,3-bis(3-ethoxy-1-butynyl) formylquinoxaline

In accordance with the procedure of the step 3 of Example 10, 3.14 g of the compound obtained in the above step 1 was allowed to react with 11.7 g of the compound obtained in the step 2 of Example 10 to obtain 2.6 g of the title compound.

Melting point (°C.): 85.2–86.3

IR (KBr, cm$^{-1}$): 2978, 2943, 2895, 2868, 2222, 1699, 1335, 1151, 1140, 1109, 1072, 841, 781

NMR (90 MHz, CDCl$_3$, δ, ppm): 10.2 (1H, s), 8.48 (1H, d), 8.26 (1H, dd), 8.11 (1H, d), 4.52 (2H, q), 4.16–3.81 (2H, m), 3.75–3.39 (2H, m), 1.63 (6H, d), 1.29 (6H, t)

Examples 36 and 37

Preparation of 6-(2-hydroxyiminoethyl)-2,3-bis(3-ethoxy-1-butynyl)quinoxaline (anti form, Example 36; syn form, Example 37)

A 800 mg portion of the compound obtained in the step 3 of Example 33 and 170 mg of hydroxylamine hydrochloride were added to 8 ml of methanol. To this was added 0.20 ml of pyridine with cooling on an ice bath and then the mixture was stirred at room temperature for 2 hours. The reaction solution was poured into 20 ml of ice-cold water, mixed with 30 ml of 1N hydrochloric acid and then extracted with 200 ml of ethyl acetate. The organic layer was washed with 50 ml of water and 50 ml of brine and then dried over anhydrous sodium sulfate. The drying agent was removed by filtration, and the filtrate was concentrated.

The resulting residue was purified by chromatography on a silica gel column (eluent, hexane/ethyl acetate) and dispersed in hexane. Thereafter, the thus formed crystals were collected by filtration and air-dried to obtain 579 mg of anti form and 110 mg of syn form of the title compound.

(1) Anti form (Example 36)

IR (KBr, cm$^{-1}$): 3190, 2980, 2868, 2224, 1369, 1348, 1325, 1186, 1109, 1018, 839

NMR (90 MHz, DMSO-d$_6$, δ, ppm): 11.76 (1H, s), 8.29 (1H, dd), 8.19 (1H, d), 7.99 (1H, d), 4.59 (2H, q), 3.93–3.57 (2H, m), 3.57–3.21 (2H, m), 2.30 (3H, s), 1.51 (6H, d), 1.20 (6H, t)

(2) Syn form (Example 37)

IR (KBr, cm$^{-1}$): 3196, 2981, 2870, 2224, 1344, 1188, 1113, 1074, 1038, 943

NMR (90 MHz, DMSO-d$_6$, δ, ppm): 11.02 (1H, s), 8.19 (1H, s), 8.05 (2H, s), 4.60 (2H, q), 4.02–3.69 (2H, m), 3.69–3.36 (2H, m), 2.26 (3H, s), 1.51 (6H, d), 1.20 (6H, t)

Examples 38 and 39

Preparation of 6-(2-methoxyiminoethyl)-2,3-bis(3-ethoxy-1-butynyl)quinoxaline (anti form, Example 38; syn form, Example 39)

A 800 mg portion of the compound obtained in the step 3 of Example 33 and 202 mg of methoxylamine hydrochloride were added to 8 ml of methanol. To this was added 0.20 ml of pyridine with cooling on an ice bath and then the mixture was stirred at room temperature for 2 hours. The reaction solution was poured into 30 ml of ice-cold water, mixed with 30 ml of 1N hydrochloric acid and then extracted with 150 ml of ethyl acetate. The organic layer was washed with 30 ml of water and 30 ml of brine and then dried over anhydrous sodium sulfate. The drying agent was removed by filtration, and the filtrate was concentrated.

Thereafter, the resulting residue was purified by chromatography on a silica gel column (eluent, hexane/ethyl acetate) to obtain 668 mg of anti form and 74 mg of syn form of the title compound.

(1) Anti form (Example 38)

IR (KBr, cm$^{-1}$): 2980, 2933, 2868, 2222, 1344, 1325, 1180, 1113, 1072, 1047, 897

NMR (90 MHz, CDCl$_3$, δ, ppm): 8.31 (1H, dd), 8.15 (1H, d), 7.97 (1H, d), 4.52 (2H, q), 4.06 (3H, s), 4.16–3.76 (2H, m), 3.76–3.36 (2H, m), 2.32 (3H, s), 1.62 (6H, d), 1.28 (6H, t)

(2) Syn form (Example 39)

IR (KBr, cm$^{-1}$): 2980, 2937, 2897, 2224, 1340, 1184, 1111, 1088, 1074, 1049, 905

NMR (90 MHz, CDCl$_3$, δ, ppm): 8.13 (1H, d), 8.04 (1H, d), 7.95 (1H, dd), 4.52 (2H, q), 3.89 (3H, s), 4.20–3.78 (2H, m), 3.78–3.36 (2H, m), 2.31 (3H, s), 1.63 (6H, d), 1.28 (6H, t)

Example 40

Preparation of 6-carbamoyl-2,3-bis(3-ethoxy-1-butynyl)quinoxaline (Step 1) Preparation of 6-carbamoyl-2,3-dichloroquinoxaline A 12.7 g portion of 2,3-dichloroquinoxaline-6-carbonyl chloride prepared by the procedure of Example 1 disclosed in JP-A 57-98274 was suspended in 100 ml of ether. With cooling on an ice bath, the suspension was mixed with 20 ml of 29% aqueous ammonia and stirred for 20 minutes. After acidifying with 6N hydrochloric acid, the thus formed crystals were collected by filtration, washed with 100 ml of ethanol/ether (2/3) and 50 ml of ether, air-dried and then extracted with acetone. Insoluble materials were removed by filtration, and the resulting filtrate was concentrated and washed with acetone/ether (1/4).

Thereafter, the resulting residue was air-dried and purified by chromatography on a silica gel column (eluent, hexane/ethyl acetate) to obtain 5.93 g of 6-carbamoyl-2,3-dichloroquinoxaline.

Melting point (°C.): 249.1–250.9

IR (KBr, cm$^{-1}$): 3386, 3255, 1678, 1624, 1408, 1267, 1159, 1120, 1009, 600

NMR (90 MHz, DMSO-d$_6$, δ, ppm): 8.57 (1H, d), 8.37 (1H, br. s), 8.35 (1H, dd), 8.13 (1H, d), 7.76 (1H, br. s)

(Step 2) Preparation of 6-carbamoyl-2,3-bis(3-ethoxy-1-butynyl)quinoxaline

In accordance with the procedure of the step 3 of Example 10, 1.0 g of the compound obtained in the above step 1 was allowed to react with 4.48 g of the compound obtained in the step 2 of Example 10, to obtain 700 mg of the title compound.

Melting point (°C.): 143.0–144.8

IR (KBr, cm$^{-1}$): 3427, 3176, 2981, 2222, 1680, 1404, 1342, 1196, 1107

NMR (90 MHz, DMSO-d$_6$, δ, ppm): 8.54 (1H, d), 8.34 (1H, br. s), 8.31 (1H, dd), 8.09 (1H, d), 7.74 (1H, br. s), 4.61 (2H, q), 4.08–3.30 (4H, m), 1.52 (6H, d), 1.20 (6H, t)

Example 41

Preparation of 6-cyano-2,3-bis(3-ethoxy-1-butynyl)quinoxaline (Step 1) Preparation of 6-cyano-2,3-dichloroquinoxaline A 2.75 g portion of the compound obtained in the step 1 of Example 40 was suspended in 19.5 ml of N,N-dimethylformamide. To this was added 2.1 ml of phosphorus oxychloride with cooling on an ice bath and the mixture was stirred at room temperature for 1 hour. The reaction solution was poured into 100 ml of ice-cold water and extracted with 300 ml of ethyl acetate. The organic layer was washed with 50 ml of water and 50 ml of brine and then dried over anhydrous sodium sulfate. The drying agent was removed by filtration, and the resulting filtrate was concentrated.

Thereafter, the resulting residue was dispersed in ether, collected by filtration and then air-dried to obtain 1.9 g of 6-cyano-2,3-dichloroquinoxaline.

Melting point (°C.): 237.8–238.7

IR (KBr, cm$^{-1}$): 3072, 3043, 2231, 1259, 1180, 1169, 1124, 1005, 856

NMR (90 MHz, CDCl$_3$, δ, ppm): 8.40 (1H, d), 8.16 (1H, d), 7.95 (1H, dd)

(Step 2) Preparation of 6-cyano-2,3-bis(3-ethoxy-1-butynyl)quinoxaline

In accordance with the procedure of the step 3 of Example 10, 1.0 g of the compound obtained in the above step 1 was allowed to react with 4.84 g of the compound obtained in the step 2 of Example 10 to obtain 810 mg of the title compound.

Melting point (°C.): 67.5–68.6

IR (KBr, cm$^{-1}$): 2980, 2934, 2868, 2230, 2221, 1395, 1339, 1323, 1193, 1113, 1072, 843

NMR (90 MHz, CDCl₃, δ, ppm): 8.39 (1H, d), 8.13 (1H, d), 7.88 (1H, dd), 4.52 (2H, q), 4.14–3.76 (2H, m), 3.76–3.38 (2H, m), 1.62 (6H, d), 1.28 (6H, t)

Example 42

Preparation of 2,3-bis(3-(2-ethoxyethoxy)-1-hexynyl)quinoxaline (Step 1) Preparation of 2,3-diiodoquinoxaline A 20 g portion of 2,3-dichloroquinoxaline was dissolved in 200 ml of acetone. To this were added 66 g of sodium iodide and 3.4 ml of 57% hydroiodic acid and the mixture was stirred at 50° C. for 3 hours. The reaction solution was poured into 400 ml of water and extracted five times with 400 ml of dichloromethane. The dichloromethane layers were combined, washed with 2% sodium thiosulfate aqueous solution, water and brine and then dried over anhydrous sodium sulfate.

After evaporating the solvent under a reduced pressure, the resulting residue was dissolved in a mixture of dichloromethane and acetone and subjected to decolorization using activated charcoal. Thereafter, the crystals thus formed were recrystallized from ethyl acetate to obtain 19.8 g of 2,3-diiodoquinoxaline as yellow needles.

Melting point (°C.): 192.4–193.5

IR (KBr, cm⁻¹): 3075, 1554, 1539, 1500, 1234, 1161, 1124, 1078, 1051, 945, 858, 766, 608

NMR (270 MHz, CDCl₃, δ, ppm): 8.05–7.99 (2H, m), 7.82–7.76 (2H, m)

(Step 2) Preparation of 3-(2-ethoxyethoxy)-1-hexyne

In accordance with the procedure of the step 1 of Example 10, 21.8 g of 1-hexyn-3-ol was allowed to react with 37.2 g of 2-bromoethyl ethyl ether to obtain 16.9 g of 3-(2-ethoxyethoxy)-1-hexyne.

Boiling point (°C.): 90–95 (25 mmHg; colorless oil)

NMR (90 MHz, CDCl₃, δ, ppm): 4.10 (1H, dt), 3.96–3.73 (1H, m), 3.69–3.54 (3H, m), 3.54 (2H, q), 2.41 (1H, d), 1.89–1.37 (4H, m), 1.21 (3H, t), 0.93 (3H, t)

(Step 3) Preparation of 2,3-bis(3-(2-ethoxyethoxy)-1-hexynyl)quinoxaline

A 1.1 g portion of the compound obtained in the above step 1 was suspended in 10 ml of anhydrous acetonitrile, and to this were added 10 ml of triethylamine, 21.9 mg of copper(I) iodide and 113 mg of bis(triphenylphosphine)palladium(II) chloride and then the mixture was stirred at room temperature for 10 minutes in an atmosphere of argon. At room temperature, to this was added dropwise a solution of 2.94 g of the compound obtained in the above step 3 in 10 ml of anhydrous acetonitrile. After stirring for 4.5 hours at room temperature, the solvent was evaporated under a reduced pressure. The resulting residue was mixed with 50 ml of water and extracted three times with 50 ml of ethyl acetate. The ethyl acetate layers were combined, washed three times with 50 ml of water, once with 50 ml of 1N hydrochloric acid and once with brine and then dried over anhydrous sodium sulfate.

After evaporating the solvent under a reduced pressure, the resulting residue was purified by chromatography on a silica gel column (eluent, hexane/ethyl acetate) and an alumina column (eluent, hexane/ethyl acetate) to obtain 1.18 g of the title compound.

IR (neat, cm–1): 2962, 2931, 2870, 2226, 1338, 1117, 1095, 766

NMR (90 MHz, CDCl₃, δ, ppm): 8.16–7.95 (2H, m), 7.89–7.65 (2H, m), 4.48 (2H, t), 4.20–3.88 (2H, m), 3.84–3.51 (6H, m), 3.55 (4H, q), 1.84–1.76 (4H, m), 1.74–1.35 (4H, m), 1.21 (6H, t), 0.98 (6H, t)

Example 43

Preparation of 2,3-bis(3-(2-methoxyethoxy)-3-methyl-1-butynyl)quinoxaline (Step 1) Preparation of 3-(2-methoxyethoxy)-3-methyl-1-butyne In accordance with the procedure of the step 1 of Example 10, and using 21.7 g of 3-methyl-1-butyn-3-ol and 39.4 g of 2-bromoethyl methyl ether, 22.6 g of 3-(2-methoxyethoxy)-3-methyl-1-butyne was obtained.

Boiling point (°C.): 123–150 (colorless oil)

NMR (90 MHz, CDCl₃, δ, ppm): 3.81–3.66 (2H, m), 3.60–3.47 (2H, m), 3.39 (3H, s), 2.41 (1H, s), 1.49 (6H, s)

(Step 2) Preparation of tri-n-butyl-(3-(2-methoxyethoxy)-3-methyl-1-butynyl)tin

In accordance with the procedure of the step 2 of Example 10, and using 13.1 g of the compound obtained in the above step 1, 29.5 g of g of tri-n-butyl-(3-(2-methoxyethoxy)-3-methyl-1-butynyl)tin was obtained.

Boiling point (°C.): 115–125 (0.1 mmHg; colorless oil)

NMR (90 MHz, CDCl₃, δ, ppm): 3.84–3.66 (2H, m), 3.62–3.47 (2H, m), 3.38 (3H, s), 1.74–1.16 (18H, m), 1.46 (6H, s), 1.11–0.75 (9H, m)

(Step 3) Preparation of 2,3-bis(3-(2-methoxyethoxy)-3-methyl-1-butynyl)quinoxaline In accordance with the procedure of the step 3 of Example 10, and using 7.14 g of the compound obtained in the above step 2, 1.86 g of the title compound was obtained.

IR (neat, cm⁻¹): 2929, 2875, 2818, 2227, 1336, 1230, 1186, 1163, 1130, 1084, 974, 766

NMR (90 MHz, CDCl₃, δ, ppm): 8.10–7.95 (2H, m), 7.84–7.67 (2H, m), 3.96–3.75 (4H, m), 3.69–3.47 (4H, m), 3.40 (6H, s), 1.68 (12H, s)

Example 44

Preparation of 2,3-bis(3-(2-ethoxyethoxy)-3-methyl-1-butynyl)quinoxaline (Step 1) Preparation of 3-(2-ethoxyethoxy)-3-methyl-1-butyne In accordance with the procedure of the step 1 of Example 10, and using 34.5 g of 3-methyl-1-butyn-3-ol and 69.0 g of 2-bromoethyl ethyl ether, 40.9 g of 3-(2-ethoxyethoxy)-3-methyl-1-butyne was obtained.

Boiling point (°C.): 140–165 (colorless oil)

NMR (90 MHz, CDCl₃, δ, ppm): 3.81–3.69 (2H, m), 3.66–3.56 (2H, m), 3.55 (2H, q), 2.40 (1H, s), 1.48 (6H, s), 1.21 (3H, t)

(step 2) Preparation of 2,3-bis(3-(2-ethoxyethoxy)-3-methyl-1-butynyl)quinoxaline A 1.1 g portion of 2,3-diiodoquinoxaline was suspended in 8.6 ml of dimethyl sulfoxide. To this was added 22 ml of triethylamine, 21.9 mg of copper(I) iodide and 113 mg of bis(triphenylphosphine)palladium(II) chloride and the mixture was stirred at room temperature for 10 minutes in an atmosphere of argon. At room temperature, to this was slowly added 2.7 g of the compound obtained in the above step 1. After stirring at room temperature for 6 hours, the reaction solution was poured into 110 ml of water and extracted three times with 110 ml of ethyl acetate. The ethyl acetate layers were combined, washed three times with 110 ml of water, once with 110 ml of 1N hydrochloric acid and once with 110 ml of brine and then dried over anhydrous sodium sulfate.

After evaporating the solvent under a reduced pressure, the resulting residue was purified by chromatography on a silica gel column (eluent, hexane/ethyl acetate) and an alumina column (eluent, dichloromethane) to obtain 792 mg of the title compound.

IR (neat, cm$^{-1}$): 2981, 2931, 2870, 2227, 1336, 1232, 1163, 1126, 1086, 978, 766

NMR (90 MHz, CDCl$_3$, δ, ppm): 8.14–7.95 (2H, m), 7.86–7.69 (2H, m), 3.90 (4H, t),3.64 (4H, t), 3.55 (4H, q), 1.67 (12H, s), 1.20 (6H, t)

Examples 45 to 154

Compounds of Examples 45 to 154 were prepared in accordance with the Preparation process represented by the reaction scheme A (step 4 of Example 1). Particularly, compounds of Examples 62 to 68 and 74 to 84 were prepared in accordance with the procedures of Examples 3 and 4.

Figure 2:
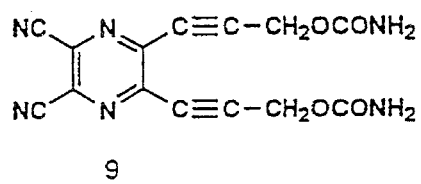
FIG. 2 is a drawing showing structural formulas of compounds 9 to 16 of the present invention.
Figure 2:
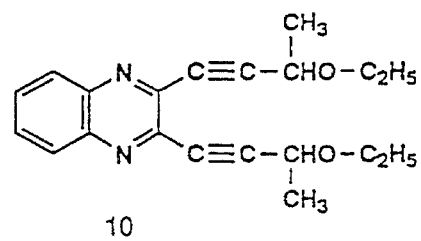
Figure 2:
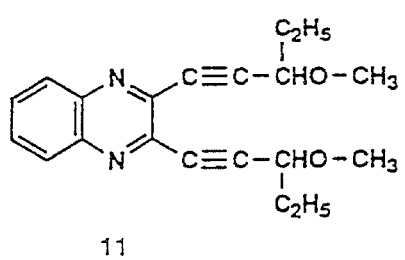
Figure 2:
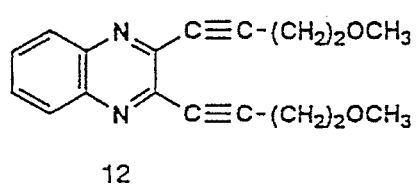
Figure 2:
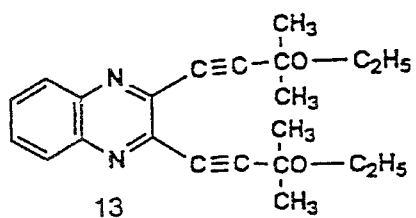
Figure 2:
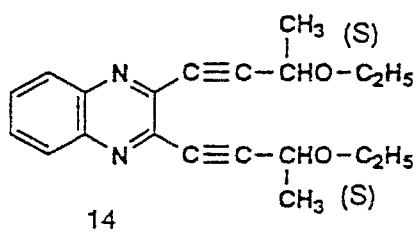
Figure 2:
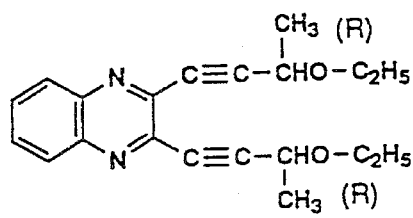
Figure 2:
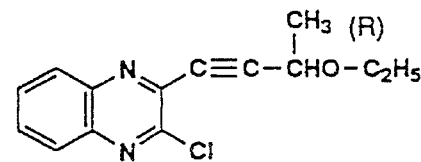
Figure 3:
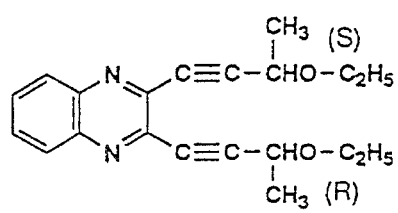
FIG. 3 is a drawing showing structural formulas of compounds 17 to 24 of the present invention.
Figure 3:
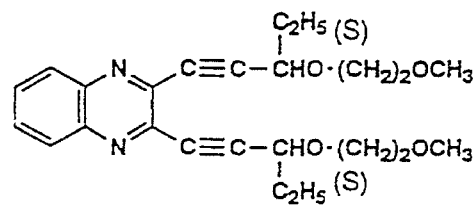
Figure 3:
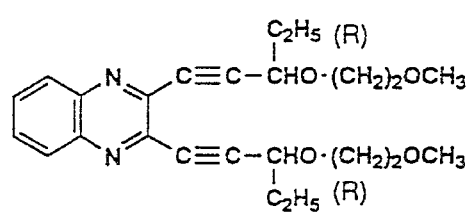
Figure 3:
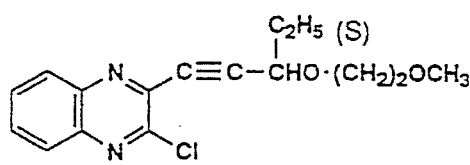
Figure 3:
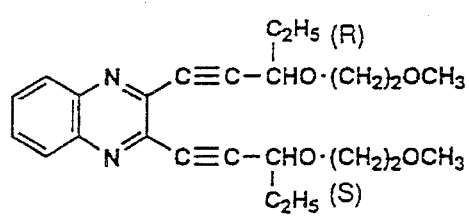
Figure 3:
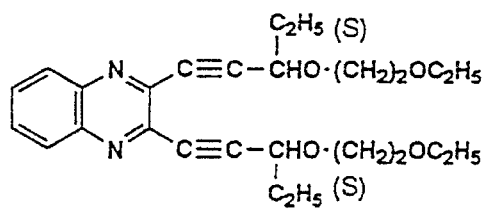
Figure 3:
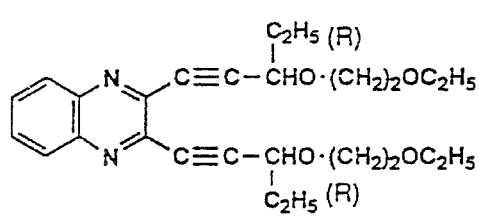
Figure 3:
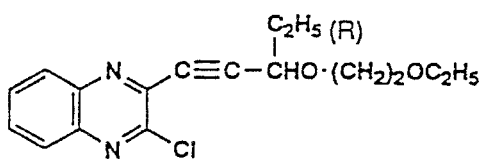
Figure 4:
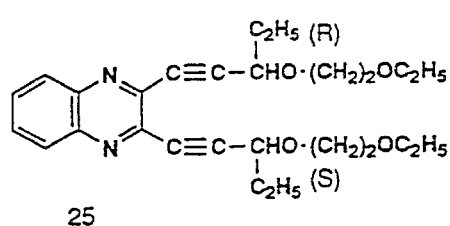
FIG. 4 is a drawing showing structural formulas of compounds 25 to 32 of the present invention
Figure 4:
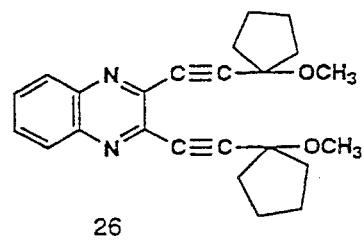
Figure 4:
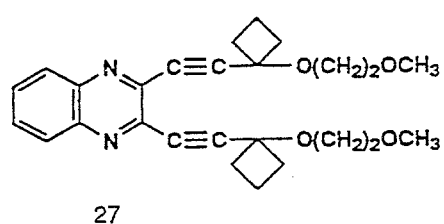
Figure 4:
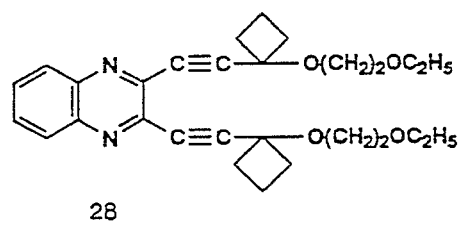
Figure 4:
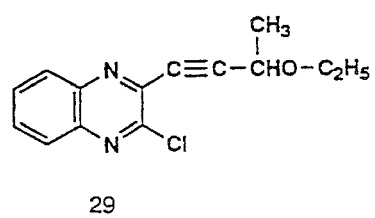
Figure 4:
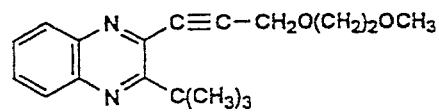
Figure 4:
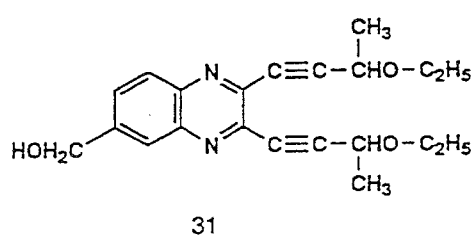
Figure 4:
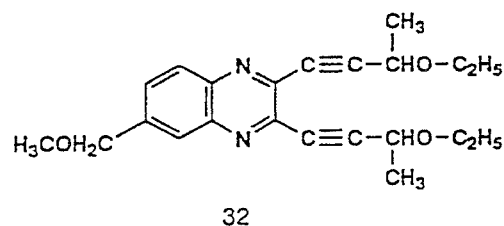
Figure 5:
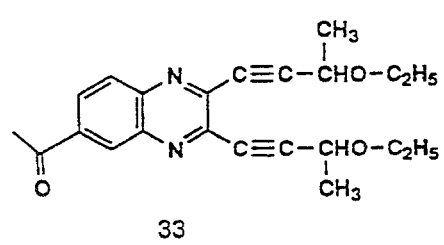
FIG. 5 is a drawing showing structural formulas of compounds 33 to 40 of the present invention
Figure 5:
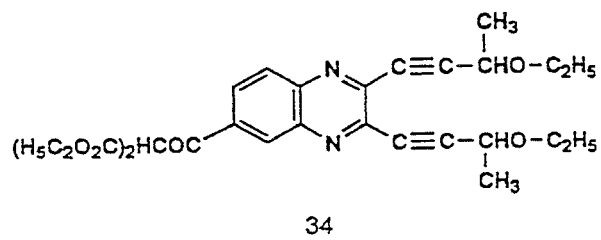
Figure 5:
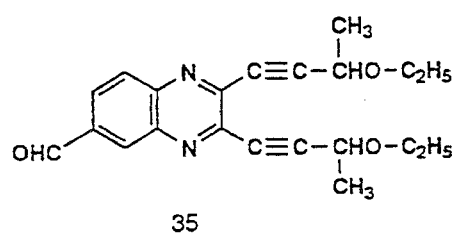
Figure 5:
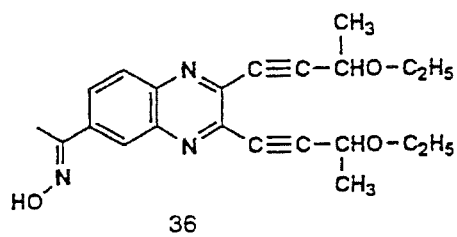
Figure 5:
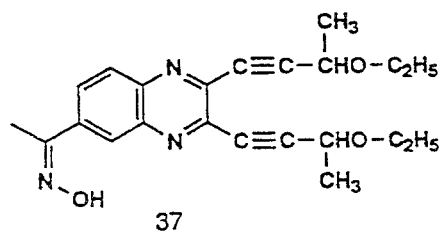
Figure 5:
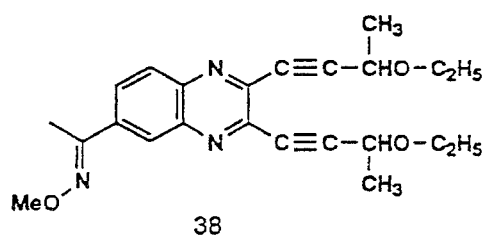
Figure 5:
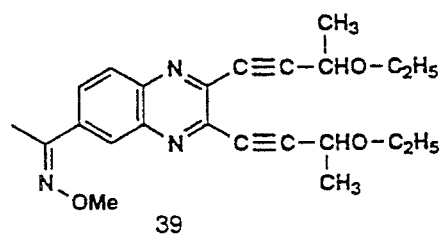
Figure 5:
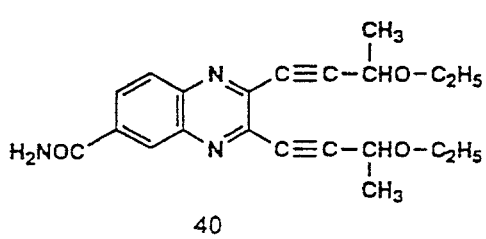
Figure 6:
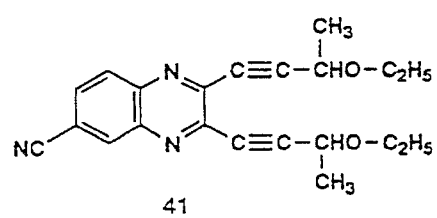
FIG. 6 is a drawing showing structural formulas of compounds 41 to 48 of the present invention
Figure 6:
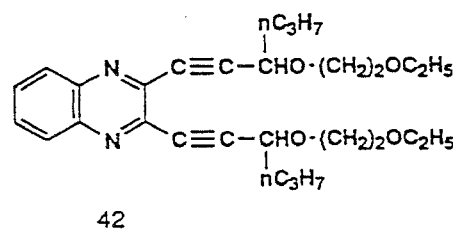
Figure 6:
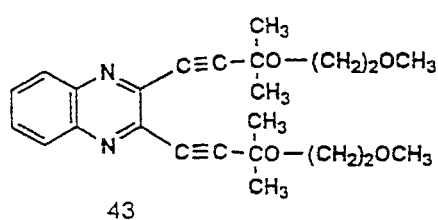
Figure 6:
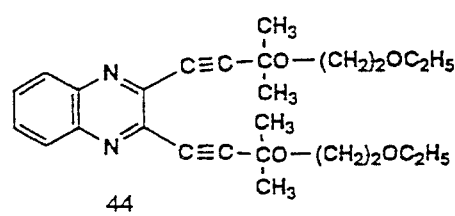
Figure 6:
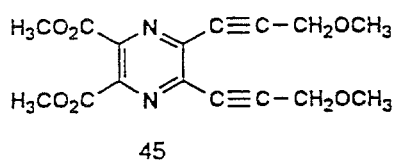
Figure 6:
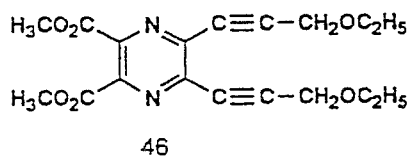
Figure 6:
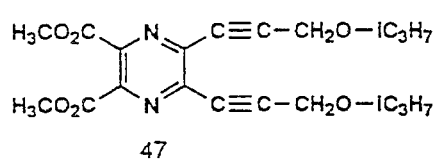
Figure 6:
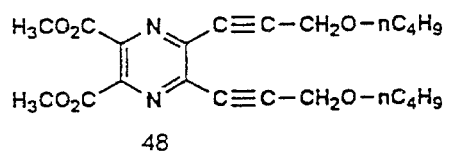
Figure 7:
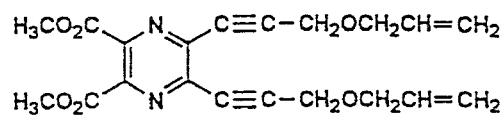
FIG. 7 is a drawing showing structural formulas of compounds 49 to 56 of the present invention
Figure 7:
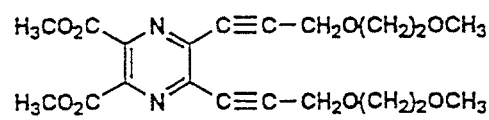
Figure 7:
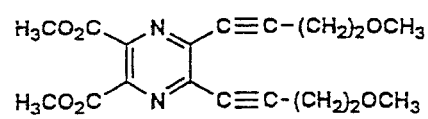
Figure 7:
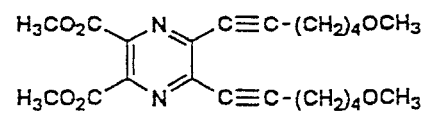
Figure 7:
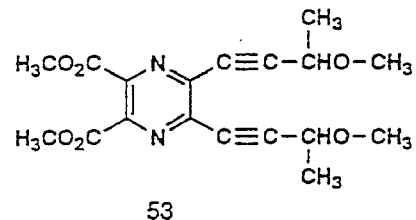
Figure 7:
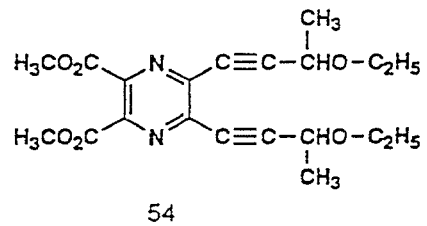
Figure 7:
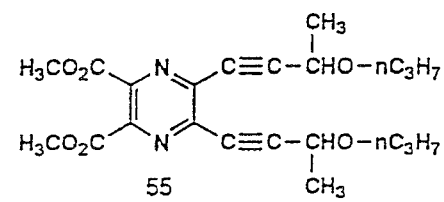
Figure 7:
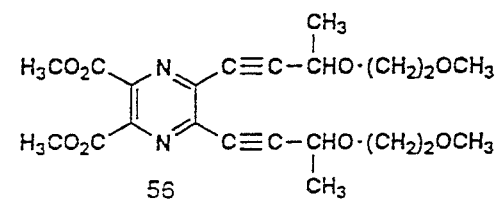
Figure 8:
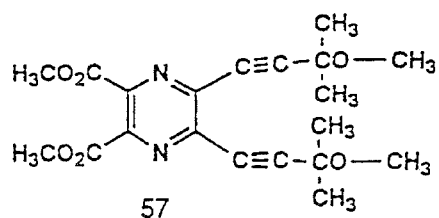
FIG. 8 is a drawing showing structural formulas of compounds 57 to 64 of the present invention
Figure 8:
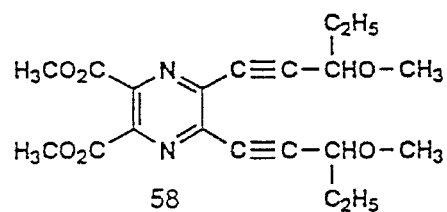
Figure 8:
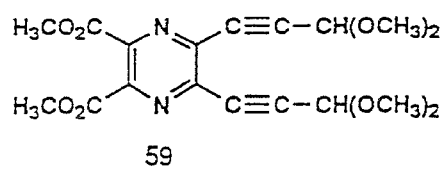
Figure 8:
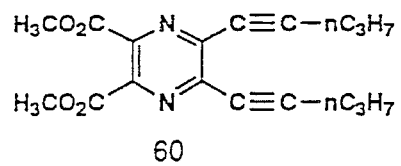
Figure 8:
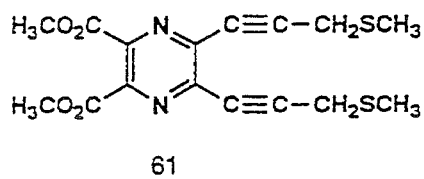
Figure 8:
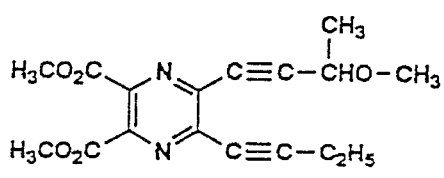
Figure 8:
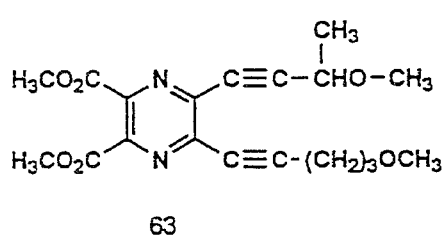
Figure 8:
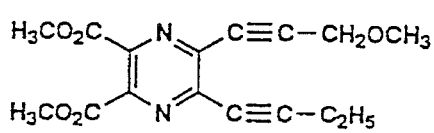
Figure 9:
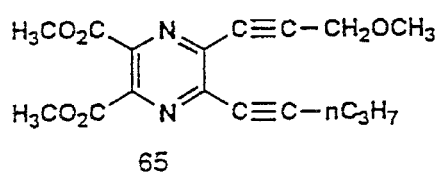
FIG. 9 is a drawing showing structural formulas of compounds 65 to 72 of the present invention
Figure 9:
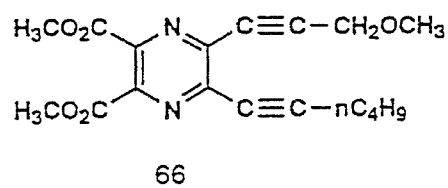
Figure 9:
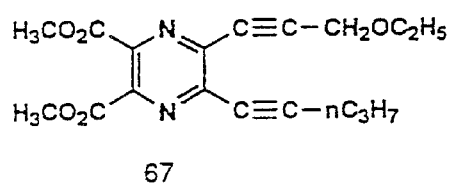
Figure 9:
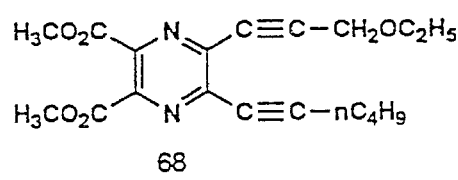
Figure 9:
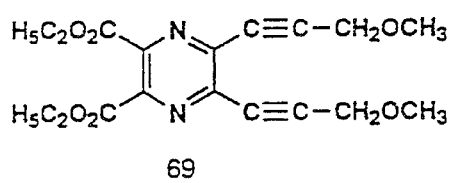
Figure 9:
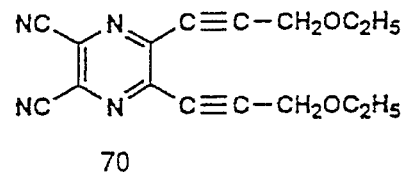
Figure 9:
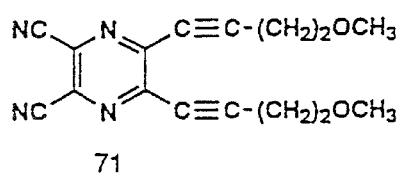
Figure 9:
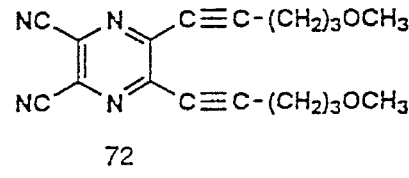
Figure 10:
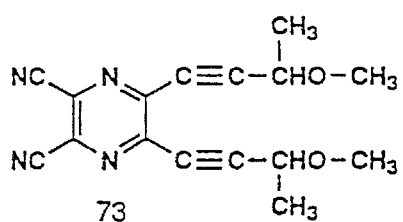
FIG. 10 is a drawing showing structural formulas of compounds 73 to 80 of the present invention
Figure 10:
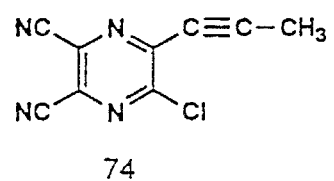
Figure 10:
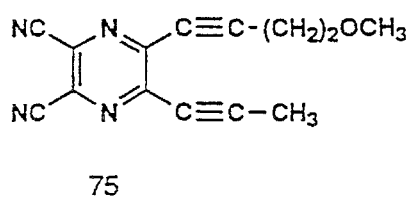
Figure 10:
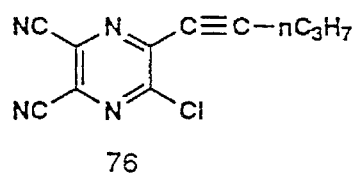
Figure 10:
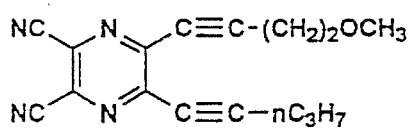
Figure 10:
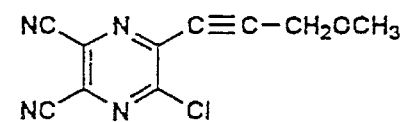
Figure 10:
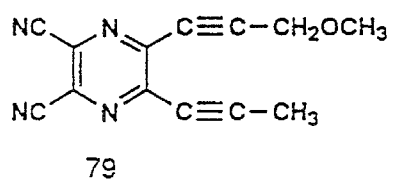
Figure 10:
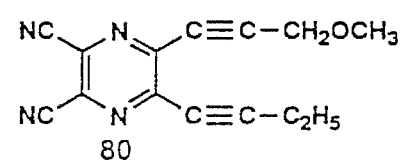
Figure 11:
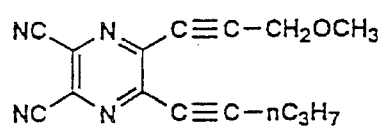
FIG. 11 is a drawing showing structural formulas of compounds 81 to 88 of the present invention
Figure 11:
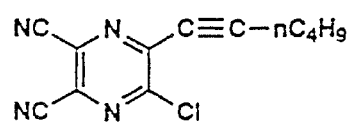
Figure 11:
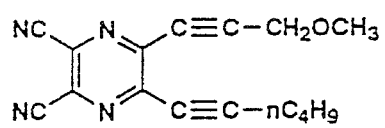
Figure 11:
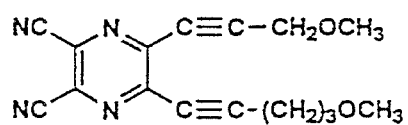
Figure 11:
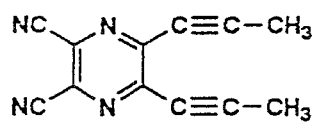
Figure 11:
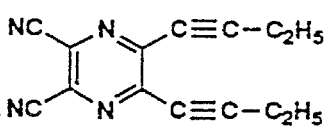
Figure 11:
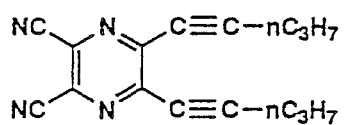
Figure 11:
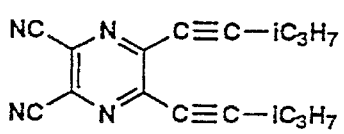
Figure 12:
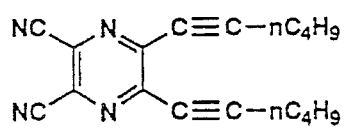
FIG. 12 is a drawing showing structural formulas of compounds 89 to 96 of the present invention
Figure 12:
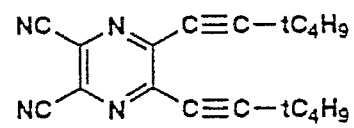
Figure 12:
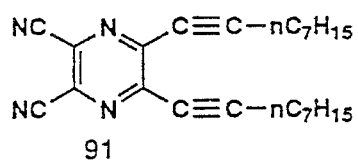
Figure 12:
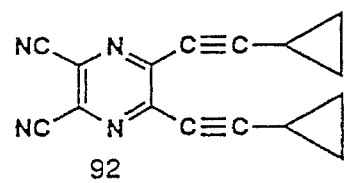
Figure 12:
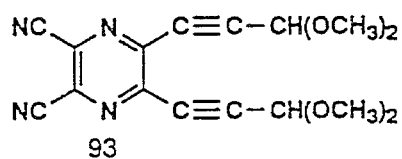
Figure 12:
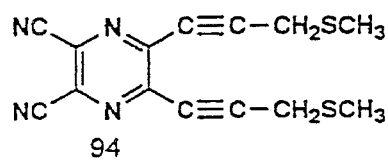
Figure 12:
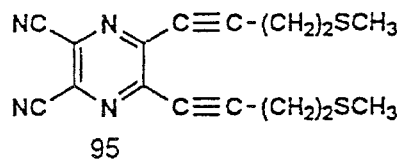
Figure 12:
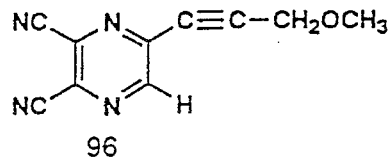
Figure 13:
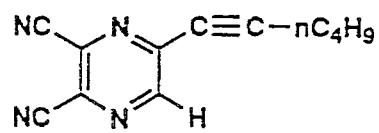
FIG. 13 is a drawing showing structural formulas of compounds 97 to 104 of the present invention.
Figure 13:
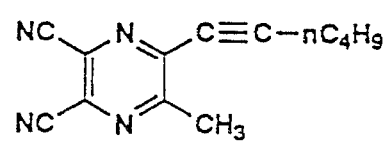
Figure 13:
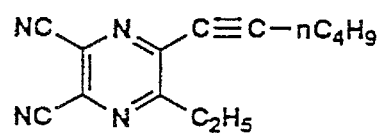
Figure 13:
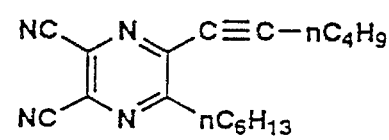
Figure 13:
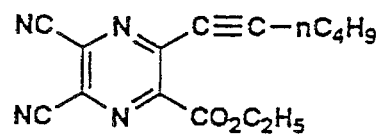
Figure 13:
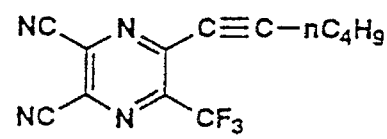
Figure 13:
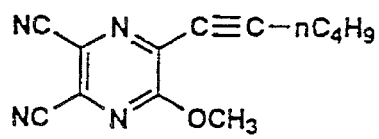
Figure 13:
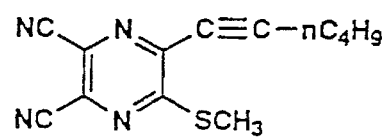
Figure 14:
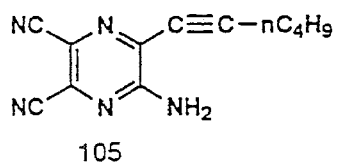
FIG. 14 is a drawing showing structural formulas of compounds 105 to 112 of the present invention.
Figure 14:
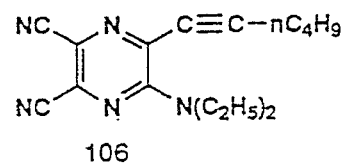
Figure 14:
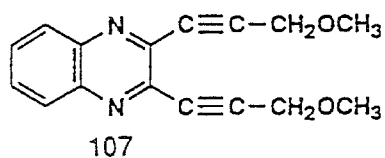
Figure 14:
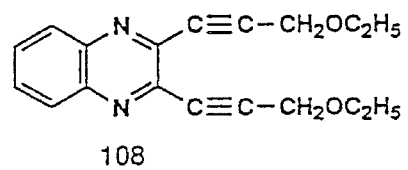
Figure 14:
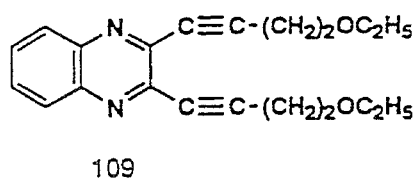
Figure 14:
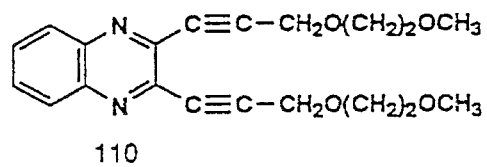
Figure 14:
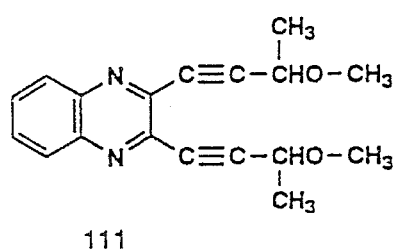
Figure 14:
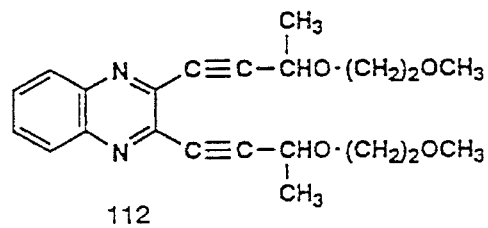
Figure 15:
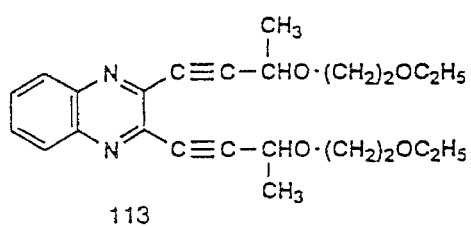
FIG. 15 is a drawing showing structural formulas of compounds 113 to 120 of the present invention.
Figure 15:
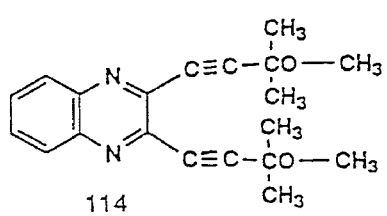
Figure 15:
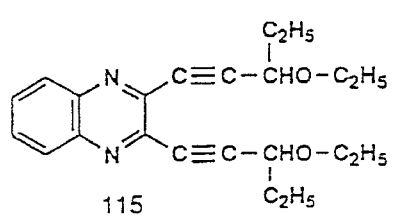
Figure 15:
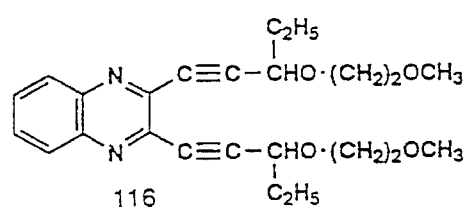
Figure 15:
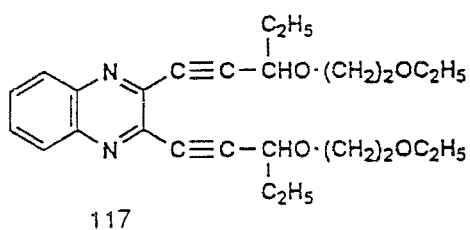
Figure 15:
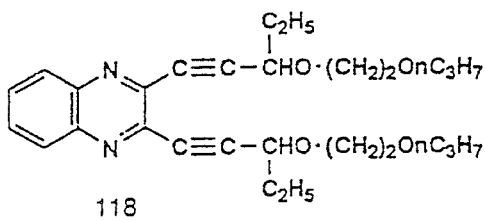
Figure 15:
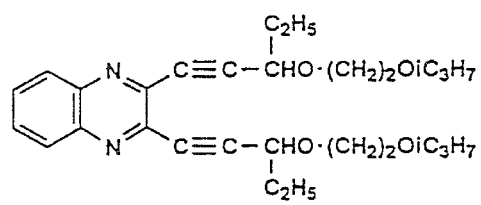
Figure 15:
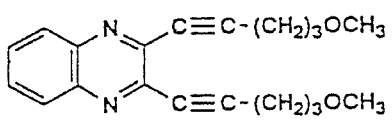
Figure 16:
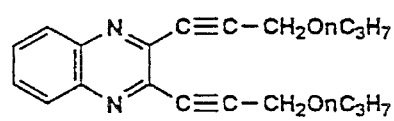
FIG. 16 is a drawing showing structural formulas of compounds 121 to 128 of the present invention.
Figure 16:
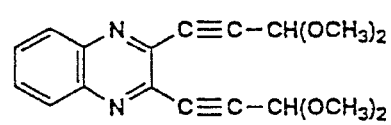
Figure 16:
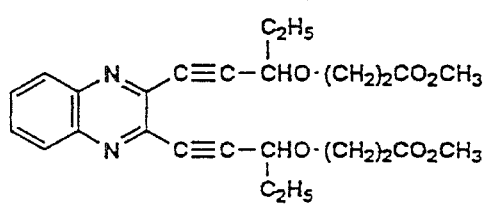
Figure 16:
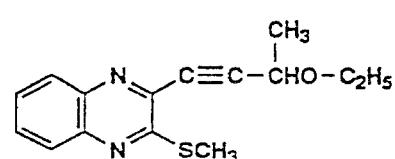
Figure 16:
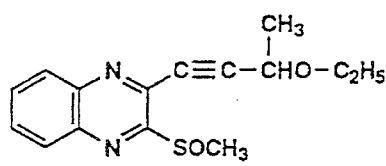
Figure 16:
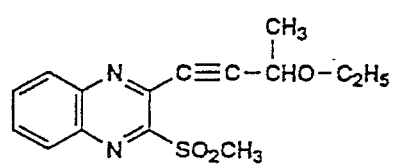
Figure 16:
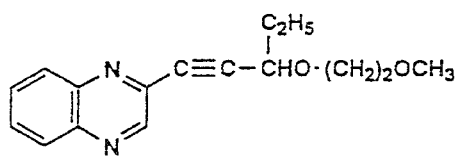
Figure 16:
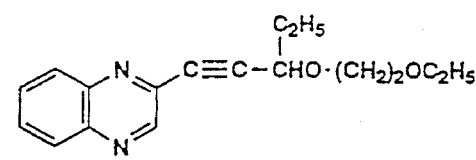
Figure 17:
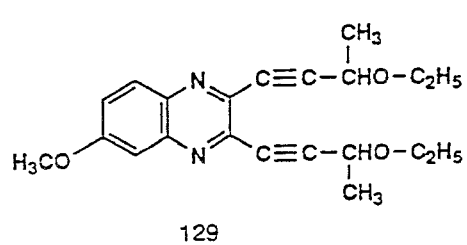
FIG. 17 is a drawing showing structural formulas of compounds 129 to 136 of the present invention.
Figure 17:
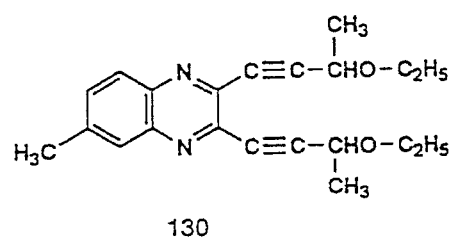
Figure 17:
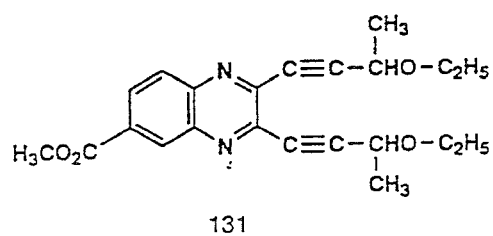
Figure 17:
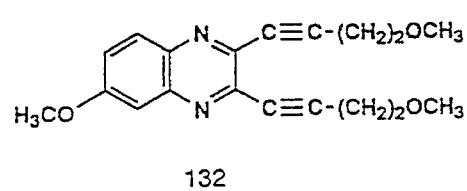
Figure 17:
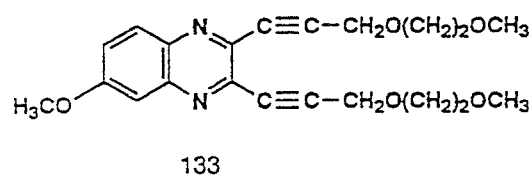
Figure 17:
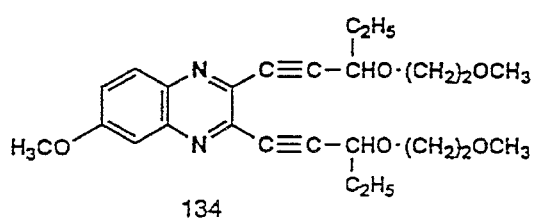
Figure 17:
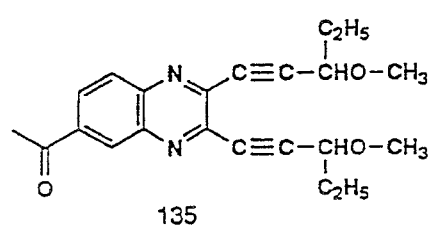
Figure 17:
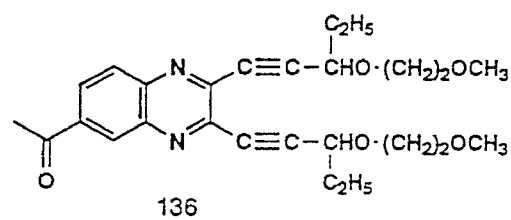
Figure 18:
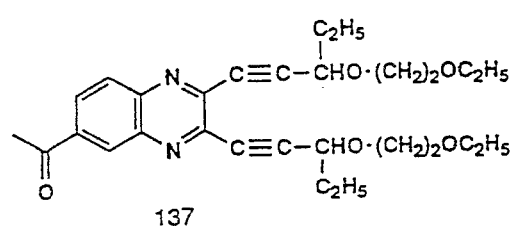
FIG. 18 is a drawing showing structural formulas of compounds 137 to 144 of the present invention.
Figure 18:
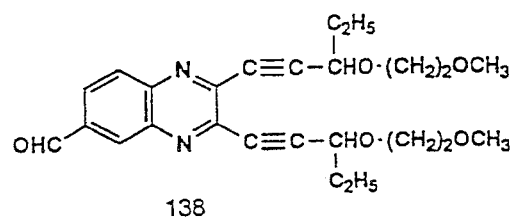
Figure 18:
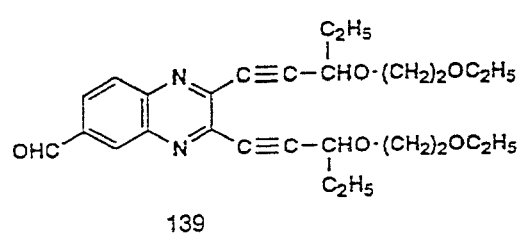
Figure 18:
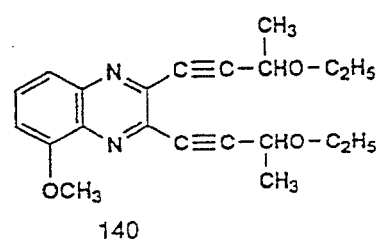
Figure 18:
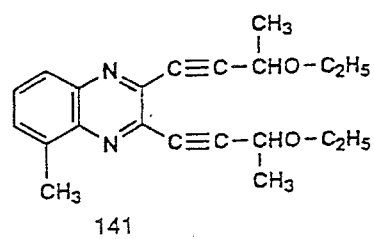
Figure 18:
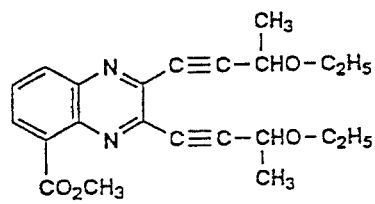
Figure 18:
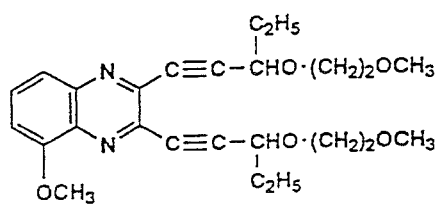
Figure 18:
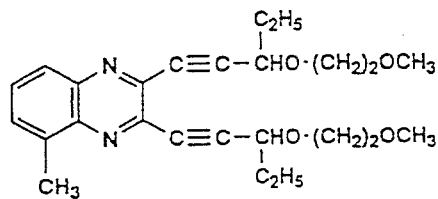
Figure 19:
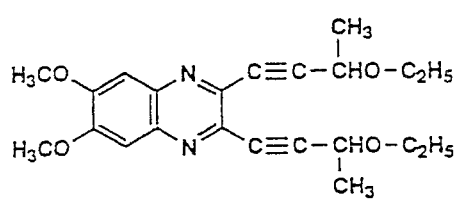
FIG. 19 is a drawing showing structural formulas of compounds 145 to 152 of the present invention.
Figure 19:
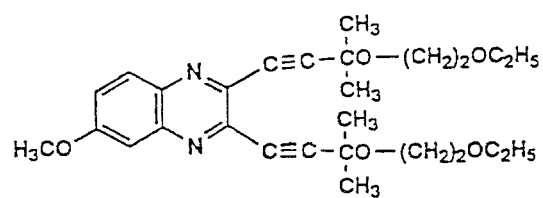
Figure 19:
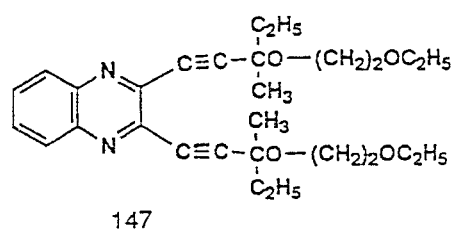
Figure 19:
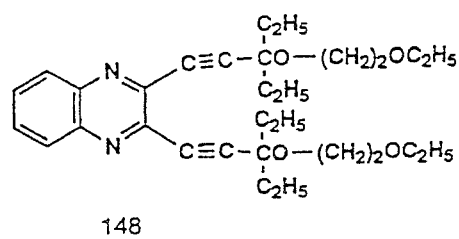
Figure 19:
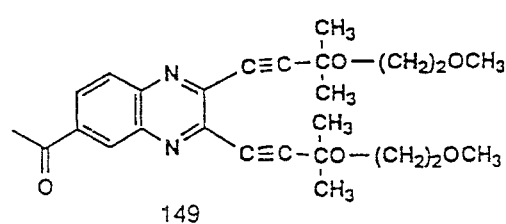
Figure 19:
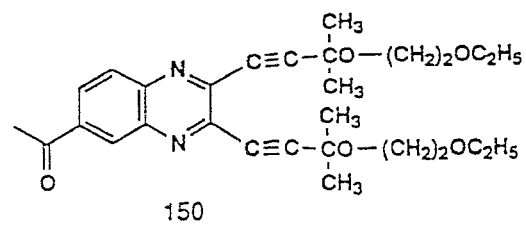
Figure 19:
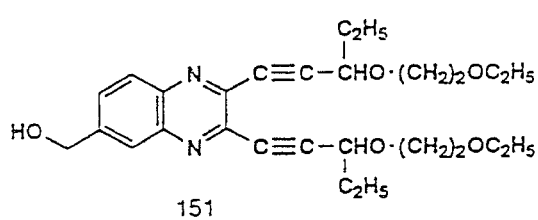
Figure 19:
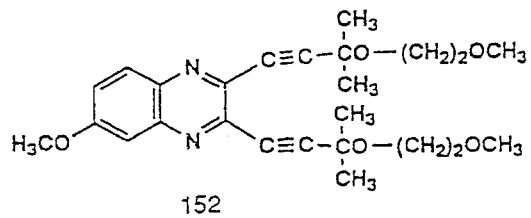
Figure 20:
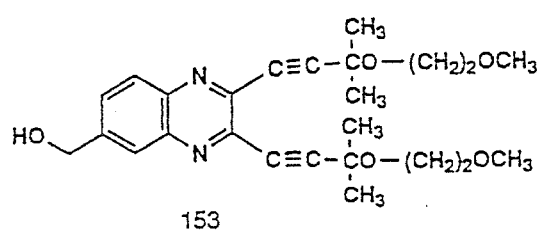
FIG. 20 is a drawing showing structural formulas of compounds 153 to 159 of the present invention.
Figure 20:
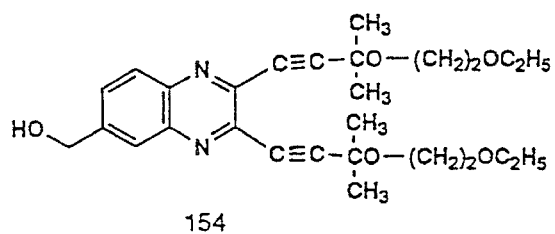
Figure 20:
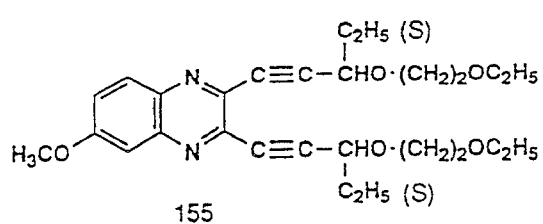
Figure 20:
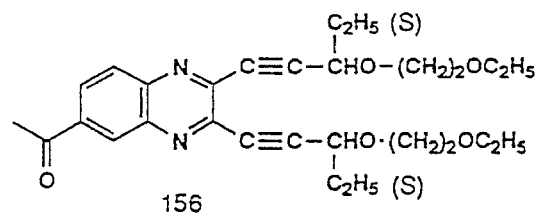
Figure 20:
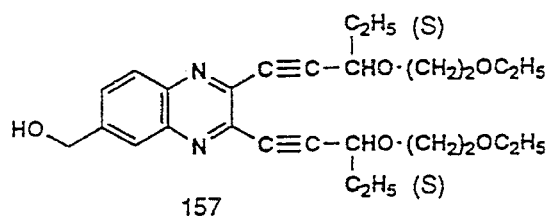
Figure 20:
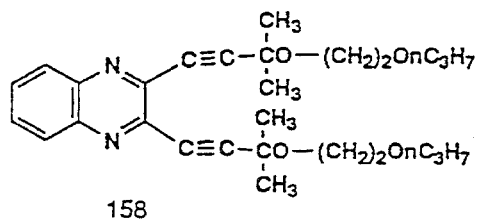
Figure 20:
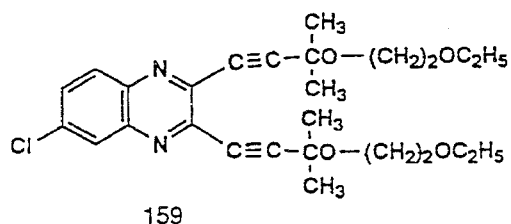

Melting points and IR and NMR spectral data of these compounds are shown in Table 6. Structural formulas of the compounds synthesized in Examples 1 to 157 are shown in FIGS. 1 to 20. The numbers attached to the structural formulas are compound numbers which correspond to respective Examples.

Example 155

Preparation of
6-methoxy-2,3-bis((S)-3-(2-ethoxyethoxy)-
1-pentynyl)quinoxaline

In accordance with the procedure of the step 3 of Example 10, and using 8.71 g of the compound obtained in the step 2 of Example 22 and 1.60 g of 6-methoxy-2,3-dichloroquinoxaline, 2.31 g of the title compound was obtained.

IR (neat, cm$^{-1}$): 2972, 2933, 2872, 2226, 1616, 1487, 1444, 1348, 1227, 1198, 1184, 1119, 1024, 833

NMR (270 MHz, CDCl$_3$, δ, ppm): 7.92 (1H, d), 7.40 (1H, dd), 7.32 (1H, d), 4.40 (2H, t), 4.05–4.00 (2H, m), 3.96 (3H, s), 3.74–3.61 (6H, m), 3.56 (4H, q), 1.99–1.89 (4H, m), 1.22 (6H, t), 1.12 (6H, t)

$[α]^{29}_D$ –93.2° (CHCl$_3$, C=1.04)

Example 156

Preparation of
6-acetyl-2,3-bis((S)-3-(2-ethoxyethoxy)-
1-pentynyl)quinoxaline

In accordance with the procedure of the step 3 of Example 10, and using 8.30 g of the compound obtained in the step 2 of Example 22 and 1.60 g of the compound obtained in the step 2 of Example 33, 1.23 g of the title compound was obtained.

IR (neat, cm$^{-1}$): 2974, 2933, 2872, 2226, 1689, 1400, 1346, 1300, 1180, 1109, 841

NMR (270 MHz, CDCl$_3$, δ, ppm): 8.59 (1H, d), 8.32 (1H, dd), 8.10 (1H, d), 4.43 (2H, t), 4.06–3.99 (2H, m), 3.76–3.64 (6H, m), 3.56 (4H, q), 2.75 (3H, s), 2.00–1.90 (4H, m), 1.22 (6H, t), 1.13 (6H, t)

$[α]^{29}_D$ –90.8° (CHCl$_3$, C=1.07)

Example 157

Preparation of
6-hydroxymethyl-2,3-bis((S)-3-(2-ethoxyethoxy)-
1-pentynyl)quinoxaline In accordance with the procedure of the step 3 of Example 10, and using 19.1 g of the compound obtained in the step 2 of Example 22 and 3.50 g of the compound obtained in the step 1 of Example 31, 2.04 g of the title compound was obtained.

IR (neat, cm$^{-1}$): 3431, 2972, 2931, 2872, 2224, 1622, 1485, 1458, 1346, 1109, 985

NMR (270 MHz, CDCl$_3$, δ, ppm): 8.01 (1H, d), 8.00 (1H, d), 7.76 (1H, dd), 4.94 (2H, d), 4.41 (2H, t), 4.06–3.96 (2H, m), 3.75–3.64 (6H, m), 3.55 (4H, q), 2.08 (1H, t), 2.00–1.89 (4H, m), 1.22 (6H, t), 1.12 (6H, t)

$[α]^{29}_D$ –93.9° (CHCl$_3$, C=1.00)

Example 158

Preparation of
2,3-bis(3-(2-n-propoxyethoxy)-3-methyl-
1-butynyl)quinoxaline (Step1) Preparation of 3-(2-n-propoxyethoxy)-3-methyl-1-butyne In accordance with the procedure of the step 1 of Example 10, 30.3 g of 3-methyl-1-butyne-3-ol was allowed to react with 48.5 g of 2-chloroethylpropyl ether to obtain 13.5 g of 3-(2-n-propoxyethoxy)-3-methyl-1-butyne.

Boiling point (°C.): 90–120 (50 mmHg; colorless oil)

NMR (270 MHz, CDCl$_3$, δ, ppm): 3.72(2H, t), 3.59(2H, t), 3.44(2H, t), 2.41(1H, s), 1.68–1.54(2H, m), 1.48(6H, s), 0.91 (3H, t)

(Step2) Preparation of 2,3-bis(3-(2-n-propoxyethoxy)-3-methyl-1-butynyl)quinoxaline A 3.0 g portion of 2,3-dichloroquinoxaline was suspended in 50 ml of anhydrous acetonitrile. To this were added 7.7 g of the compound obtained in the above step 1, 28 ml of triethylamine, 57.3 mg of copper(I) iodide and 211 mg of bis(triphenylphosphine)palladium(II) chloride and the mixture was stirred at 95° C. for 1.5 hours in an atmosphere of argon. After spontaneous cooling to room temperature, the reaction solution was poured into 150 ml of water and extracted three times with 100 ml of ethyl acetate. The ethyl acetate layers were combined, washed once with 100 ml of water and once with 100 ml of brine, and then dried over anhydrous sodium sulfate. After evaporating the solvent under a reduced pressure, the resulting residue was purified by chromatography on a silica gel column (eluent, hexane/ ethyl acetate) and an alumina column (eluent, hexane/ diethyl ether) to obtain 3.65 g of the title compound.

IR (neat, cm$^{-1}$): 2981, 2960, 2931, 2868, 2226, 1471, 1462, 1336, 1230, 1163, 1128, 1084, 993, 974, 764

NMR (270 MHz, CDCl$_3$, δ, ppm): 8.06–8.03(2H, m), 7.78–7.74(2H, m), 3.88(4H, t), 3.64(4H,t), 3.45(4H, t), 1.67(12H, s), 1.64–1.54(4H, m), 0.90(6H, t)

Example 159

Preparation of
6-chloro-2,3-bis(3-(2-ethoxyethoxy)-3-methyl-
1-butynyl)quinoxaline In accordance with the procedure of the step 2 of Example 158 and using 2.5 g of the compound obtained in the step 1 of Example 44 and 1.5 g of 6-chloro-2,3-dichloroquinoxaline, 1.62 g of the title compound was obtained.

IR (neat, cm$^{-1}$): 2985, 2933, 2872, 2227, 1601, 1468, 1336, 1250, 1227, 1163, 1124, 1086, 833

NMR (270 MHz, CDCl$_3$, δ, ppm): 8.03(1H, d), 7.97(1H, d), 7.69(1H, dd), 3.87(4H, t), 3.64(4H, t), 3.55(4H, q), 1.67(12H, s), 1.21(6H, t)

Example 160

Preparation of 2,3-bis(3-(2-ethoxyethoxy)-3-methyl-1butynyl)quinoxaline (the compound of Example 44)

In an atmosphere of nitrogen, the mixture of 600 mg of the compound obtained in the step 1 of Example 42, 613 mg of the compound obtained in the step 1 of Example 44, 10 mg of copper powder, 540 mg of potassium carbonate, and 5 ml of 1,3-dimethyl-2-imidazolidinone were stirred for 7 hours on an oil bath controlled at 140° C. After spontaneous cooling to room temperature, the reaction solution was mixed with 50 ml of ethyl acetate, and insoluble materials were separated by filtration through celite. The thus separated insoluble materials were washed with 50 ml of ethyl acetate, and the resulting solutions were combined, washed three times with 100 ml of water and once with 100 ml of brine and then dried over anhydrous sodium sulfate. After evaporating the solvent under a reduced pressure, the resulting residue was purified by chromatography on a silica gel column (eluent, hexane/ethyl acetate) to obtain 440 mg of the title compound.

IR: Coincided with that of the compound of Example 44.

NMR: Coincided with that of the compound of Example 44.

Next, examples of pharmaceutical preparations containing the compound of the present invention are provided in the following by way of illustration and not by way of limitation.

Preparation Example 1 (Tablet)

| Component | Amount (g) |
|---|---|
| compound of Example 1 | 100 |
| mannitol | 123 |
| starch | 33 |
| crospovidone | 12 |
| fine crystalline cellulose | 30 |
| magnesium stearate | 2 |

The above components are weighed, mixed uniformly and then subjected to compression tablet making to produce 300 mg of tablets in each weight.

Preparation Example 2 (Hard capsule)

| Component | Amount (g) |
|---|---|
| compound of Example 7 | 40 |
| lactose | 150 |
| starch | 70 |
| polyvinyl pyrrolidone | 5 |
| crystalline cellulose | 35 |

The above components are weighed and uniformly mixed. The thus mixed powder is packed in hard capsules in 300 mg portions to produce a hard capsule preparation.

Preparation Example 3 (Soft capsule)

| Component | Amount (g) |
|---|---|
| compound of Example 117 | 100 |
| tocopherol | 0.2 |

The above components weighed, mixed uniformly and then packed in soft capsules in 100 mg portions to produce a soft capsule preparation.

Preparation Example 4 (Granule)

| Component | Amount (g) |
|---|---|
| compound of Example 11 | 200 |
| lactose | 450 |
| corn starch | 300 |
| hydroxypropyl cellulose | 50 |

The above components are weighed, mixed uniformly and then made into granules in the usual way.

Preparation Example 5 (Syrup)

| Component | Amount (g) |
|---|---|
| compound of Example 12 | 2 |
| saccharin | 0.6 |
| sugar | 30 |
| glycerol | 5 |
| condiment | 0.1 |
| 96% ethanol | 10.4 |
| purified water | balance |
| final volume | 100 ml |

The above components are weighed and sugar and saccharin are dissolved in 60 ml of purified water to which is subsequently added the compound of Example 12 and condiment dissolved in glycerol and ethanol. By adjusting the final volume to 100 ml with purified water, a syrup preparation for use in oral administration can be prepared.

Preparation Example 6 (Powder)

| Component | Amount (g) |
|---|---|
| compound of Example 44 | 100 |
| calcium silicate | 100 |

The above components are weighed, and the compound of Example 44 is adsorbed to calcium silicate and made into fine particles to produce a powder preparation.

TABLE 6

| No.** | IR (cm$^{-1}$) | NMR (CDCl$_3$, δ, ppm) | Melting point (°C.) |
|---|---|---|---|
| 45 | 2988, 2944, 2898, 2827, 2223, 1751, | 4.42 (4H, s), 4.01 (6H, s), 3.49 (6H, s) | 63.4–64.1 |

TABLE 6-continued

| No.** | IR (cm$^{-1}$) | NMR (CDCl$_3$, δ, ppm) | Melting point (°C.) |
|---|---|---|---|
|  | 1721, 1327, 1287, 1196, 1155, 1105, 1097, 1073 | | |
| 46 | 2977, 2870, 2230, 1745, 1732, 1326, 1282, 1200, 1160, 1108, 1069 | 4.46 (4H, s), 4.01 (6H, s), 3.69 (4H, q), 1.27 (6H, t) | 66.5–67.0 |
| 47 | 2975, 2229, 1751, 1734, 1327, 1279, 1214, 1160, 1072 | 4.46 (4H, s), 4.05–3.66 (2H, m), 4.00 (6H, s), 1.23 (12H, d) | oil at ordinary temperature |
| 48 | 2956, 2872, 2240, 1746, 1732, 1327, 1284, 1109, 1072 | 4.45 (4H, s), 4.01 (6H, s), 3.62 (4H, t), 1.80–1.08 (8H, m), 0.94 (6H, t) | 57.2–57.7 |
| 49 | 2970, 2858, 2225, 1745, 1732, 1326, 1284, 1196, 1160, 1071 | 6.15–5.67 (2H, m), 5.46–5.13 (4H, m), 4.47 (4H, s), 4.17 (4H, dt), 4.01 (6H, s) | 46.0–46.7 |
| 50 | 2960, 2924, 2885, 2830, 2228, 1751, 1735, 1328, 1283, 1214, 1198, 1161, 1099, 1076 | 4.54 (4H, s), 4.00 (6H, s), 3.87–3.72 (4H, m), 3.66–3.51 (4H, m), 3.40 (6H, s) | oil at ordinary temperature |
| 51 | 2955, 2893, 2830, 2231, 1756, 1728, 1521, 1338, 1320, 1283, 1214, 1161, 1114, 1080 | 3.99 (6H, s), 3.66 (4H, t), 3.41 (6H, s), 2.82 (4H, t) | oil at ordinary temperature |
| 52 | 2954, 2933, 2868, 2228, 1751, 1729, 1396, 1336, 1278, 1213, 1160, 1119, 1080 | 3.99 (6H, s), 3.49–3.16 (4H, m), 3.34 (6H, s), 2.65–2.35 (4H, m), 1.84–1.59 (8H, m) | oil at ordinary temperature |
| 53 | 2989, 2955, 2939, 2825, 2222, 1752, 1735, 1329, 1279, 1208, 1162, 1115, 1106 | 4.38 (2H, q), 4.01 (6H, s), 3.50 (6H, s), 1.56 (6H, d) | oil at ordinary temperature |
| 54 | 2982, 2870, 2229, 1752, 1735, 1330, 1279, 1213, 1201, 1161, 1112 | 4.46 (2H, q), 4.08–3.69 (2H, m), 4.00 (6H, s), 3.69–3.30 (2H, m), 1.57 (6H, d), 1.25 (6H, t) | oil at ordinary temperature |
| 55 | 2963, 2948, 2880, 2224, 1752, 1735, 1326, 1278, 1213, 1200, 1160, 1112 | 4.44 (2H, q), 4.00 (6H, s), 3.93–3.60 (2H, m), 3.54–3.24 (2H, m), 1.86–1.41 (4H, m), 1.56 (6H, d), 0.94 (6H, t) | oil at ordinary temperature |
| 56 | 2950, 2880, 2228, 1751, 1733, 1330, 1282, 1201, 1162, 1107 | 4.54 (2H, q), 4.11–3.78 (2H, m), 3.78–3.46 (6H, m), 4.00 (6H, s), 3.38 (6H, s), 1.59 (6H, d) | oil at ordinary temperature |
| 57 | 2988, 2954, 2820, 2228, 1752, 1735, 1326, 1277, 1213, 1151, 1074 | 4.00 (6H, s), 3.45 (6H, s), 1.59 (12H, s) | oil at ordinary temperature |
| 58 | 2972, 2941, 2820, 2225, 1756, 1729, 1320, 1282, 1214, 1196, 1160 | 4.19 (2H, t), 4.01 (6H, s), 3.49 (6H, s), 2.07–1.68 (4H, m), 1.08 (6H, t) | oil at ordinary temperature |
| 59 | 2957, 2835, 2260, 1751, 1735, 1341, 1324, 1282, 1214, 1195, 1161, 1110, 1059 | 5.42 (2H, s), 4.00 (6H, s), 3.46 (12H, s) | 45.3–48.6 |
| 60 | 2963, 2940, 2870, 2227, 1744, 1725, 1397, 1338, 1279, 1212, 1161, 1081 | 3.99 (6H, s), 2.52 (4H, t), 1.93–1.39 (4H, m), 1.10 (6H, t) | 54.1–55.4 |
| 61 | 2960, 2910, 2227, 1745, 1730, 1330, 1283, 1203, 1157, 1072 | 4.01 (6H, s), 3.56 (4H, s), 2.34 (6H, s) | 77.6–78.8 |
| 62 | — | $^{13}$C-NMR (60 MHz) 13.0, 13.6, 21.6, 53.4, 56.7, 67.4 79.2, 81.3, 98.8, 103.5, 141.4, 141.7, 142.1, 164.1 | oil at ordinary temperature |
| 63 | 2955, 2890, 2228, 1751, 1732, 1332, | 4.38 (1H, q), 4.00 (6H, s), 3.52 (2H, t), 3.51 (3H, s), | oil at ordinary |

TABLE 6-continued

| No.** | IR (cm$^{-1}$) | NMR (CDCl$_3$, δ, ppm) | Melting point (°C.) |
|---|---|---|---|
|  | 1279, 1211, 1161, 1117, 1077 | 3.35 (3H, s), 2.64 (2H, t), 2.07–1.74 (2H, m), 1.57 (3H, d) | temperature |
| 64 | — | $^{13}$C-NMR (60 MHz) 12.9, 13.5, 53.4, 57.9, 60.1, 76.6, 82.3, 94.9, 103.6, 141.3, 142.2, 142.5, 164.0 | oil at ordinary temperature |
| 65 | — | $^{13}$C-NMR (60 MHz) 13.4, 21.3, 21.7, 53.2, 57.8, 60.0, 74.8, 82.2, 94.7, 102.5, 140.9, 141.5, 141.7, 163.9 | oil at ordinary temperature |
| 66 | — | $^{13}$C-NMR (60 MH,) 13.5, 19.5, 21.9, 29.9, 53.4, 57.9, 60.1, 77.2, 82.3, 94.8, 102.7, 141.0, 142.5, 164.0 | oil at ordinary temperature |
| 67 | — | $^{13}$C-NMR (60 MHz) 12.5, 14.0, 20.5, 20.8, 52.3, 57.3, 64.9, 76.5, 80.9, 94.3, 101.5, 140.1, 140.3, 141.2, 141.5, 163.0, 163.1 | oil at ordinary temperature |
| 68 | — | $^{13}$C-NMR (60 MHz) 13.5, 13.9, 15.1, 19.6, 22.1, 30.0, 53.4, 58.3, 66.0, 77.3, 81.9, 95.3, 102.7, 142.3, 142.6, 164.1 | oil at ordinary temperature |
| 69 | 2987, 2935, 2826, 2229, 1751, 1735, 1321, 1272, 1195, 1160, 1101, 1072 | 4.47 (4H, q), 4.42 (4H, s), 3.49 (6H, s), 1.41 (6H, t) | oil at ordinary temperature |
| 70 | 2989, 2881, 2240, 2228, 1508, 1407, 1391, 1376, 1351, 1201, 1178, 1103, 1075 | 4.49 (4H, s), 3.70 (4H, q), 1.28 (6H, t) | 44.1–44.7 |
| 71 | 2900, 2226, 1506, 1386, 1186, 1123, 1109, 995 | 3.67 (4H, t), 3.42 (6H, s), 2.87 (4H, t) | 49.0–49.4 |
| 72 | 2930, 2890, 2223, 1506, 1382, 1189, 1114 | 3.53 (4H, t), 3.36 (6H, s), 2.71 (4H, t), 2.08–1.76 (4H, m) | 34.6–35.5 |
| 73 | 2943, 2931, 2825, 2227, 1508, 1375, 1206, 1188, 1106 | 4.41 (2H, q), 3.50 (6H, s), 1.59 (6H, d) | 82.9–83.6 |
| 74 | 2232, 1515, 1496, 1407, 1334, 1194, 1148, 1085, 929 | 2.31 (3H, s) | 105.5–108.2 |
| 75 | 2900, 2227, 1505, 1411, 1389, 1370, 1208, 1187, 1107, 990 | 3.66 (2H, t), 3.42 (3H, s), 2.87 (2H, t), 2.27 (3H, s) | 80.2–81.0 |
| 76 | — | 2.62 (2H, t), 1.93–1.50 (2H, m), 1.11 (3H, t) | — |
| 77 | 2960, 2930, 2225, 1506, 1385, 1200, 1180, 1115 | 3.66 (2H, t), 3.41 (3H, s), 2.86 (2H, t), 2.59 (2H, t), 1.93–1.52 (2H, m), 1.11 (3H, t) | oil at ordinary temperature |
| 78 | 2226, 1522, 1400, 1356, 1331, 1188, 1147, 1095, 1068, 897 | 4.48 (2H, s), 3.51 (3H, s) | 95.1–97.3 |
| 79 | 2950, 2238, 2226, 1509, 1382, 1206, 1189, 1099 | 4.47 (2H, s), 3.51 (3H, s), 2.27 (3H, s) | 78.6–79.3 |
| 80 | 2950, 2240, 2223, 1505, 1389, 1203, 1184, 1099 | 4.46 (2H, s), 3.50 (3H, s), 2.62 (2H, q), 1.33 (3H, t) | 85.9–86.4 |
| 81 | 2970, 2936, 2227, 1386, 1188, 1098 | 4.45 (2H, s), 3.50 (3H, s), 2.59 (2H, t), 1.93–1.52 (2H, m), 1.10 (3H, t) | 53.7–55.1 |
| 82 | 2961, 2936, 2874, 2228, 1519, 1497, 1407, 1333, 1190, 1145, 1083 | 2.64 (2H, t), 1.89–1.24 (4H, m), 0.98 (3H, t) | oil at ordinary temperature |
| 83 | 2961, 2941, 2874, 2222, 1505, 1386, 1200, 1184, 1096 | 4.47 (2H, s), 3.50 (3H, s), 2.61 (2H, t), 1.86–1.22 (4H, m), 0.97 (3H, t) | 40.4–40.9 |
| 84 | 2950, 2890, 2920, 2225, 1508, 1382, | 4.46 (2H, s), 3.52 (2H, t), 3.50 (3H, s), 3.36 (3H, s), | 38.3–38.7 |

TABLE 6-continued

| No.** | IR (cm$^{-1}$) | NMR (CDCl$_3$, δ, ppm) | Melting point (°C.) |
|---|---|---|---|
|  | 1354, 1205, 1189, 1122, 1099 | 2.71 (2H, t), 2.14–1.78 (2H, m) |  |
| 85 | 2930, 2239, 2228, 1506, 1500, 1386, 1371, 1210, 1190 | 2.27 (6H, s) | 186.8–187.7 |
| 86 | 2989, 2943, 2239, 2219, 1505, 1385, 1376, 1210, 1200 | 2.62 (4H, q), 1.34 (6H, t) | 114.9–116.0 |
| 87 | 2968, 2935, 2876, 2222, 1498, 1383 | 2.57 (4H, t), 1.93–1.50 (4H, m), 1.10 (6H, t) | 60.2–60.5 |
| 88 | 2974, 2936, 2232, 2219, 1506, 1380, 1198 | 3.24–2.68 (2H, m), 1.36 (12H, d) | 109.5–109.9 |
| 89 | 2961, 2936, 2874, 2222, 1507, 1501, 1459, 1387, 1383, 1204, 1188 | 2.60 (4H, t), 1.89–1.33 (8H, m), 0.98 (6H, t) | oil at ordinary temperature |
| 90 | 2972, 2226, 2213, 1497, 1459, 1405, 1379, 1387, 1365, 1261, 1191 | 1.41 (18H, s) | 168.6–171.1 |
| 91 | 2955, 2934, 2857, 2223, 1502, 1466, 1459, 1407, 1387, 1384, 1204, 1188 | 2.56 (4H, t), 1.86–1.09 (20H, m), 0.90 (6H, m) | oil at ordinary temperature |
| 92 | 3020, 2208, 1502, 1403, 1333, 1199, 1180, 1030, 967, 922 | 1.80–1.44 (2H, m), 1.20–0.90 (8H, m) | 138.8–139.4 |
| 93 | 2966, 2940, 2837, 2235, 1514, 1407, 1379, 1351, 1338, 1198, 1183, 1126, 1114, 1102, 1058, 969, 963 | 5.45 (2H, s), 3.47 (12H, s) | 81.9–82.6 |
| 94 | 2919, 2224, 1506, 1406, 1382, 1315, 1230, 1187 | 3.59 (4H, s), 2.33 (6H, s) | — |
| 95 | 2227, 1502, 1386 | 2.94–2.76 (8H, m), 2.21 (6H, s) | — |
| 96 | — | $^{13}$C-NMR (60 MHz) 58.3, 59.9, 81.0, 97.8, 112.2, 112.6, 130.8, 133.1, 141.8, 149.5 | 70–71 |
| 97 | — | $^{13}$C-NMR (60 MHz) 13.4, 19.5, 21.9, 29.6, 105.4, 112.3, 112.7, 129.9, 133.0, 143.0, 150.0 | oil at ordinary temperature |
| 98 | — | $^{13}$C-NMR (60 MHz) 13.4, 22.8, 19.5, 22.1, 29.9, 106.9, 112.6, 113.0, 128.9, 130.2, 142.7, 160.2 | oil at ordinary temperature |
| 99 | — | $^{13}$C-NMR (60 MHz) 10.8, 13.1, 19.3, 21.8, 28.8, 29.6, 76.4, 106.3, 112.5, 112.8, 128.9, 129.9, 142.2, 164.3 | oil at ordinary temperature |
| 100 | — | $^{13}$C-NMR (60 MHz) 13.2, 13.6, 19.3, 21.8, 22.2, 27.3, 28.7, 29.6, 31.2, 35.4, 76.6, 105.8, 112.5, 112.8, 129.1, 130.0, 142.2, 163.5 | oil at ordinary temperature |
| 101 | — | $^{13}$C-NMR (60 MHz) 13.2, 13.9, 19.6, 21.8, 29.5, 63.4, 76.4, 109.1, 111.9, 112.2, 128.6, 133.5, 140.5, 148.4, 161.3 | oil at ordinary temperature |
| 102 | — | $^{13}$C-NMR (60 MHz) 13.2, 19.7, 21.8, 29.3, 111.8, 121.6, 127.8, 134.7, 140.5, 148.4 | oil at ordinary temperature |
| 103 | — | $^{13}$C-NMR (60 MHz) 13.1, 19.3, 21.5, 29.5, 56.0, 74.5, 106.5, 112.6, 124.4, 127.4, 134.5, 160.2 | oil at ordinary temperature |
| 104 | — | $^{13}$C-NMR (60 MHz) 13.4, 13.8, 19.6, 21.9, 29.6, 75.8, 109.6, 113.0, 126.3, 129.1, 140.4, 165.4 | 63–65 |
| 105 | — | $^{13}$C-NMR (60 MHz) 13.4, 19.5, 22.1, 29.9, 74.5, | 100–101 |

TABLE 6-continued

| No.** | IR (cm$^{-1}$) | NMR (CDCl$_3$, δ, ppm) | Melting point (°C.) |
|---|---|---|---|
| 106 | — | 105.4, 113.4, 113.6, 121.0, 129.7, 154.7<br>$^{13}$C-NMR (60 MHz)<br>12.7, 13.0, 19.1, 21.7, 29.3,<br>44.4, 77.9, 100.8, 113.1, 113.6,<br>117.3, 126.6, 128.4, 151.9 | oil at ordinary temperature |
| 107 | 2990, 2950, 2830, 2224, 1364, 1339, 1210, 1190, 1131, 1096, 901, 765 | 8.13–7.92 (2H, m),<br>7.86–7.65 (2H, m),<br>4.47 (4H, s), 3.54 (6H, s) | 88.8–89.3 |
| 108 | 2974, 2860, 2231, 1349, 1336, 1096, 769 | 8.13–7.89 (2H, m), 7.89–7.63 (2H, m), 4.50 (4H, s), 3.74 (4H, q), 1.29 (6H, t) | 60.2–61.1 |
| 109 | 2978, 2874, 2229, 1341, 1138, 1115, 1108, 761 | 8.07–7.83 (2H, m) 7.77–7.53 (2H, m), 3.75 (4H, t),<br>3.59 (4H, q), 2.86 (4H, t),<br>1.24 (6H, t) | 70.0–70.5 |
| 110 | 2887, 2882, 2225, 1358, 1336, 1133, 1096, 1089, 763 | 8.10–7.86 (2H, m), 7.86–7.62 (2H, m), 4.58 (4H, s), 3.90–3.75 (4H, m), 3.66–3.51 (4H, m),<br>3.42 (6H, s) | 25.3–25.9 |
| 111 | 2989, 2934, 2822, 2221, 1338, 1200, 1133, 1115, 1068, 760 | 8.15–7.91 (2H, m), 7.83–7.64 (2H, m), 4.43 (2H, q),<br>3.55 (6H, s), 1.61 (6H, d) | 60.2–61.5 |
| 112 | 2986, 2934, 2874, 2223, 1339, 1193, 1132, 1106, 1077, 766 | 8.13–7.92 (2H, m), 7.88–7.64 (2H, m), 4.59 (2H, q), 4.18–3.84 (2H, m), 3.84–3.47 (6H, m),<br>3.40 (6H, s), 1.65 (6H, d) | oil at ordinary temperature |
| 113 | 2979, 2868, 2223, 1475, 1394, 1372, 1339, 1212, 1193, 1107, 1077, 765 | 8.13–7.92 (2H, m), 7.86–7.65 (2H, m), 4.61 (2H, q), 4.14–3.84 (2H, m), 3.84–3.54 (6H, m),<br>3.56 (4H, q), 1.64 (6H, d),<br>1.22 (6H, t) | oil at ordinary temperature |
| 114 | 2983, 2932, 2820, 2233, 1336, 1174, 1074, 769 | 8.13–7.95 (2H, m), 7.86–7.68 (2H, m), 3.51 (6H, s),<br>1.65 (12H, s) | 97.0–97.8 |
| 115 | 2972, 2935, 2876, 2224, 1339, 1190, 1128, 1111, 1087, 1079, 765 | 8.10–7.89 (2H, m), 7.83–7.62 (2H, m), 4.32 (2H, t), 4.14–3.75 (2H, m), 3.75–3.36 (2H, m),<br>2.07–1.62 (4H, m), 1.27 (6H, t),<br>1.13 (6H, t) | 32.9–33.7 |
| 116 | 2971, 2932, 2878, 2226, 1338, 1132, 1108, 1090, 765 | 8.10–7.92 (2H, m),7.83–7.65 (2H, m), 4.40 (2H, t), 4.14–3.84 (2H, m), 3.84–3.48 (6H, m),<br>3.40 (6H, s), 2.10–1.74 (4H, m),<br>1.13 (6H, t) | oil at ordinary temperature |
| 117 | 2973, 2934, 2871, 2226, 1338, 1130, 765 | 8.10–7.89 (2H, m), 7.80–7.59 (2H, m), 4.41 (2H, t), 4.17–3.84 (2H, m), 3.81–3.48 (6H, m),<br>3.56 (4H, q), 2.10–1.74 (4H, m),<br>1.22 (6H, t), 1.12 (6H, t) | oil at ordinary temperature |
| 118 | 2966, 2935, 2873, 2226, 1338, 1130, 1109, 764 | 8.14–7.97 (2H, m), 7.89–7.67 (2H, m), 4.41 (2H, t), 4.15–3.88 (2H, m), 3.86–3.56 (6H, m),<br>3.45 (4H, t), 2.14–1.78 (4H, m),<br>1.74–1.37 (4H, m), 1.12 (6H, t),<br>0.92 (6H, t) | oil at ordinary temperature |
| 119 | 2972, 2933, 2872, 2226, 1367, 1336, 1190, 1153, 1190, 1153, 1130, 1113, 1088, 766 | 8.14–7.93 (2H, m), 7.86–7.63 (2H, m), 4.42 (2H, t), 4.09–3.84 (2H, m), 3.39–3.45 (8H, m),<br>2.10–1.71 (4H, m),<br>1.17 (12H, d), 1.14 (6H, t) | oil at ordinary temperature |
| 120 | 2927, 2874, 2229, 1396, 1344, 1118, 764 | 8.07–7.89 (2H, m), 7.80–7.62 (2H, m), 3.58 (4H, t),<br>3.38 (6H, s), 2.68 (4H, t),<br>2.13–1.77 (4H, m) | oil at ordinary temperature |
| 121 | 2967, 2869, 2231, 1357, 1336, 1216, 1194, 1095, 782 | 8.16–7.89 (2H, m), 7.89–7.61 (2H, m), 4.50 (4H, s),<br>3.63 (4H, t), 1.90–1.41 (4H, m),<br>0.98 (6H, t) | 55.3–56.5 |
| 122 | 2970, 2941, 2908, 2830, 2237, 1366, 1342, 1186, 1138, 1111, 1046, 953, 764 | 8.13–7.95 (2H, m), 7.89–7.71 (2H, m), 5.48 (2H, s),<br>3.50 (12H, s) | 81.7–82.5 |

TABLE 6-continued

| No.** | IR (cm$^{-1}$) | NMR (CDCl$_3$, δ, ppm) | Melting point (°C.) |
|---|---|---|---|
| 123 | 2972, 2953, 2939, 2879, 2226, 1743, 1736, 1437, 1339, 1194, 1106, 1070, 766 | 8.14–7.95 (2H, m), 7.86–7.65 (2H, m), 4.35 (2H, t), 4.22–4.01 (2H, m), 3.96–3.75 (2H, m), 3.70 (6H, s), 2.65 (4H, t), 2.08–1.71 (4H, m), 1.09 (6H, t) | oil at ordinary temperature |
| 124 | 2980, 2929, 2222, 1328, 1280, 1215, 1110, 1088, 1078, 768 | 8.06–7.82 (2H, m), 7.82–7.46 (2H, m), 4.53 (1H, q), 4.22–3.80 (1H, m), 3.80–3.38 (1H, m), 2.67 (3H, s), 1.63 (3H, d), 1.29 (3H, t) | 49.6–50.2 |
| 125 | 2980, 2934, 2870, 2224, 1330, 1110, 1089, 1055, 767 | 8.40–8.01 (2H, m), 8.01–7.71 (2H, m), 4.52 (1H, q), 4.11–3.75 (1H, m), 3.75–3.39 (1H, m), 3.04 (3H, s), 1.63 (3H, d), 1.30 (3H, dt) | oil at ordinary temperature |
| 126 | 2986, 2937, 2869, 2228, 1344, 1316, 1149, 1107, 948, 770, 761, 513 | 8.25–8.04 (2H, m), 8.04–7.80 (2H, m), 4.57 (1H, q), 4.14–3.81 (1H, m), 3.81–3.48 (1H, m), 3.51 (3H, s), 1.64 (3H, d), 1.28 (3H, t) | 113.8–114.5 |
| 127 | 2970, 2931, 2875, 2227, 1541, 1294, 1203, 1128, 1107, 1090, 766 | 8.88 (1H, s), 8.19–7.92 (2H, m), 7.89–7.62 (2H, m), 4.38 (1H, t), 4.04–3.79 (1H, m), 3.79–3.54 (3H, m), 3.42 (3H, s), 2.13–1.74 (2H, m), 1.12 (3H, t) | oil at ordinary temperature |
| 128 | 2972, 2872, 2227, 1541, 1487, 1338, 1126, 1107, 766 | 8.88 (1H, s), 8.19–7.95 (2H, m), 7.92–7.68 (2H, m), 4.39 (1H, t), 4.14–3.81 (1H, m), 3.81–3.48 (3H, m), 3.57 (2H, q), 2.13–1.74 (2H, m), 1.23 (3H, t), 1.12 (3H, t) | oil at ordinary temperature |
| 129 | 2981, 2935, 2896, 2871, 2225, 1617, 1487, 1444, 1347, 1227, 1198, 1111, 833 | 7.92 (1H, d), 7.50–7.26 (2H, m), 4.50 (2H, q), 4.14–3.75 (2H, m), 3.95 (3H, s), 3.75–3.36 (2H, m), 1.61 (6H, d), 1.27 (6H, t) | oil at ordinary temperature |
| 130 | 2980, 2933, 2895, 2870, 2224, 1620, 1487, 1444, 1398, 1369, 1340, 1198, 1157, 1132, 1111, 1072, 827 | 7.92 (1H, d), 7.80 (1H, d), 7.56 (1H, dd), 4.50 (2H, q), 4.16–3.79 (2H, m), 3.73–3.36 (2H, m), 2.58 (3H, s), 1.61 (6H, d), 1.27 (6H, t) | oil at ordinary temperature |
| 131 | 2981, 2937, 2896, 2873, 2219, 1715, 1343, 1268, 1258, 1197, 1189, 1108, 1094, 765 | 8.74 (1H, d), 8.35 (1H, dd), 8.07 (1H, d), 4.52 (2H, q), 4.14–3.75 (2H, m), 4.01 (3H, s), 3.75–3.36 (2H, m), 1.63 (6H, d), 1.28 (6H, t) | 91.4–92.1 |
| 132 | 2885, 2862, 2233, 1617, 1490, 1353, 1229, 1116, 1104, 1014 | 7.88 (1H, d), 7.35 (1H, dd), 7.28 (1H, d), 3.94 (3H, s), 3.70 (4H, t), 3.43 (6H, s), 2.85 (4H, t) | 68.2–68.7 |
| 133 | 2920, 2892, 2226, 1616, 1487, 1345, 1227, 1196, 1095, 1015 | 7.92 (1H, d), 7.50–7.26 (2H, m), 4.57 (2H, s), 4.56 (2H, s), 3.96 (3H, s), 3.96–3.78 (4H, m), 3.72–3.54 (4H, m), 3.42 (6H, s) | 78.5–79.1 |
| 134 | 2970, 2935, 2877, 2226, 1616, 1487, 1446, 1348, 1227, 1120, 1109, 1090, 1024 | 7.91 (1H, d), 7.78–7.26 (2H, m), 4.38 (2H, t), 4.16–3.90 (2H, m), 3.96 (3H, s), 3.86–3.54 (6H, m), 3.40 (6H, s), 2.21–1.74 (4H, m), 1.12 (6H, t) | oil at ordinary temperature |
| 135 | 2972, 2937, 2879, 2825, 2226, 1689, 1344, 1182, 1126, 1105, 1083, 841 | 8.59 (1H, d), 8.33 (1H, dd), 8.08 (1H, d), 4.25 (2H, t), 3.54 (6H, s), 2.75 (3H, s), 2.10–1.74 (4H, m), 1.13 (6H, t) | oil at ordinary temperature |
| 136 | 2972, 2931, 2877, 2224, 1689, 1460, 1400, 1344, 1302, 1240, 1182, 1126, 1109, 1090, 841 | 8.59 (1H, d), 8.33 (1H, dd), 8.08 (1H, d), 4.41 (2H, t), 4.16–3.88 (2H, m), 3.84–3.51 (6H, m), 3.41 (6H, s), 2.35 (3H, s), 2.14–1.76 (4H, m), 1.13 (6H, t) | oil at ordinary temperature |
| 137 | 2974, 2933, 2872, 2226, 1689, 1346, 1180, 1109 | 8.59 (1H, d), 8.32 (1H, dd), 8.08 (1H, d), 4.42 (2H, t), 4.14–3.84 (2H, m), 3.84–3.54 (6H, m), 3.56 (4H, q), 2.75 (3H, s), 2.13–1.74 (4H, m), 1.22 (6H, t), 1.13 (6H, t) | oil at ordinary temperature |

TABLE 6-continued

| No.** | IR (cm$^{-1}$) | NMR (CDCl$_3$, δ, ppm) | Melting point (°C.) |
|---|---|---|---|
| 138 | 2974, 2927, 2877, 2821, 2222, 1699, 1338, 1192, 1142, 1113, 1086, 1032, 835 | 10.23 (1H, s), 8.99 (1H, d), 8.24 (1H, dd), 8.14 (1H, d), 4.42 (2H, t), 4.20–3.90 (2H, m), 3.84–3.51 (6H, m), 3.41 (6H, s), 2.16–1.74 (4H, m), 1.13 (6H, t) | 42.4–46.7 |
| 139 | 2974, 2933, 2872, 2226, 1701, 1381, 1336, 1330, 1190, 1142, 1109, 839, 793 | *10.2 (1H, s), 8.49 (1H, d), 8.24 (1H, dd), 8.14 (1H, d), 4.43 (2H, t), 4.06–3.99 (2H, m), 3.76–3.64 (6H, m), 3.56 (4H, q), 2.00–1.90 (4H, m), 1.22 (6H, t), 1.13 (6H, t) | oil at ordinary temperature |
| 140 | 2981, 2931, 2892, 2874, 2222, 1607, 1564, 1478, 1343, 1266, 1203, 1108 | 7.73–7.54 (2H, m), 7.08 (1H, dd), 4.51 (1H, q), 4.48 (1H, q), 4.09 (3H, s), 4.11–3.81 (2H, m), 3.77–3.36 (2H, m), 1.62 (3H, d), 1.59 (3H, d), 1.27 (3H, t), 1.26 (3H, t) | 57.6–60.0 |
| 141 | 2979, 2933, 2892, 2867, 2221, 1339, 1323, 1199, 1112 | 7.97–7.80 (1H, m), 7.74–7.52 (2H, m), 4.52 (2H, q), 4.18–3.79 (2H, m), 3.77–3.36 (2H, m), 2.78 (3H, s), 1.63 (6H, d), 1.29 (3H, t), 1.28 (3H, t) | 63.3–66.3 |
| 142 | 2980, 2933, 2893, 2870, 2222, 1728, 1340, 1279, 1109, 783, 756 | 8.23–8.04 (2H, m), 7.76 (1H, dd), 4.67–4.37 (2H, q), 4.07–3.79 (2H, m), 4.04 (3H, s), 3.75–3.36 (2H, m), 1.62 (3H, d), 3.61 (3H, d), 1.28 (6H, t) | 40.3–41.0 |
| 143 | 2970, 2933, 2878, 2226, 1607, 1565, 1479, 1459, 1339, 1272, 1201, 1155, 1106, 771 | 7.78–7.50 (2H, m), 7.08 (1H, dd), 4.40 (1H, t), 4.37 (1H, t), 4.09 (3H, s), 4.11–3.84 (2H, m), 3.77–3.47 (6H, m), 3.40 (6H, s), 2.14–1.69 (4H, m), 1.12 (3H, t), 1.11 (3H, t) | oil at ordinary temperature |
| 144 | 2935, 2930, 2838, 2225, 1464, 1459, 1337, 1195, 1140, 1128, 1109, 1089, 777 | 7.97–7.78 (1H, m), 7.74–7.52 (2H, m), 4.40 (2H, t), 4.20–3.88 (2H, m), 3.84–3.54 (6H, m), 3.41 (3H, s), 3.40 (3H, s), 2.77 (3H, s), 2.14–1.74 (4H, m), 1.13 (6H, t) | oil at ordinary temperature |
| 145 | 2978, 2935, 2899, 2866, 2226, 1616, 1502, 1352, 1230, 1110, 1009, 841 | 7.30 (2H, s), 4.50 (2H, q), 4.14–3.79 (2H, m), 4.03 (6H, s), 3.71–3.36 (2H, m), 1.61 (6H, d), 1.27 (6H, t) | 92.6–93.3 |
| 146 | 2981, 2933, 2870, 2227, 1616, 1487, 1344, 1217, 1163, 1120, 1086, 976, 833 | *7.92 (1H, d), 7.40 (1H, dd), 3.31 (1H, d), 3.96 (3H, s), 3.88 (4H, t), 3.64 (4H, t), 3.55 (4H, q), 1.67 (12H, s), 1.21 (6H, t) | oil at ordinary temperature |
| 147 | 2974, 2933, 2868, 2224, 1462, 1392, 1371, 1340, 1215, 1159, 1122, 1086, 997, 764 | *8.06–8.02 (2H, m), 7.77–7.74 (2H, m), 3.88–3.84 (4H, m), 3.64 (4H, t), 3.56 (4H, q), 1.97–1.88 (4H, m), 1.61 (6H, s), 1.21 (6H, t), 1.11 (6H, t) | oil at ordinary temperature |
| 148 | 2974, 2937, 2875, 2222, 1460, 1394, 1344, 1211, 1122, 1090, 980, 764 | *8.06–8.02 (2H, m), 7.77–7.73 (2H, m), 3.83 (4H, t), 3.64 (4H, t), 3.56 (4H, q), 1.98–1.84 (8H, m), 1.20 (6H, t), 1.06 (12H, t) | oil at ordinary temperature |
| 149 | 2985, 2931, 2875, 2819, 2227, 1689, 1402, 1362, 1338, 1302, 1227, 1165, 1130, 1084, 974, 841 | *8.60 (1H, d), 8.32 (1H, dd), 8.09 (1H, d), 3.88 (4H, t), 3.63–3.60 (4H, m), 3.41 (6H, s), 2.75 (3H, s), 1.69 (12H, s) | oil at ordinary temperature |
| 150 | — | *8.60 (1H, d), 8.32 (1H, dd), 8.09 (1H, d), 3.88 (4H, t), 3.65 (4H, t), 3.56 (4H, q), 2.75 (3H, s), 1.68 (12H, s), 1.21 (6H, t) | oil at ordinary temperature |
| 151 | 3425, 3417, 2974, 2931, 2872, 2226, 1458, 1443, 1346, 1189, 1109, 1026, 985, 829 | *8.03 (1H, d), 8.01 (1H, d), 7.77 (1H, dd), 4.94 (2H, d), 4.41 (2H, t), 4.06–4.00 (2H, m), 3.75–3.64 (6H, m), 3.55 (4H, q), 2.01–1.89 (4H, m), 1.22 (6H, t), | oil at ordinary temperature |

TABLE 6-continued

| No.** | IR (cm⁻¹) | NMR (CDCl₃, δ, ppm) | Melting point (°C.) |
|---|---|---|---|
| 152 | 2985, 2933, 2877, 2227, 1616, 1487, 1446, 1344, 1252, 1217, 1198, 1163, 1128, 1084, 1026, 972, 833 | 1.12 (6H, t) *7.92 (1H, d), 7.40 (1H, dd), 7.33 (1H, d), 3.96 (3H, s), 3.88 (4H, t), 3.63–3.59 (4H, m), 3.40 (6H, s), 1.68 (6H, s), 1.67 (6H, s) | oil at ordinary temperature |
| 153 | 3433, 2985, 2931, 2877, 2819, 2227, 1454, 1379, 1360, 1340, 1228, 1188, 1161, 1128, 1082, 1034, 974, 829 | *8.03 (1H, d), 8.01 (1H, d), 7.77 (1H, dd), 4.94 (2H, d), 3.90–3.87 (4H, m), 3.63–3.59 (4H, m), 3.40 (6H, s), 1.98 (1H, t), 1.68 (12H, s) | oil at ordinary temperature |
| 154 | 3404, 2983, 2933, 2870, 2227, 1379, 1358, 1342, 1252, 1228, 1188, 1163, 1124, 1084, 978, 831 | *8.03 (1H, d), 8.01 (1H, d), 7.77 (1H, dd), 4.94 (2H, d), 3.88 (4H, t), 3.65 (4H, t), 3.56 (4H, q), 1.99 (1H, t), 1.68 (12H, s), 1.21 (6H, t) | oil at ordinary temperature |

**Compounds of Examples

Thus, as has been described in the foregoing, it is evident that the novel compound of the present invention has a broad range of antiulcer activities, because it shows efficient function to inhibit proton pump and gastric acid secretion. In addition, since the novel compound of the present invention has a cell protection effect and high safety, it is expected that the novel compound will show strong acid secretion inhibition activity and mucosa protection effect in clinical or animal experimental systems and exhibits excellent effects in preventing and/or treating peptic ulcer-related diseases and in preventing relapse thereof.

Also, the pharmaceutical composition of the present invention can achieve the purpose of preventing and/or treating various diseases generally known as the indication of gastric acid secretion inhibitors or gastric mucosa protecting drugs. That is, the inventive composition is effective in preventing and/or treating gastric ulcer, duodenal ulcer, anastomotic ulcer, Zollinger-Ellison syndrome, gastritis and reflux esophagitis, as well as in treating and/or preventing morbid states of these diseases on which prior art drugs cannot show sufficient efficacy. The compound of the present invention can also be used in patients suffering from other diseases which require gastric acid secretion inhibiting or gastric mucosa protecting function, such as those patients having NSAID (non-steroidal anti-inflammatory drug)-induced gastritis, acute upper gastrointestinal bleeding and past history of gastritis caused by chronic or acute alcohol taking. It is also useful for the medication prior to anesthesia.

What is claimed is:

1. A compound represented by the following formula (I) or a salt thereof

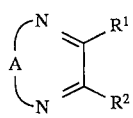

wherein A is a group represented by the following formula (III);

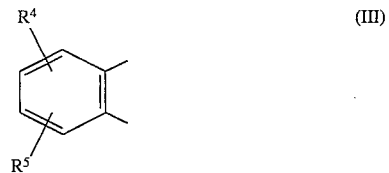

$R^1$ is a group represented by the following formula (IV);

$R^6$ represents a hydrogen atom, a straight- or branched-chain or cyclic alkyl group having 1 to 6 carbon atoms or an alkoxy group having 1 or 2 carbon atoms; $R^7$ represents a hydrogen atom or an alkyl group having 1 or 2 carbon atoms, or $R^6$ and $R^7$ together with their adjoining carbon atom may form a cycloalkylidene group having 3 to 6 carbon atoms or $R^6$, $R^7$ and $R^8$ together with their adjoining carbon atom may form a cycloalkyl group having 3 to 6 carbon atoms; $R^8$ represents a hydrogen atom, a straight- or branched-chain alkyl group having 1 to 3 carbon atoms which may be substituted with a group selected from an alkoxy group having 1 or 2 carbon atoms and an alkylthio group having 1 or 2 carbon atoms, an alkenyloxy group having 2 to 4 carbon atoms, a straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms, a carbamoyloxy group, an acetoxy group or a methylthio group; $R^2$ represents a hydrogen atom, a methoxy group, a halogen atom, an amino group which may be substituted with 1 or 2 alkyl groups having 1 or 2 carbon atoms, a trifluoromethyl group, a straight- or branched-chain alkyl group having 1 to 6 carbon atoms, an alkoxycarbonyl group having 1 or 2 carbon atoms, a methylthio group, a methylsulfinyl group, a methylsulfonyl group or a group selected from the aforementioned groups represented by $R^1$; $R^1$ and $R^2$ may be the same or different from each other;

$R^4$ represents a hydrogen atom or a methoxy group; and $R^5$ represents a hydrogen atom, a methoxy group, a halogen atom, a methoxycarbonyl group, a methyl group, a hydroxymethyl group, a methoxymethyl group, a carbamoyl group, a bis(ethoxycarbonyl)acetyl group, an acetyl group, a 1-hydroxyiminoethyl group, a 1-methoxyiminoethyl group, a formyl group or a cyano group.

2. The compound or a salt thereof according to claim 1 wherein $R^1$ in the aforementioned formula (I) is represented by the following formula (IV),

$R^1$ and $R^2$ are the same group and $R^8$ is a straight- or branched-chain alkyl group having 1 to 3 carbon atoms which is substituted with an alkoxy group having 1 or 2 carbon atoms or $R^8$ is a straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms.

3. The compound or a salt thereof according to claim 1 or 2 wherein A in the aforementioned formula (I) is represented by the aforementioned formula (III), $R^4$ is a hydrogen atom, $R^5$ is a hydrogen atom or a methoxy, hydroxymethyl or acetyl group at the 6-position and $R^7$ is an alkyl group having 1 or 2 carbon atoms.

4. A compound which is selected from the group consisting of an optically active or an optically inactive stereoisomer of the compound of claim 3 and salts thereof.

5. A composition which comprises:
a compound represented by the following formula (I) or a pharmaceutically acceptable salt thereof as an active ingredient

wherein A is a group represented by the following formula (III);

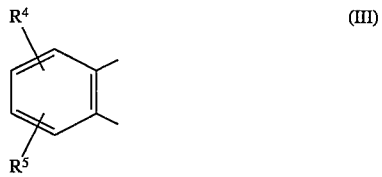

$R^1$ is a group represented by the following formula (IV);

$R^6$ represents a hydrogen atom, a straight- or branched-chain or cyclic alkyl group having 1 to 6 carbon atoms or an alkoxy group having 1 or 2 carbon atoms; $R^7$ represents a hydrogen atom or an alkyl group having 1 or 2 carbon atoms, or $R^6$ and $R^7$ together with their adjoining carbon atom may form a cycloalkylidene group having 3 to 6 carbon atoms or $R^6$, $R^7$ and $R^8$ together with their adjoining carbon atom may form a cycloalkyl group having 3 to 6 carbon atoms; $R^8$ represents a hydrogen atom, a straight- or branched-chain alkyl group having 1 to 3 carbon atoms which may be substituted with a group selected from an alkoxy group having 1 or 2 carbon atoms and an alkylthio group having 1 or 2 carbon atoms, an alkenyloxy group having 2 to 4 carbon atoms, a straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms, a carbamoyloxy group, an acetoxy group or a methylthio group; $R^2$ represents a hydrogen atom, a methoxy group, a halogen atom, an amino group which may be substituted with 1 or 2 alkyl groups having 1 or 2 carbon atoms, a trifluoromethyl group, a straight- or branched-chain alkyl group having 1 to 6 carbon atoms, an alkoxycarbonyl group having 1 or 2 carbon atoms, a methylthio group, a methylsulfinyl group, a methylsulfonyl group or a group selected from the aforementioned groups represented by $R^1$; $R^1$ and $R^2$ may be the same or different from each other; $R^4$ represents a hydrogen atom or a methoxy group; and $R^5$ represents a hydrogen atom, a methoxy group, a halogen atom, a methoxycarbonyl group, a methyl group, a hydroxymethyl group, a methoxymethyl group, a carbamoyl group, a bis(ethoxycarbonyl)acetyl group, an acetyl group, a 1-hydroxyiminoethyl group, a 1-methoxyiminoethyl group, a formyl group or a cyano group; and a pharmaceutically acceptable carrier therefor.

6. A method of treating or preventing peptic ulcer-related diseases comprising the step of:
administering to a patient in need thereof, an effective amount of said compound or said pharmaceutically acceptable salt thereof according to claim 1.

7. A method of inhibiting the secretion of gastic acid comprising:
administering to a patient an effective amount of said compound or a pharmaceutically acceptable salt thereof according to claim 1.

8. A process for producing the compound (I) of claim 1 or a salt thereof which comprises allowing a compound represented by the following formula (V)

wherein A is a group represented by the following formula (III);

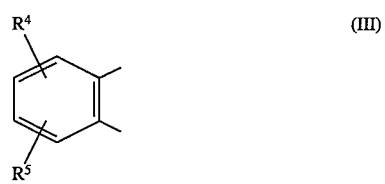

X represents a halogen atom; $R^2$ represents a hydrogen atom, a methoxy group, a halogen atom, an amino group which may be substituted with 1 or 2 alkyl groups having 1 or 2 carbon atoms, a trifluoromethyl group, a straight- or branched-chain alkyl group having 1 to 6 carbon atoms, an alkoxycarbonyl group having 1 or 2 carbon atoms, a methylthio group, a methylsulfinyl group, a methylsulfonyl group or a group represented by the following formula (IV);

$$-C\equiv C-\underset{R^7}{\overset{R^6}{\underset{|}{\overset{|}{C}}}}-R^8 \qquad (IV)$$

$R^6$ represents a hydrogen atom, a straight- or branched-chain or cyclic alkyl group having 1 to 6 carbon atoms or an alkoxy group having 1 or 2 carbon atoms; $R^7$ represents a hydrogen atom or an alkyl group having 1 or 2 carbon atoms, or $R^6$ and $R^7$ together with their adjoining carbon atom may form a cycloalkylidene group having 3 to 6 carbon atoms or $R^6$, $R^7$ and $R^8$ together with their adjoining carbon atom may form a cycloalkyl group having 3 to 6 carbon atoms; $R^8$ represents a hydrogen atom, a straight- or branched-chain alkyl group having 1 to 3 carbon atoms which may be substituted with a group selected from an alkoxy group having 1 or 2 carbon atoms and an alkylthio group having 1 or 2 carbon atoms, an alkenyloxy group having 2 to 4 carbon atoms, a straight- or branched-chain alkoxy group having 1 to 4 carbon atoms which may be substituted with a group selected from a straight- or branched-chain alkoxy group having 1 to 3 carbon atoms and an alkoxycarbonyl group having 1 or 2 carbon atoms, a carbamoyloxy group, an acetoxy group or a methylthio group; $R^4$ represents a hydrogen atom or a methoxy group; and $R^5$ represents a hydrogen atom, a methoxy group, a halogen atom, a methoxycarbonyl group, a methyl group, a hydroxymethyl group, a methoxymethyl group, a carbamoyl group, a bis(ethoxycarbonyl)acetyl group, an acetyl group, a 1-hydroxyiminoethyl group, a 1-methoxyiminoethyl group, a formyl group, or a cyano group, to react with a compound represented by the following formula (VI)

$$M-R^1 \qquad (VI)$$

wherein M represents a hydrogen atom, a lithium atom, a magnesium atom, a mercury atom, a zinc atom, a copper atom or a boron, aluminum, silicon or tin atom which may be substituted with one or more alkyl groups having 1 to 4 carbon atoms and $R^1$ is a group represented by the aforementioned formula (IV), in the presence or absence of a metal catalyst.

* * * * *